(12) United States Patent  
Beavers et al.

(10) Patent No.: US 8,008,301 B2
(45) Date of Patent: *Aug. 30, 2011

(54) HISTAMINE H3 RECEPTOR AGENTS, PREPARATION AND THERAPEUTIC USES

(75) Inventors: Lisa Selsam Beavers, Franklin, IN (US); Don Richard Finley, Greenwood, IN (US); Terry Patrick Finn, Basingstoke (GB); Robert Alan Gadski, Indianapolis, IN (US); Philip Arthur Hipskind, New Palestine, IN (US); William Joseph Hornback, Fishers, IN (US); Cynthia Darshini Jesudason, Indianapolis, IN (US); Richard Todd Pickard, Noblesville, IN (US); Takako Takakuwa, Indianapolis, IN (US); Grant Mathews Vaught, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/610,954

(22) Filed: Nov. 2, 2009

(65) Prior Publication Data

US 2010/0048580 A1 Feb. 25, 2010

Related U.S. Application Data

(62) Division of application No. 10/499,488, filed on Jun. 17, 2004, now abandoned.

(60) Provisional application No. 60/558,542, filed on Apr. 1, 2004, provisional application No. 60/617,101, filed on Oct. 8, 2004.

(51) Int. Cl.
*A61K 31/501* (2006.01)
*A61K 31/4439* (2006.01)
*A61K 31/4245* (2006.01)
*A61K 31/4025* (2006.01)
*C07D 403/06* (2006.01)
*C07D 413/14* (2006.01)
*C07D 401/14* (2006.01)

(52) U.S. Cl. ............ 514/252.05; 514/256; 514/343; 514/364; 514/422; 544/238; 544/333; 546/279.1; 548/143; 548/524

(58) Field of Classification Search .......... None
See application file for complete search history.

(56) References Cited

U.S. PATENT DOCUMENTS 7,632,857 B2 * 12/2009 Hornback et al. .......... 514/422
2007/0155754 A1 7/2007 Beavers 2007/0197604 A1 8/2007 Beavers
2008/0015235 A1 1/2008 Jesudason
2008/0207732 A1 8/2008 Beavers
2009/0048225 A1 2/2009 Finley
2009/0118254 A1 5/2009 Beavers

FOREIGN PATENT DOCUMENTS

WO 02/076295 A2 10/2002
WO 03/064411 A1 8/2003
WO 2004/076412 A2 9/2004
WO 2006/107661 A1 10/2006
WO 2007/005503 A1 1/2007

OTHER PUBLICATIONS de Ferranti S, and Mozaffarian D, "The perfect storm: obesity, adipocyte dysfunction, and metabolic consequences," Clinical Chemistry, Jun. 2008, 54(6), 945-955.

Dick JJ, "Weight loss interventions for adult obesity: evidence for practice," Worldviews on Evidence-Based Nursing, 2004, 1(4), 209-214.

Esbenshade TA, Fox GB, and Cowart MD, "Histamine H3 receptor antagonists: preclinical promise for treating obesity and cognitive disorders," Molecular Interventions, Apr. 2006, 6(2), 77-88.

Hancock AA, Bush EN, Jacobson PB, Faghih R, and Esbenshade TA, "Histamine H(3) antagonists in models of obesity," Inflammation Research, Mar. 2004, 53(Suppl 1), S47-S48.

* cited by examiner

*Primary Examiner* — Kamal Saeed
(74) *Attorney, Agent, or Firm* — Dan L. Wood

(57) ABSTRACT

The present invention discloses novel compounds of Formula (I) or pharmaceutically acceptable salts thereof, which have histamine—H3 receptor antagonist or inverse agonist activity, as well as methods for preparing such compounds. In another embodiment, the invention discloses pharmaceutical compositions comprising compounds of Formula (I) as well as methods of using them to treat obesity, cognitive deficiencies, narcolepsy, and other histamine H3 receptor—related diseases

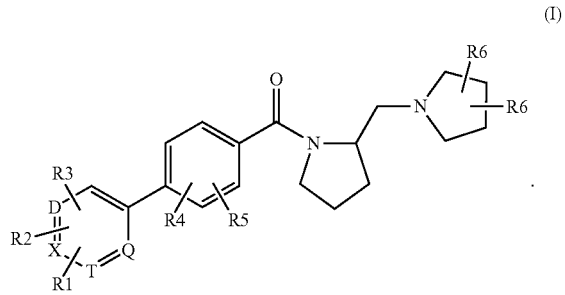

14 Claims, No Drawings

HISTAMINE H3 RECEPTOR AGENTS, PREPARATION AND THERAPEUTIC USES

This is a divisional application of 10/499,488 filed 06/17/2004 now abandoned and claims the benefit of U.S. Provisional Application No. 60/558,542 filed Apr. 1, 2004, and U.S. Provisional Application No. 60/617,101 filed Oct. 8, 2004.

FIELD OF THE INVENTION

The present invention relates to novel biaryl compounds, and to the use of these compounds as pharmaceutical compositions, to pharmaceutical compositions comprising the compounds, to methods of treatment employing these compounds and compositions, and to intermediates and methods for making these compounds.

BACKGROUND OF THE INVENTION

The histamine H3 receptor is relatively neuron specific and inhibits the release of a number of monoamines, including histamine. The histamine H3 receptor is a presynaptic autoreceptor and hetero-receptor located both in the central and the peripheral nervous system. The histamine H3 receptor regulates the release of histamine and other neurotransmitters, such as serotonin and acetylcholine. These are examples of histamine H3 receptor mediated responses. Recent evidence suggests that the H3 receptor shows intrinsic, constitutive activity, in vitro as well as in vivo (i.e. it is active in the absence of an agonist). Compounds acting as inverse agonists can inhibit this activity. A histamine H3 receptor antagonist or inverse agonist would therefore be expected to increase the release of H3 receptor-regulated neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists, and antagonists could be important mediators of neuronal activity, and the activities of other cells that may express this receptor. Inverse agonism or selective antagonism of the histamine H3 receptor raises brain levels of histamine, and other monoamines, and inhibits activities such as food consumption while minimizing non-specific peripheral consequences. By this mechanism, they induce a prolonged wakefulness, improved cognitive function, reduction in food intake and normalization of vestibular reflexes. Accordingly, the histamine H3 receptor is an important target for new therapeutics in Alzheimer disease, mood and attention adjustments, cognitive deficiencies, obesity, dizziness, schizophrenia, epilepsy, sleeping disorders, narcolepsy and motion sickness.

Histamine mediates its activity via four receptor subtypes, H1R, H2R, H3R and a newly identified receptor designated GPRv53 [(Oda T., et al., J. Biol. Chem. 275 (47): 36781-6 (2000)], and alternative names for this receptor are PORT3 or H4R. Although relatively selective ligands have been developed for H1R, H2R and H3R, few specific ligands have been developed that can distinguish H3R from GPRv53. GPRv53 is a widely distributed receptor found at high levels in human leukocytes. Activation or inhibition of this receptor could result in undesirable side effects when targeting antagonism of the H3R receptor. The identification of the H4R receptor has fundamentally changed histamine biology and must be considered in the development of histamine H3 receptor antagonists.

Some histamine H3 receptor antagonists were created which resembled histamine in possessing an imidazole ring generally substituted in the 4(5) position (Ganellin et al., Ars Pharmaceutica, 1995, 36:3, 455-468). A variety of patents and patent applications directed to antagonists and agonists having such structures include EP 197840, EP 494010, WO 97/29092, WO 96/38141, and WO96/38142. These imidazole-containing compounds have the disadvantage of poor blood-brain barrier penetration, interaction with cytochrome P-450 proteins, and hepatic and ocular toxicities. Recently other imidazole and non-imidazole ligands of the histamine H3 receptor have been described. The compounds of the present invention differ in structure from the compounds described in the art.

There remains a need for improved treatments using alternative or improved pharmaceutical agents that act as histamine H3 receptor agonists, inverse agonists, or antagonists, to modulate H3 receptor activity, and treat the diseases that could benefit from H3 receptor modulation. The present invention provides such a contribution to the art based on the finding that a novel class of biaryl amine compounds has a high affinity, selective, and potent activity at the histamine H3 receptor. The subject invention is distinct in the particular structures and their activities.

SUMMARY OF THE INVENTION

The present invention is a compound structurally represented by Formula I:

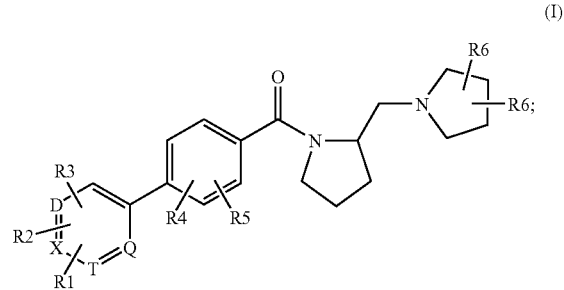

(I)

or a pharmaceutically acceptable salt thereof wherein:
Q, T, X, and D independently represent carbon or nitrogen, provided that no more than two of Q, T, X, and D are nitrogen;
R1, R2, and R3 are independently at each occurrence
—H,
-halogen,
—($C_1$-$C_7$)alkyl,
—CN,
—C(O)R7,
—C(O)($C_3$-$C_5$)cycloalkyl,
—C(O)NR7R8,
—OCF$_3$,
—OR7,
—NO$_2$,
—NR7R8,
—NR9SO$_2$R7,
—NR9C(O)R7,
—NR9CO$_2$R7,
—NR9C(O)NR7R8,
—SR7,
—SO$_2$R7,
—SO$_2$CF$_3$, —SO₂NR7R8,
—S(O)R7,
—O(CH₂)mNR7R8,
-heteroaryl-R9,
-phenyl-R9,
provided however that wherein D is nitrogen, then R1 or R2 or R3 are not attached to D, and provided that wherein X is nitrogen, then R1 or R2 or R3 are not attached to X, and provided that wherein T is nitrogen, then R1 or R2 or R3 are not attached to T, and provided that wherein Q is nitrogen, then R1 or R2 or R3 are not attached to Q;
and further provided that when D and X are carbon, then R1 and R2 can combine to form a 5 or 6 membered ring with D and X,

wherein the ring so formed may optionally include one double bond in the case of a five membered ring or two double bonds in the case of a six membered ring, and wherein one to three ring atoms may optionally be heteroatoms independently selected from N, O, or S;
wherein m is 1, 2, 3 or 4;
R4 and R5 are independently each occurrence
—H,
—OH,
-halogen,
—CF₂H,
—CF₃,
—(C₁-C₃)alkyl,
—O—(C₁-C₃)alkyl,
R6 is independently at each occurrence
—H,
-halogen,
—CF₃,
—(C₁-C₃)alkyl,
—NH₂,
—NR7R8,
—OH,
—OR7;
R7 and R8 are independently each occurrence
—H,
—(C₁-C₆)alkyl,
Wherein R7 and R8 can combine with the atom to which they are attached to form a 3 to 7 membered ring;
R9 is independently each occurrence
—H,
—(C₁-C₃)alkyl.

The present invention provides compounds that show a selective and high affinity binding for the histamine H3 receptor, and thus the compounds are useful as histamine H3 receptor antagonists or inverse agonists. In an other aspect, the present invention provides compounds that are useful as selective antagonists or inverse agonists of the histamine H3 receptor but have little or no binding affinity of GPRv53. In addition, the present invention provides a method for the treatment of a nervous system disorder, which comprises administering to a patient in need thereof an effective amount of a compound of formula I. The present invention further provides a method for the treatment of obesity or cognitive disorders, which comprises administering to a patient in need thereof an effective amount of a compound of formula I. In yet another aspect, the present invention provides pharmaceutical compositions comprising antagonists or inverse agonists of the histamine H3 receptor.

DETAILED DESCRIPTION OF THE INVENTION

General terms used in the description of compounds, compositions, and methods herein described, bear their usual meanings. Throughout the instant application, the following terms have the indicated meanings:

The term "GPRv53" means a recently identified novel histamine receptor as described in Oda, et al., supra. Alternative names for this receptor are PORT3 or H4R.

The term "H3R" means the histamine H3 receptor that inhibits the release of a number of monoamines, including histamine.

The term "H1R" means the histamine H1 receptor subtype.
The term "H2R" means the histamine H2 receptor subtype.
The term "selective H3R antagonists" is defined as the ability of a compound of the present invention to block forskolin-stimulated cAMP production in response to agonist R(-)α methylhistamine.

The term "H3R inverse agonist" is defined as the ability of a compound of the present invention to inhibit the constitutive activity of H3R.

In the general formulae of the present document, the general chemical terms have their usual meanings. For example; "C₁-C₃ Alkyl" are one to three carbon atoms such as methyl, ethyl, propyl, and the like, and branched or isomeric forms thereof, and as herein defined optionally may be substituted with one to three halogens. "C₁-C₇ Alkyl" are one to seven carbon atoms such as methyl, ethyl, propyl, butyl, pentyl, hexyl, heptyl, and the like, and branched or isomeric forms thereof, and as herein defined optionally may be substituted with one to three halogens.

"Cycloalkyl" means a ring with three to seven carbon atoms such as cyclopropyl, cyclobutyl, cyclopentyl and cyclohexyl, cycloheptyl, and the like.

"Heteroaryl" means a monocyclic aromatic ring containing five atoms, and containing at least one ring heteroatom selected from N, O and S (including SO and SO₂). Examples of heteroaryl include pyrrolyl, isoxazolyl, isothiazoyl, pyrazolyl, oxazolyl, oxadiazolyl, thiadiazolyl, thiazolyl, imidazolyl, triazolyl, tetrazolyl, furanyl, thienyl, and the like.

"Boc" or "BOC" refer to t-butyl carbamate.
"HOBt" is 1-hydrobenzotriazole.
"PS-Trisamine" is Tris-(2-aminoethyl)amine polystyrene. "PS-Carbodiimide" or "PS-CDI" is N-Cyclohexylcarbodiimide-N'-propyloxymethyl polystyrene. "PS-DIEA" is N,N-(Diisopropyl)aminomethylpolystyrene (1% inorganic antistatic agent). "PS-DMAP" is N-(methylpolystyrene)-4-(methylamino) pyridine.

"Halogen" or "halo" means fluoro, chloro, bromo and iodo.
"Composition" means a pharmaceutical composition and is intended to encompass a pharmaceutical product comprising the active ingredient(s), Formula I, and the inert ingredient(s) that make up the carrier. Accordingly, the pharmaceutical compositions of the present invention encompass any composition made by admixing a compound of the present invention and a pharmaceutically acceptable carrier.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The terms "treating" and "treat", as used herein, include their generally accepted meanings, i.e., preventing, prohibiting, restraining, alleviating, ameliorating, slowing, stopping, or reversing the progression or severity of a pathological condition, described herein.

In one embodiment, the present invention provides compounds of Formula I as described in detail above. While all of the compounds of the present invention are useful, certain of the compounds are particularly interesting and are preferred. The following listing sets out several groups of preferred compounds. It will b e understood that each of the listings may be combined with other listings to create additional groups of preferred embodiments. Other embodiments are, 1. wherein D, X, Q and T are carbon,
2. wherein X is carbon and R1 is attached to X,
3. wherein D is carbon and R1 is attached to D,
4. wherein X is carbon and R1 is attached to X and R1 is selected from thy group consisting of; —NR9SO$_2$R7, —SO$_2$R7, —SO$_2$CF$_3$, —SO$_2$NR7R8, —S(O)R7,
5. wherein one of D, X, Q or T is nitrogen,
6. wherein D is nitrogen,
7. wherein X is nitrogen,
8. wherein Q is nitrogen,
9. wherein two of D, X, Q or T are nitrogen,
10. wherein D and T are nitrogen,
11. wherein Q and X are nitrogen,
12. wherein R4 is halogen,
13. wherein R4 is halogen and R5 is halogen,
14. wherein one independent occurrence of R6 is —(C$_1$-C$_3$)alkyl,
15. wherein one independent occurrence of R6 is —CH$_3$,
16. A compound of Formula (II),

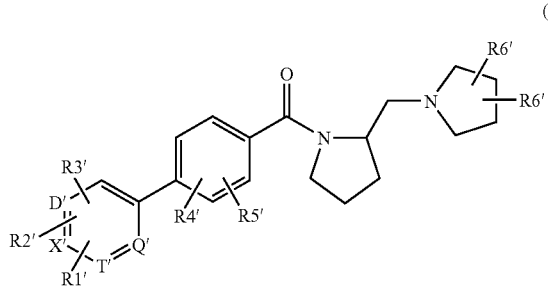

(II)

or a pharmaceutically acceptable salt thereof wherein:
Q', T', X', and D' independently represent carbon or nitrogen, provided that no more than two of Q', T', X', and D' are nitrogen;
R1' is
-halogen,
—(C$_1$-C$_7$)alkyl,
—CN,
—C(O)R7',
—C(O)(C$_3$-C$_5$)cycloalkyl,
—C(O)NR7'R8',
—OCF$_3$,
—OR7',
—NO$_2$,
—NR7'R8',
—NR9'SO$_2$R7',
—NR9'C(O)R7',
—NR9'CO$_2$R7',
—NR9'C(O)NR7'R8',
—SR7',
—SO$_2$R7',
—SO$_2$CF$_3$,
—SO$_2$NR7'R8',
—S(O)R7',
—O(CH$_2$)mNR7'R8',
-heteroaryl-R9',
R2' and R3' are independently at each occurrence
—H,
-halogen,
—(C$_1$-C$_7$)alkyl,
—CN,
—C(O)R7',
—C(O)(C$_3$-C$_5$)cycloalkyl,
—C(O)NR7'R8',
—OCF$_3$,
—OR7',
—NO$_2$,
—NR7'R8',
—NR9'SO$_2$R7',
—NR9'C(O)R7',
—NR9'CO$_2$R7',
—NR9'C(O)NR7'R8',
—SR7',
—SO$_2$R7',
—SO$_2$CF$_3$,
—SO$_2$NR7'R8',
—S(O)R7',
—O(CH$_2$)mNR7'R8',
heteroaryl-R9',
provided however that wherein D' is nitrogen, then R1' or R2' or R3' are not attached to D', and provided that wherein X' is nitrogen, then R1' or R2' or R3' are not attached to X', and provided that wherein T' is nitrogen, then R1' or R2' or R3' are not attached to T', and provided that wherein Q' is nitrogen, then R1' or R2' or R3' are not attached to Q';
wherein m is 1, 2, 3 or 4;
R4' and R5' are independently at each occurrence
—H,
-halogen,
—CF$_3$,
—(C$_1$-C$_3$)alkyl,
provided that when R4' is —H, then R5' is not —H,
R6' is independently at each occurrence
—H,
-halogen,
—CF$_3$,
—(C$_1$-C$_3$)alkyl,
R7' and R8' are independently at each occurrence;
—H,
—(C$_1$-C$_6$)alkyl,
Wherein R7' and R8' can combine with the atom to which they are attached to form a 3 to 7 membered ring;
R9' is independently at each occurrence
—H,
—(C$_1$-C$_3$)alkyl.

Due to their interaction with the histamine H3 receptor, the present compounds are useful in the treatment of a wide range of conditions and disorders in which an interaction with the histamine H3 receptor is beneficial. Thus, the compounds may find use for example to prevent, treat and/or alleviate diseases or conditions of the central nervous system, the peripheral nervous system, the cardiovascular system, the pulmonary system, the gastrointestinal system and the endocrinological system, while reducing and or eliminating one or more of the unwanted side effects associated with the current treatments. Such diseases or conditions include those responsive to the modulation of histamine H3 receptors, such as nervous system disorders which include but are not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, as well as cardiovascular disorders such as acute myocardial infarction; cancer such as cutaneous carcinoma, medullary thyroid carcinoma and melanoma; respiratory disorders such as asthma; gastrointestinal disorders, inflammation, and septic shock, diabetes, type II diabetes, insulin resistance syndrome, metabolic syndrome, polycystic ovary syndrome, Syndrome X, and the like.

The present invention also provides a pharmaceutical composition which comprises a compound of Formula I or Formula II and a pharmaceutically acceptable carrier. Pharmaceutical formulations of Formula I or Formula II can provide a method of selectively increasing histamine levels in cells, or increasing histamine release by cells, by contacting the cells with an antagonist or inverse agonist of the histamine H3 receptor, the antagonist or inverse agonist being a compound of Formula I or Formula II. Thus, the methods of this invention encompass a prophylactic and therapeutic administration of a compound of Formula I or Formula II.

The present invention further provides an antagonist or inverse agonist of Formula I or Formula II which is characterized by having little or no binding affinity for the histamine receptor GPRv53.

Thus, a pharmaceutical preparation of Formula I or Formula II can be useful in the treatment or prevention of obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, which comprises administering to a subject in need of such treatment or prevention an effective amount of a compound of Formula I or Formula II. In addition, a pharmaceutical preparation of Formula I or Formula II can be useful in the treatment or prevention of a disorder or disease in which modulation of histamine H3 receptor activity has a beneficial effect or the treatment or prevention of eating disorders which comprises administering to a subject in need of such treatment or prevention an effective amount of a compound of Formula I or Formula II. In yet another aspect, the present invention provides compounds, pharmaceutical compositions, and methods useful in the treatment of nervous system and other disorders associated with histamine H3 receptor.

In addition, the present invention relates to a compound of Formulae I or II, or a pharmaceutical salt thereof, or a pharmaceutical composition which comprises a compound of Formulae I or II, or a pharmaceutical salt thereof, and a pharmaceutically acceptable carrier, diluent, or excipient; for use in inhibiting the histamine H3 receptor; for use in inhibiting a histamine H3 receptor mediated cellular response in a mammal; for use to increase the release of H3 receptor-regulated neurotransmitters in a mammal; for use in treating a disease arising from excessive histamine H3 receptor activity; and for use in treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo. Thus, the uses and methods of this invention encompass a prophylactic and therapeutic administration of a compound of Formulae I or II.

The present invention is further related to the use of a compound of Formulae I or II, or a pharmaceutical salt thereof, or a pharmaceutical composition which comprises a compound of Formulae I or II, or a pharmaceutical salt thereof, and a pharmaceutically acceptable carrier, diluent, or excipient; for the manufacture of a medicament for inhibiting the histamine H3 receptor; for the manufacture of a medicament for inhibiting a histamine H3 receptor mediated cellular response in a mammal; for the manufacture of a medicament to increase the release of H3 receptor-regulated neurotransmitters in the brain of a mammal; for the manufacture of a medicament for treating a disease arising from excessive histamine H3 receptor activity; for the manufacture of a medicament for treating cognitive disorders in a mammal; and for the manufacture of a medicament for treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo.

The present invention further provides; a method of treating conditions resulting from excessive histamine H3 receptor activity in a mammal; a method of inhibiting the histamine H3 receptor activity in a mammal; a method of inhibiting a histamine H3 receptor mediated cellular response in a mammal; a method to increase the release of H3 receptor-regulated neurotransmitters in the brain of a mammal; a method of treating cognitive disorders in a mammal; a method of treating nervous system disorders in a mammal including but not limited to obesity, cognitive disorders, attention and attention deficit disorders, memory processes, learning, dementia, Alzheimer's disease, attention-deficit hyperactivity disorder, Parkinson's disease, schizophrenia, depression, epilepsy, and seizures or convulsions; comprising administering to a mammal in need of such treatment a histamine H3 receptor-inhibiting amount of a compound of Formulae I or II or a pharmaceutically acceptable salt thereof, or a pharmaceutical composition which comprises a compound of Formulae I or II, or a pharmaceutical salt thereof, and a pharmaceutically acceptable carrier, diluent, or excipient.

The present invention further provides a method of treating conditions resulting from excessive histamine H3 receptor activity in a mammal comprising administering to a mammal in need of such treatment a histamine H3 receptor inhibiting amount of a pharmaceutical composition which comprises a compound of Formulae I or II, or a pharmaceutical salt thereof, and a pharmaceutically acceptable carrier, diluent, or excipient. In addition, a pharmaceutical composition of Formulae I or II can be useful in the treatment or prevention of a disorder or disease in which modulation of histamine H3 receptor activity has a beneficial effect. The present invention further provides an antagonist or inverse agonist of Formulae I or II which is characterized by having greater affinity for the histamine H3 receptor as compared to the affinity for the histamine H1R, H2R, or H4R receptors. In addition the embodiments of the present invention include the synthesis of the examples named herein by methods included herein, and supplemented by methods known in the art, to create positron emission topography (PET) ligands that bind to histamine H3 receptors and are useful for PET imaging.

The invention includes tautomers, enantiomers and other stereoisomers of the compounds also. Thus, as one skilled in the art knows, certain aryls may exist in tautomeric forms. Such variations are contemplated to be within the scope of the invention. It will be understood that, as used herein, references to the compounds of Formula I or Formula II are meant to also include the pharmaceutical salts, its enantiomers and racemic mixtures thereof.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I or Formula II can be prepared by one of ordinary skill in the art utilizing well known techniques and processes, such as those disclosed by J. Jacques, et al., "*Enantiomers, Racemates, and Resolutions*," John Wiley and Sons, Inc., 1981, and E. L. Eliel and S. H. Wilen, "*Stereochemistry of Organic Compounds*," (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counter-clockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation " ━ " refers to a bond that protrudes forward out of the plane of the page. The designation " ''''''' " refers to a bond that protrudes backward out of the plane of the page. The designation " ∼∼∼ " refers to a bond wherein the stereochemistry is not defined.

In general, the term "pharmaceutical" when used as an adjective means substantially non-toxic to living organisms. For example, the term "pharmaceutical salt" as used herein, refers to salts of the compounds of Formula I or Formula II which are substantially non-toxic to living organisms. See, e.g., Berge, S. M, Bighley, L. D., and Monkhouse, D. C., "Pharmaceutical Salts," *J. Pharm. Sci.*, 66:1, 1977. Typical pharmaceutical salts include those salts prepared by reaction of the compounds of Formula I or Formula II with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I or Formula II prepared by reaction of a compound of Formula I or Formula II with a mineral or organic acid. For exemplification of pharmaceutical acid addition salts see, e.g., Berge, S. M, Bighley, L. D., and Monkhouse, D.C., *J. Pharm. Sci.*, 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of Formula I or Formula II with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The term "base addition salt" refers to a salt of a compound of Formula I or Formula II prepared by reaction of a compound of Formula I or Formula II with a mineral or organic base. For exemplification of pharmaceutical base addition salts see, e.g., Berge, S. M, Bighley, L. D., and Monkhouse, D. C., *J. Pharm. Sci.*, 66:1, 1977. The present invention also contemplates pharmaceutical base addition salts of compounds of Formula I or Formula II. The skilled artisan would appreciate that some compounds of Formula I or Formula II may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formula I or Formula II.

The compounds of Formula I or Formula II, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I or Formula II may be obtained by stereospecific synthesis using optically pure starting materials or reagents of known configuration or through enantioselective synthesis.

The compounds of Formula I or Formula II can be prepared by one of ordinary skill in the art following a variety of procedures, some of which are illustrated in the procedures and schemes set forth below. The particular order of steps required to produce the compounds of Formula I or Formula II is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Preparations and Examples are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates (M+1) unless indicated otherwise. "MS (FD)" refers to field desorption mass spectrometry, "MS(IS)" refers to ion spray mass spectrometry, "MS(FIA)" refers to flow injection analysis mass spectrometry, "MS(FAB)" refers to fast atom bombardment mass spectrometry, "MS(EI)" refers to electron impact mass spectrometry, "MS(ES)" refers to electron spray mass spectrometry, "UV" refers to ultraviolet spectrometry, "$^1$H NMR" refers to proton nuclear magnetic resonance spectrometry. In addition, "IR" refers to infra red spectrometry, and the absorption maxima listed for the IR spectra are only those of interest and not all of the maxima observed. "RT" refers to room temperature.

PREPARATIONS AND EXAMPLES

General Preparations

SCHEME A

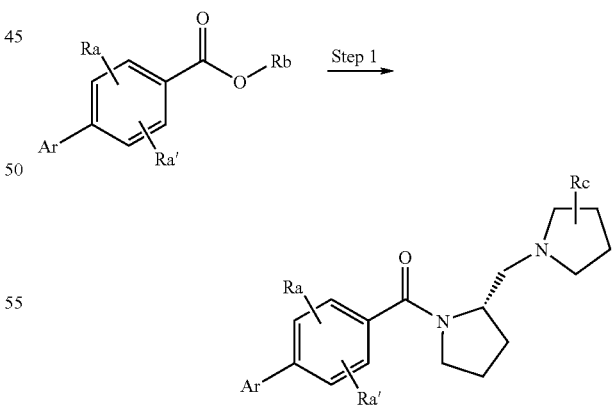

In Scheme A, $R_a$ and $R_{a'}$ are each independently but not limited to F, Cl, $CF_3$, alkyl and can include disubstituted compounds; $R_b$ is H, or the corresponding salts; $R_c$, can be but is not limited to alkyl, amino, hydroxy, and Ar is any mono, di or trisubstituted sir-membered aromatic or heteroaromatic ring not limited to phenyl, pyridine, pyrimidine, pyrazine, pyridazine. In Scheme 1, Step 1 biaryl carboxylic acids or the lithium, sodium or potassium salt of the acid where $R_b$ can be H, Li, Na or K are converted to the corresponding amides using a number of different methods known in the literature. Some of these methods can be found described in a review of coupling reagents in peptide synthesis by Klausner & Bodansky, Synthesis, 1972, 9, 453-463.

For example, 4'-trifluoromethyl-biphenyl-4-carboxylic acid (where Ar=4-trifluoromethyl phenyl) or the corresponding lithium or sodium salt is suspended a suitable organic solvent such as dichloromethane, DMF or mixtures thereof. A suitable amide coupling agent i.e EDC, DCC, TBTU, etc., is added followed by HOBt, HATU, etc., at room temperature. Diisopropylethyl amine and suitable amine in this case, (S)(+)-1-(2-pyrrolidinylmethyl)pyrrolidine are added to the mixture. The mixture is stirred at room temperature for a period of 8-48 hours. The reaction is quenched by addition of water. The resulting mixture may be extracted, concentrated and purified according to techniques well known in the art.

Alternatively the corresponding acid chloride can be formed from the corresponding acid or salt thereof using thionyl chloride or oxalyl chloride and a few drops DMF, and treated with a suitable amine to give the desired amide.

For example, 4'-cyclopropanecarbonyl-biphenyl-4-carboxylic acid (where Ar=4-cyclopropyl phenyl) is dissolved in 10 ml of thionyl chloride and stirred under reflux for a period of 1-12 hours and excess thionyl chloride is removed in vacuo. The residue is dissolved in a suitable solvent in this case $CH_2Cl_2$ to make acid chloride solution and is added to a solution of a suitable amine in this case (S)(+)-1-(2-pyrrolidinylmethyl)pyrrolidine and a proton scavenger i.e. triethylamine in $CH_2Cl_2$. The mixture is stirred at room temperature for a period of 30 minutes to 12 hours. The resulting mixture may be concentrated, extracted, and purified according to techniques well known in the art.

SCHEME B

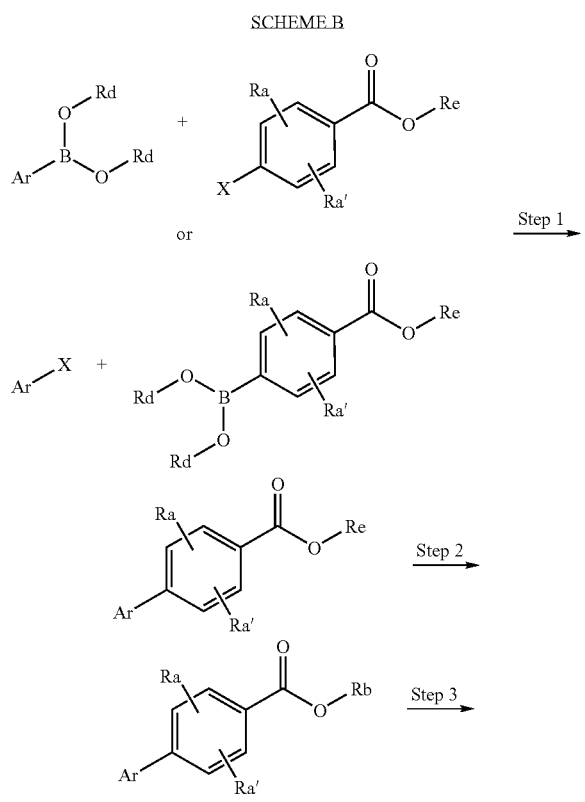

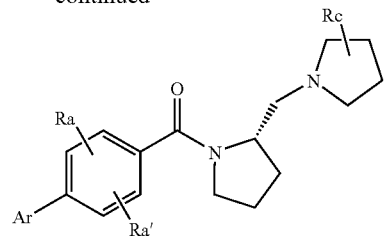

In Scheme B, $R_a$, $R_{a'}$, $R_b$, $R_c$, and Ar are as defined previously. $R_d$ can be H, alkyl or cycloalkyl; $R_e$ can be and is not limited to H or the corresponding Me, Et, Bz esters. In Scheme B (step 1), benzoic esters or acids (wherein $R_e$=Me, Et, H) substituted with halogen X, where X can be Cl, Br, or I combined with an aryl boronic acid (wherein $R_d$=H) or ester (wherein $R_d$=pinacol) are converted to the corresponding biaryls. Alternatively, in Scheme B (step 1), aryl chlorides, bromides or iodides can be combined with benzoic acid or ester substituted boronates (wherein $R_d$=pinacol) or boronic acids (wherein $R_d$=H) to give the corresponding biaryls. Both routes to these biaryls can be achieved by a variety of palladium catalyzed Suzuki reaction methods as described in Section IV-14 of the following review (Has san, Jwanro; Sevignon, Marc; Gozzi, Christel; Schulz, Emmanuelle; Lemaire, Marc; Aryl-Aryl Bond Formation One Century after the Discovery of the Ullmann Reaction. Chemical Reviews (Washington, D.C.) (2002), 102(5), 1359-1469). For example, 1-(6-chloro-pyridin-3-yl)-ethanone and 4-methoxycarbonylphenyl boronic acid are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc., is added followed by a suitable base such as aqueous sodium or potassium carbonate, anhydrous cesium or potassium fluoride, anhydrous potassium or cesium carbonate etc. The reaction is heated within a temperature range of 70 to 100° C. for a period of 4 to 24 hours. The reaction is concentrated and purified according to techniques well known in the art.

Alternatively, the biaryl formation (step 1) can also be performed using microwave assisted Suzuki couplings. For example, pyridine 3-boronic acid and 4-bromobenzoate are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc., is added followed by a suitable base such as aqueous sodium or potassium carbonate, anhydrous cesium or potassium fluoride, anhydrous potassium or cesium carbonate etc. The reaction is run in a CEM or MARS microwave reactor for 10 to 40 minutes, at 90 to 120° C., with 75 W power and cooling control on to maintain temperature range the reaction is concentrated and purified according to techniques well known in the art.

In Scheme B, Step 2, the resulting esters (wherein $R_e$=Me, Et, Bz etc.), can be saponified using standard conditions to yield the corresponding biaryl carboxylic acids or the lithium, sodium or potassium salt of the acid where $R_b$ can be H, Li, Na or K. For example, 4-pyridin-3-yl-benzoic acid methyl ester is dissolved in a suitable solvent such as MeOH or dioxane and 1M NaOH is added. The reaction mixture is stirred at room temperature overnight or can be heated to 50° C. for 30 min to 18 hours. The solvent is removed in vacuo and the acid or salt isolated according to techniques well known in the art.

In Scheme B (step 3), the carboxylic acids or the corresponding lithium, sodium or potassium salts (wherein $R_b$=H, Li, Na, K are converted to the pyrrolidinylmethylpyrrolidine amides by the methods described in Scheme A (step 1).

SCHEME C

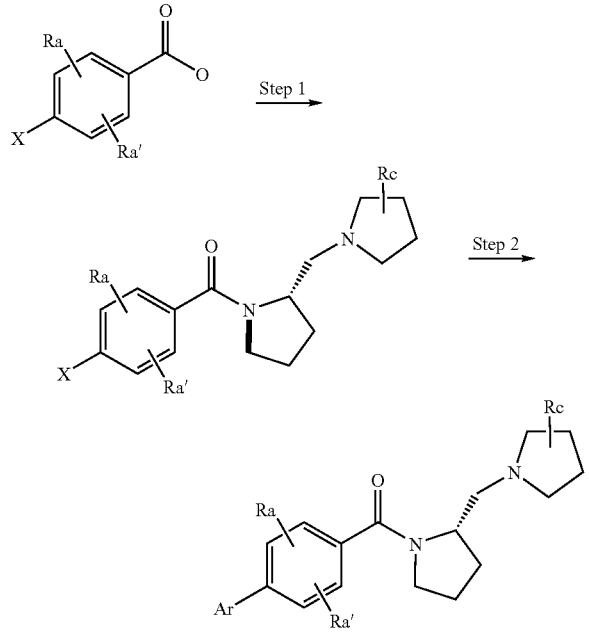

In Scheme c, $R_a$, $R_{a'}$, $R_c$, Ar and X are as defined previously. In Scheme C (step 1), the carboxylic acids are converted to the pyrrolidinylmethylpyrrolidine amides by the methods described in Scheme A (step 1).

For example, 4-bromobenzoic acid-2,5-dioxo-pyrrolidin-1-yl ester (3.5 g, 11.7 mmol), [which can be prepared from 4-bromobenzoic acid and N-hydroxy succinamide by standard conditions (C. Mitsos, Chem Pharm Bull 48(2), 211-214 (2000)] in a suitable solvent such as tetrahydrofuran, is added a suitable amine in this case (S)-(+)-1-(2-pyrrolidinylmethyl) pyrrolidine and the reaction mixture is heated to reflux for a period of 1-12 hours. The reaction is concentrated and purified according to techniques well known in the art.

In Scheme C (step 2) these biaryls can be achieved by a variety of palladium catalyzed Suzuki reaction methods as described under Scheme B. For example, (4-bromo-phenyl)-(2-(S)-pyrrolidin-1-ylmethyl-pyrrolidin-yl)methanone and 4-methylsulfonylphenyl boronic acid are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc., is added followed by a suitable base such as aqueous sodium or potassium carbonate, anhydrous cesium or potassium fluoride, anhydrous potassium or cesium carbonate etc. The reaction is heated within a temperature range of 70 to 100° C. for a period of 4 to 24 hours. The reaction is concentrated and purified according to techniques well known in the art.

Alternatively, the biaryl formation Scheme C (step 2) can also be performed using microwave assisted Suzuki couplings. For example, (4-bromo-2-fluoro-phenyl)-(2-(S)-pyrrolidin-1-ylmethyl-pyrrolidin-yl)methanone (wherein $R_a$=F) and 4-methanesulfonylphenyl boronic acid are placed in a microwave reactor vessel and dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc., is added followed by a suitable base such as aqueous sodium or potassium carbonate, anhydrous cesium or potassium fluoride, anhydrous potassium or cesium carbonate etc. The reaction is run in a CEM or MARS microwave reactor for 10 to 40 minutes, at 90 to 110° C., with 75 W power and cooling control on to maintain temperature range. The reaction is concentrated and purified according to techniques well known in the art.

SCHEME D

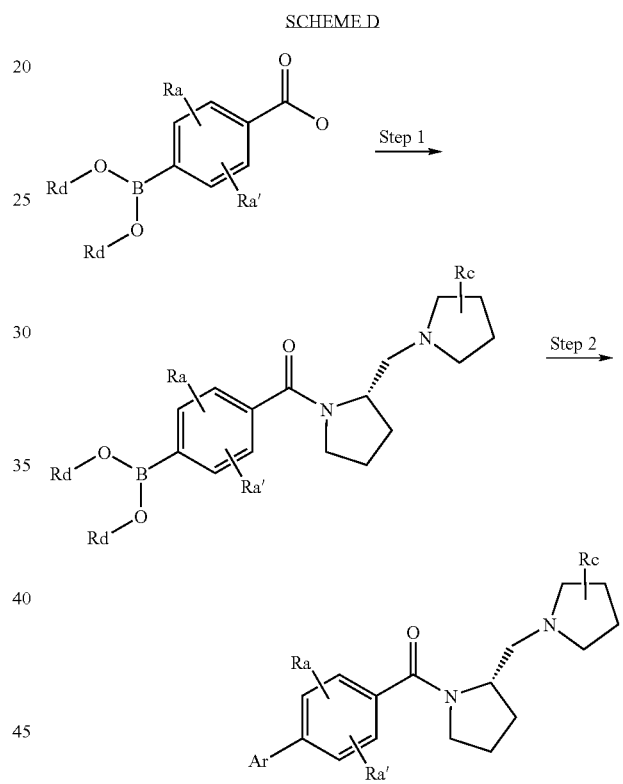

In Scheme D, $R_a$, $R_{a'}$, $R_c$, and $R_d$ and Ar are as previously defined. In Scheme D (step1), pyrrolidinylmethylpyrrolidine amides of commercially available (aldrich) 4-(4,4,5,5-Tetramethyl-[1,3,2]dioxaborolan-2-yl)-benzoic acid can be prepared by the method of Kaminski (Tetrahedron Lett., 26, 2901-2904, 1985). For example, 4-(4,4,5,5-Tetramethyl-[1,3,2]dioxaborolan-2-yl)-benzoic acid is dissolved in a suitable solvent such as $CH_2Cl_2$, acetonitrile, THF, or mixtures thereof. A suitable base such as n-methylmorpholine, triethylamine, diisopropylethylamine etc., is added at 0° C. to ambient temperature, followed by 2-chloro-4,6-dimethoxy-1,3,5-triazene and stirred for 20 to 45 minutes. To the reaction mixture is then added (S)(+)-1-(2-pyrrolidinylmethyl)pyrrolidine and the reaction is stirred at ambient temperature for 2 to 6 hours. The reaction mixture is washed with aqueous sodium bicarbonate and purified according to techniques well known in the art.

In Scheme D (step 2) the boronic ester formed in Scheme D (step 1) can be converted to a biaryl using the Suzuki coupling methods described in Schemes B and C. For example, (2-Pyrrolidin-1-ylmethyl-pyrrolidin-1-yl)-[4-(4,4,5,5-tetramethyl-[1,3,2]dioxaborolan-2-yl)-phenyl]-methanone and 5-iodopyridin-2-ylamine are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc., is added followed by a suitable base such as aqueous sodium or potassium carbonate, anhydrous cesium or potassium fluoride, anhydrous potassium or cesium carbonate etc. The reaction is run in a CEM or MARS microwave reactor for 10 to 40 minutes, at 90 to 120° C., with 75 W power and cooling control on to maintain temperature range. The reaction is concentrated and purified according to techniques well known in the art.

SCHEME E

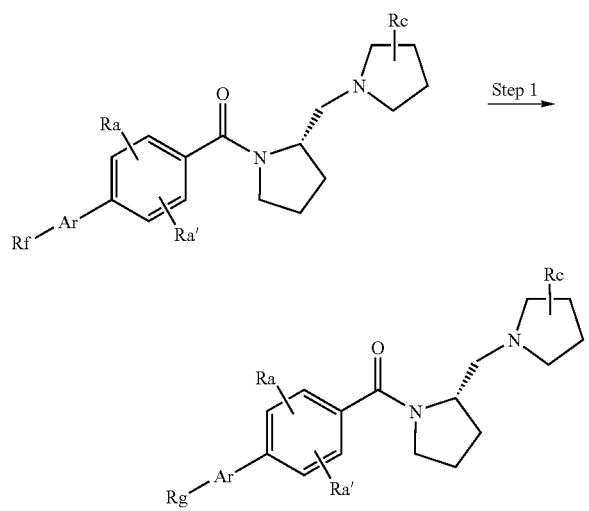

In Scheme E, $R_a$, $R_{a'}$, $R_c$, are as previously defined. $R_f$ is any functional group that can be further modified to $R_g$ via alkylation, acylation, oxidation, reduction, sulfonylation etc. In Scheme E (step 1), wherein $R_f$=amino, $R_f$ can be converted to a sulfonamide using known sulfonylating conditions. For example, [4-(6-amino-pyridin-3-yl)-phenyl]-(2-(S)-pyrrolidin-1-ylmethyl-pyrrolidin-1-yl)-methanone is dissolved in a suitable solvent such as $CH_2Cl_2$, acetonitrile, or mixtures thereof in combination with 20 to 50% pyridine by volume. To the reaction mixture is added a suitable sulfonylating reagent such as methane, ethane, or phenylsulfonyl chloride and stirred at ambient temperature for a period of 24 to 48 hours. The reaction is concentrated and purified according to techniques well known in the art.

SCHEME F

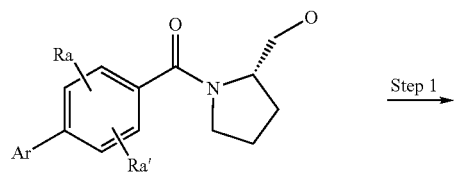

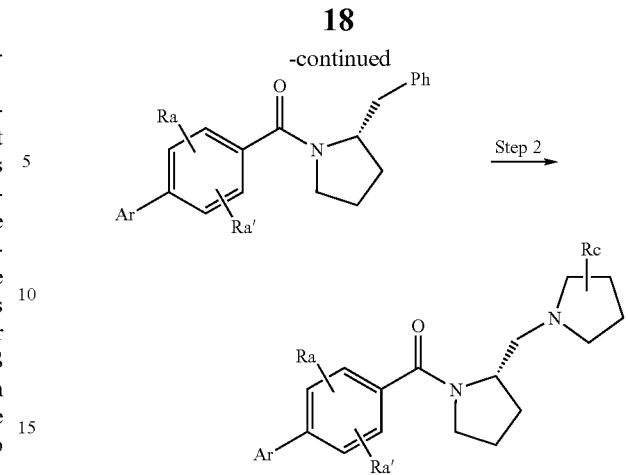

In Scheme F, $R_a$, $R_{a'}$, $R_c$ and Ar are as previously defined. In Scheme F, Step 1, the alcohol can be converted to a leaving group i.e. mesylate, tosylate, iodide (wherein $R_h$=OMs, OTs, I) etc., using standard literature procedures. For example, a mixture of (2-(S)-hydroxymethyl-pyrrolidin-1-yl)-(4'-trifluoromethyl-biphenyl-4-yl)-methanone (wherein Ar=4-trifluorophenyl) and a suitable base in this case triethylamine in an aprotic solvent such as dichloromethane is cooled to 0° C. and treated with methanesulfonyl chloride. The mixture is allowed to stir at room temperature for 2 to 8 h. The reaction is concentrated and purified according to techniques well known in the art or used crude in the next reaction.

In step 2, this activated alcohol is treated with excess amine in a suitable solvent to provide the desired amines. For example, the crude methanesulfonic acid 1-(4'-trifluoromethyl-biphenyl-4-carbonyl)-pyrrolidin-2-ylmethyl ester (wherein Ar=4-trifluorophenyl) is dissolved in a suitable solvent such as THF and 2-10 equivalents of methylpyrrolidine (wherein $R_c$=Me) is added. The mixture is stirred at room temperature or heated for a period of 8 to 48 h at 70° C. The reaction is concentrated and purified according to techniques well known in the art.

A further embodiment of the invention are any novel intermediate preparations described herein which are useful for preparing the histamine H3 receptor antagonists or inverse agonists of formula I, or II, or X1 to X115.

Intermediate Preparation 1

4'-trifluoromethyl-biphenyl-4-carboxylic acid methyl ester

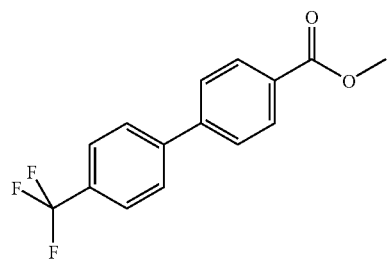

Procedure A': A suspension of 4-(trifluoromethyl)phenylboronic acid (7.3 g, 38.4 mmol), methyl 4-bromobenzoate (7.44 g, 36.4 mmol), triphenylphosphine (1.21 g, 4.6 mmol), cesium fluoride (11.7 g, 76.8 mmol) and palladium acetate (0.26 g, 1.15 mmol) in degassed DME and methanol is heated at reflux for 24 h. The suspension is cooled to room temperature, filtered, and the resulting filtrate concentrated in vacuo to give a dark solid. This material is taken up in acetone and adsorbed on silica gel, and purified by flash filtration using 500 mL each of 2% to 20% ethyl acetate/hexanes in 2% increments. Fractions containing the product are combined to give the title compound in 92% yield. NMR (CDCl$_3$) 8.10 (d, J=8.4 Hz, 2H), 7.99 (d, J=7.9 Hz, 2H), 7.92 (d, J=8.4 Hz, 2H), 7.83 (d, 8.4 Hz, 2H), 3.58 (s, 3H).

Intermediate Preparation 2

4'-Trifluoromethyl-biphenyl-4-carboxylic acid, lithium salt

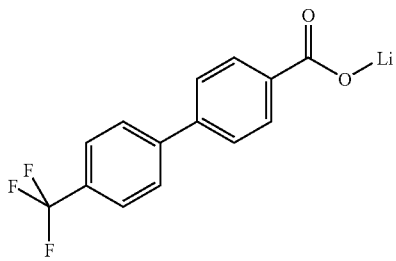

4'-Trifluoromethyl-biphenyl-4-carboxylic acid methyl ester (8.9 g, 31.8 mmol) is dissolved in dioxane (300 mL) and lithium hydroxide monohydrate (1.46 g, 34.9 mmol), followed by water (75 mL) is added. The reaction is sonicated to dissolve the lithium hydroxide, and the reaction mixture is stirred at room temperature overnight. The solvent is removed in vacuo to give the title compound (8.8 g, 100%). MS (ES−) 265.1

Example 1

(2-(S)-Pyrrolidin-1-ylmethyl-pyrrolidin-1-yl)-(4'-trifluoromethyl-biphenyl-4-yl)-methanone

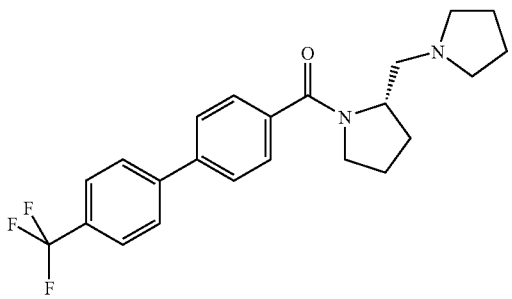

Procedure B': 4'-Trifluoromethyl-biphenyl-4-carboxylic acid (2.7 g, 10.1 mmol) is suspended in dichloromethane (100 mL) and DMF (100 mL). EDC (2.33 g, 12.2 mmol) and HOBt (1.64 g, 12.2 mmol) were added at room temperature in that order. DIEA (4.4 mL, 25.3 mmol) and (S)(+)-1-(2-pyrrolidinylmethyl)pyrrolidine (1.56 g, 10.1 mmol) are added to the mixture. The mixture is stirred at room temperature for overnight. Water and ethyl acetate are added to the mixture. The aqueous layer is extracted with dichlormethane (2×), followed by ethyl acetate (2×). The combined organic layers are washed with brine (3×), dried over Na$_2$SO$_4$ and evaporated. The crude product is purified by silica-gel column chromatography (gradient: 100% CH$_2$Cl$_2$ to 10% 2M NH$_3$ in MeOH/CH$_2$Cl$_2$) give the product. MS (ES+) 403.2

Intermediate Preparation 3

2'-Trifluoromethyl-biphenyl-4-carboxylic acid

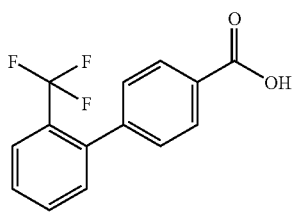

Procedure C': 2'-trifluoromethyl-biphenyl-4-carbaldehyde (Array 4PNL-S04-0) (0.63 g, 2.5 mmol) is suspended in formic acid (3.5 mL), and the solution is placed in an ice bath. Hydrogen peroxide is added (0.875 mL, 7.5 mmol), and the reaction vessel is placed in the refrigerator and is allowed to stand for 1-2 days. The yellow solid that precipitates out is filtered, washed with cold water and dried in a vacuum oven to give the title compound (0.45 g, 69%). MS (ES−) 265.1

Example 2

(2-(S)-Pyrrolidin-1-ylmethyl-pyrrolidin-1-yl)-(2'-trifluoromethyl-biphenyl-4-yl)-methanone

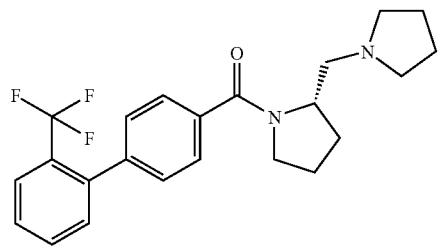

The title compound is prepared in a manner substantially analogous to Procedure B' from 2'-trifluoromethyl-biphenyl-4-carboxylic acid. MS (ES+) 403.2

Example 3

(4'-Chloro-biphenyl-4-yl)-(2-(S)-pyrrolidin-1-ylmethyl-pyrrolidin-1-yl)-methanone

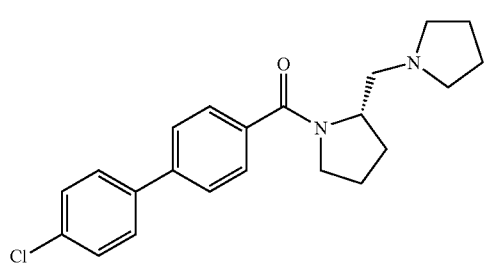

The title compound is prepared in a manner substantially analogous to Procedure C' & B' from 4'-chloro-biphenyl-4-carbaldehyde (Array 4PNL-Q02-0). MS (ES+) 369.2

Example 4

(2'-Chloro-biphenyl-4-yl)-(2-(S)-pyrrolidin-1-ylmethyl-pyrrolidin-1-yl)-methanone

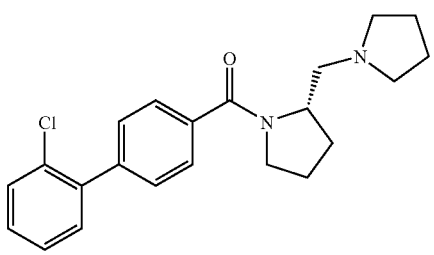

The title compound is prepared in a manner substantially analogous to Procedure C' & B' from 2'-chloro-biphenyl-4-carbaldehyde (Array 4PNL-S02-0). MS (ES+) 369.2

Example 5

[4-(6-Methyl-pyridin-2-yl)-phenyl]-(2-(S)-pyrrolidin-1-ylmethyl-pyrrolidin-1-yl)-methanone

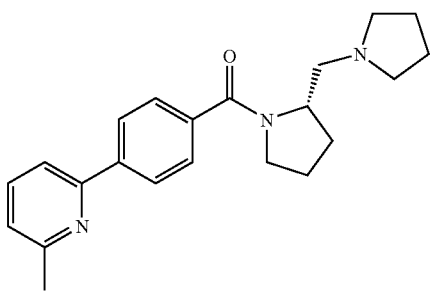

The title compound is prepared in a manner substantially analogous to Procedure B' from 4-(6-methyl-2-pyridinyl)-benzoic acid [CAS 582325-11-9]. MS (ES+) 350.2

Example 6

[4'-(5-Methyl-[1,3,4]oxadiazol-2-yl)-biphenyl-4-yl]-(2-pyrrolidin-1-ylmethyl-pyrrolidin-1-yl)-methanone

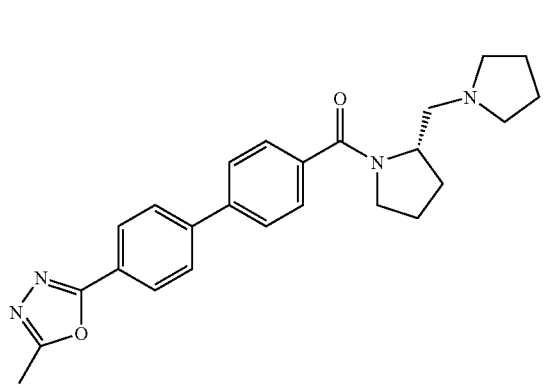

Procedure D': To a microwave reactor vessel, add 2-(4-Chloro-phenyl)-5-methyl-[1,3,4]oxadiazole (1.0 mmol; CAS (22815-98-1), (2-(S)-Pyrrolidin-1-ylmethyl-pyrrolidin-1-yl)-[4-(4,4,5,5-tetramethyl-[1,3,2]dioxaborolan-2-yl)-phenyl]-methanone (See Intermediate Preparation 23) (2.5 mmol), palladium (II) acetate (0.025 mmol), tricyclohexylphosphine (0.05 mmol), potassium carbonate (5.0 mmol) and ethanol (0.10M). Run the reaction in a CEM microwave reactor for four hours at 90° C. with 80 W power and cooling. After this time, wash the reaction with 1N hydrochloric acid while extracting with dichloromethane. Dry the organics with sodium sulfate, decant and concentrate in vacuo. Purify the title compound via radial chromatography eluting with 2M ammonia in methanol and dichloromethane. MS (m/e): 417.3 (M+1)

Example 7

(3-Fluoro-biphenyl-4-yl)-(2-(S)-pyrrolidin-1-ylmethyl-pyrrolidin-1-yl)-methanone trifluoroacetate

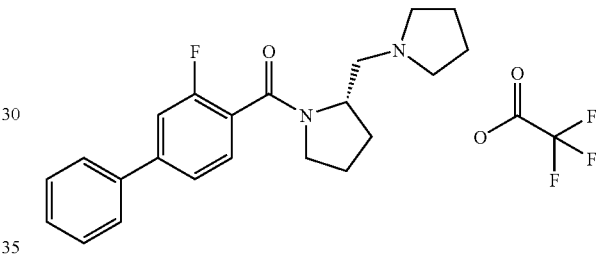

The title compound is prepared in a manner substantially analogous to Procedure B' from 3-fluoro-[1,1'-Biphenyl]-4-carboxylic acid [CAS 505082-76-8] and purified by reverse phase chromatography to give the trifluoroacetate salt. MS (ES+) 353.4

Example 8

(3,2'-Difluoro-biphenyl-4-yl)-(2-(S)-pyrrolidin-1-ylmethyl-pyrrolidin-1-yl)-methanone trifluoroacetate

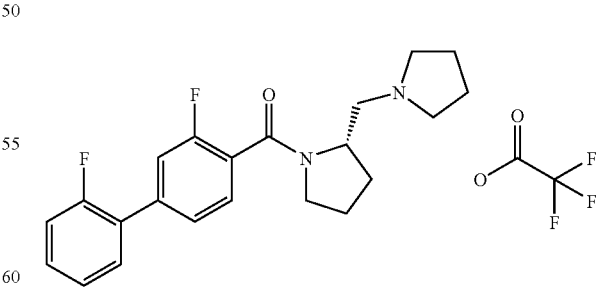

The title compound is prepared in a manner substantially analogous to Procedure B' from 2',3-difluoro-[1,1'-Biphenyl]-4-carboxylic acid [CAS 505082-83-7] and purified by reverse phase chromatography to give the trifluoroacetate salt. MS (ES+) 371.4

Example 9

(2'-Fluoro-biphenyl-4-yl)-(2-(S)-pyrrolidin-1-ylm-ethyl-pyrrolidin-1-yl)-methanone trifluoroacetate

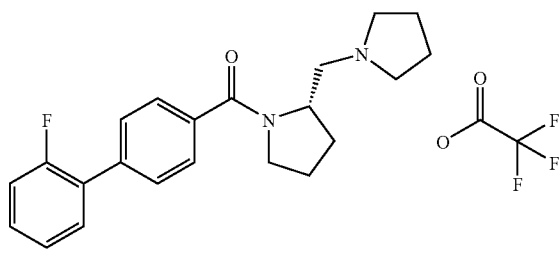

The title compound is prepared in a manner substantially analogous to Procedure B' from 2'-difluoro-[1,1'-Biphenyl]-4-carboxylic acid [CAS 365-12-8] and purified by reverse phase chromatography to give the trifluoroacetate salt. MS (ES+) 353.4

Example 10

(4'-Fluoro-biphenyl-4-yl)-(2-(S)-pyrrolidin-1-ylm-ethyl-pyrrolidin-1-yl)-methanone trifluoroacetate

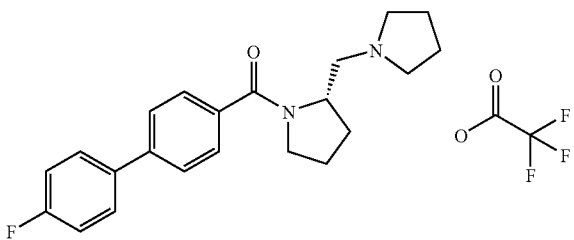

The title compound is prepared in a manner substantially analogous to Procedure B' from 4'-difluoro-[1,1'-Biphenyl]-4-carboxylic acid [CAS 5731-10-2] and purified by reverse phase chromatography to give the trifluoroacetate salt. MS (ES+) 353.2

Example 11

(2S-Pyrrolidin-1-ylmethyl-pyrrolidin-1-yl)-(3'-chloro-biphenyl-4-yl)-methanone

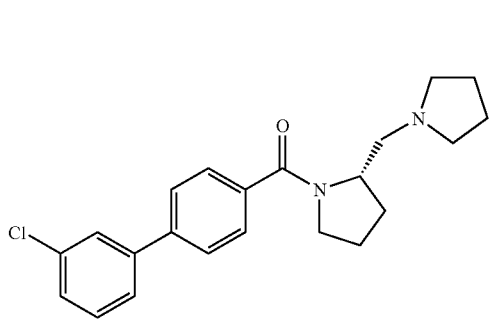

Procedure E': 3'-Chloro-biphenyl-4-carboxylic acid (CAS 5728-43-8) (0.5 g, 2.15 mmol) is dissolved in dimethylfor-mamide (8 ml) with stirring at room temperature. TBTU (0.69 g, 2.15 mmol), triethylamine (1 ml) and (S)(+)-1-(2-pyrro-lidinylmethyl)pyrrolidine (0.33 g, 2.15 mmol) are added and this mixture is stirred at room temperature overnight. Water and ethyl acetate are added to the mixture. The aqueous layer is extracted several times with ethyl acetate. The combined organic layers are dried over $MgSO_4$ and evaporated. The crude product is purified by silica-gel column chromatography (gradient: 100% $CH_2Cl_2$ to 10% 2M $NH_3$ in MeOH/$CH_2Cl_2$) give the title compound. MS (FLA) 369/371 (MH$^+$)

Example 12

(2S-Pyrrolidin-1-ylmethyl-pyrrolidin-1-yl)-(3'-trif-luoromethyl-biphenyl-4-yl)-methanone

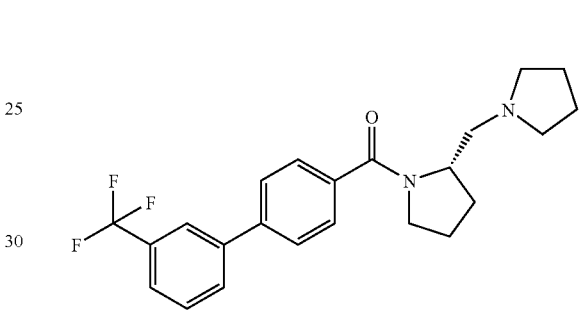

The title compound is prepared in a manner substantially analogous to Procedure E' from 3'-trifluoromethyl-biphenyl-4-carboxylic acid (CAS 195457-70-6). MS (FIA) 403.1 (MH$^+$)

Example 13

(4-Pyrimidin-5-yl-phenyl)-(2S-pyrrolidin-1-ylm-ethyl-pyrrolidin-1-yl)-methanone

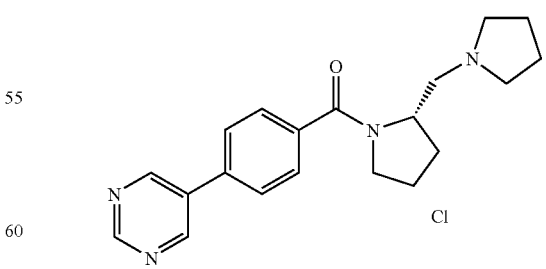

The title compound is prepared in a manner substantially analogous to Procedure E' from 4-pyrimidin-5-yl-benzoic acid (CAS 216959-91-0). MS (FIA) 337.4 (MH$^+$)

Example 14

(2S-Pyrrolidin-1-ylmethyl-pyrrolidin-1-yl)-[4-(6-trifluoromethyl-pyridin-3-yl)]-methanone

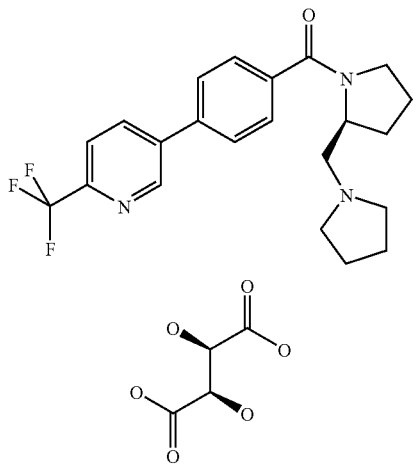

Procedure F': 5-Bromo-2-trifluoromethylpyridine (Eur J. Org Chem (2003), 1559) (0.85 g, 3.7 mmol), methoxycarbonylphenyl-4-boronic acid (0.44 g, 2.4 mmol) and sodium carbonate (1 g, 9.4 mmol) are suspended in dioxane/water (9:1) (25 ml). The mixture is degassed for 20 minutes with a nitrogen stream, tetrakis(triphenylphosphine) palladium (0.05 g, 0.04 mmol) is added and the mixture is heated to reflux under nitrogen overnight. The mixture is concentrated under reduced pressure and partitioned between water and ethyl acetate. The aqueous layer is extracted several times with ethyl acetate. The combined organic layers are dried over MgSO$_4$ and evaporated. The crude product is purified by silica-gel column chromatography (gradient 10% ethyl acetate in cyclohexane to 10% cyclohexane in ethyl acetate) to give 4-(6-trifluoromethyl-pyridin-3-yl)-benzoic acid methyl ester. MS (FIA) 282.0 (MH$^+$).

Procedure G': 4-(6-Trifluoromethyl-pyridin-3-yl)-benzoic acid methyl ester (0.57 g, 2 mmol) is dissolved in tetrahydrofuran/water (9:1) (25 ml), lithium hydroxide monohydrate (0.9 g, 2.2 mmol) is added and the mixture is heated under reflux overnight. The mixture is concentrated under reduced pressure and partitioned between water and ethyl acetate. The aqueous layer is acidified and the resulting precipitate is collected by filtration to give the 4-(6-trifluoromethyl-pyridin-3-yl)-benzoic acid. MS (FIA) 267 (MH$^-$)

(2S-Pyrrolidin-1-ylmethyl-pyrrolidin-1-yl)-[4-(6-trifluoromethyl-pyridin-3-yl)]-methanone is prepared in a manner substantially analogous to Procedure E' from 4-(6-trifluoromethyl-pyridin-3-yl)-benzoic acid. MS (FIA) 404.5 (MH$^+$). This product was dissolved in methanol, L-tartaric acid (1 equivalent) was added and the mixture was heated to dissolve all solids. The solvent was removed under reduced pressure and the resulting sticky solid was recrystallised from 2-propanol and then filtered to collect the salt.

Example 15

(3-Chloro-4'-methanesulfonyl-biphenyl-4-yl)-(2S-pyrrolidin-1-ylmethyl-pyrrolidin-1-yl)-methanone

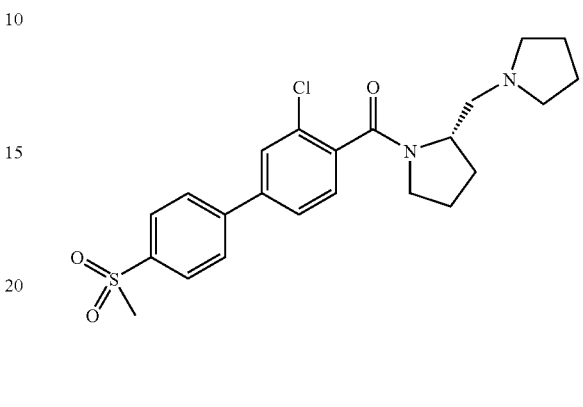

The title compound is prepared in a manner substantially analogous to Example 14 via Procedures F', G' & E' from 2-chloro-4-bromobenzoic acid methyl ester (CAS 185312-82-7) and 4-methanesulfonylbenzene boronic acid (CAS 149104-88-1). MS (FIA) 447/449 (MH$^+$)

Intermediate Preparation 4

4-Pyridin-3-yl-benzoic acid methyl ester

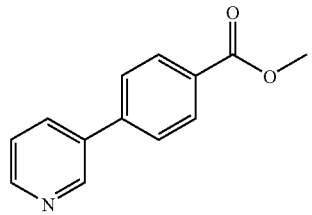

Procedure H': 750 mg of pyridine-3-boronic acid (6.14 mmol), 1.34 g of methyl 4-bromobenzoate (6.22 mmol) are put in the reaction vessel with 25 ml of DME:water:EtOH=7:3:2.). 6.25 ml of aqueous 2M Na$_2$CO$_3$ is added to the mixture and 250 mg of tetrakis(triphenylphosphine is added. The vessel is sealed and heated at 110° C. for 40 min in Microwave machine (MARS). After cooling, water and CH$_2$Cl$_2$ are added. The CH$_2$Cl$_2$ layer is separated, washed by brine, dried over Na$_2$SO$_4$ and evaporated. The crude product is applied to silica-gel column chromatography (Hexane:AcOEt=3:1) to give 4-pyridin-3-yl-benzoic methyl ester. Yield 50%: mass spectrum (m/e): 214 (M+1); 1H-NMR (CDCl3): 8.92 (m, 1H), 8.68 (m, 1H), 8.18 (d, 2H, J=7.6 Hz), 7.95 (m, 1H), 7.69 (d, 2H, J=7.6 Hz), 7.43 (m, 1H), 3.99 (s, 3H).

Intermediate Preparation 5

4'-Cyclopropanecarbonyl-biphenyl-4-carboxylic acid methyl ester

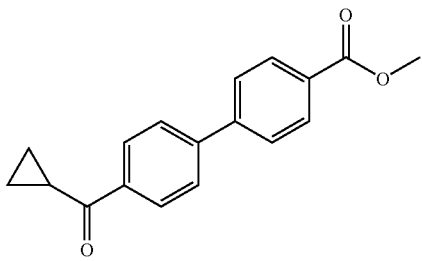

Procedure I': 1.8 g of (4-bromophenyl)cyclopropylmethane (8.0 mmol), 1.80 g of (4-methoxycarbonylphenyl)boronic acid (10.0 mmol) are put into flask with 8.0 ml of aqueous 2M $K_2CO_3$ and 90 ml of toluene:EtOH=20:1. The mixture is deoxygenated and stirred at room temperature under $N_2$ for 30 min. 280 mg of tetrakis(triphenylphosphine)-palladium is added. The reaction mixture is stirred under reflux for overnight. Organic layer is separated from water layer and water layer is extracted with $CH_2Cl_2$. All organic layers are combined together and dried over $Na_2SO_4$ and evaporated. The crude product is applied to silica-gel column chromatography (Hexane:AcOEt=8:1→3:1). 4'-Cyclopropanecarbonyl-biphenyl-4-carboxylic acid methyl ester is recrystallized from hexane/AcOEt (849 mg, 38%). Mass spectrum (m/e): 214 (M+1)

Intermediate Preparation 6

4-Pyridin-3-yl-benzoic acid

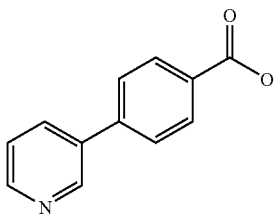

Procedure J': 648 mg of 4-Pyridin-3-yl-benzoic acid methyl ester (3.04 mmol) is dissolved in 15 ml of MeOH and 10 ml of 1N NaOH is added. The reaction mixture is stirred at 50° C. for 30 min and room temperature for overnight. MeOH is removed in vacuo and the residue is acidified to pH=4.0 by 1N HCl. Crystals are filtered and washed by water and dried to give 578 mg of 4-pyridin-3-yl-benzoic acid (96%). 1H-NMR (DMSO): 13.1 (br, 1H), 8.98 (m, 1H), 8.64 (m, 1H), 8.17 (m, 1H), 8.07 (d, 2H, J=8.0 Hz), 7.89 (d, 2H, J=8.0 Hz), 7.57 (m, 1H).

Intermediate Preparation 7

4'-Cyclopropanecarbonyl-biphenyl-4-carboxylic acid

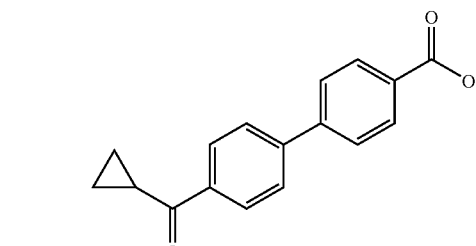

4'-Cyclopropanecarbonyl-biphenyl-4-carboxylic acid is prepared in a manner substantially analogous to Procedure J' from the corresponding methyl ester. 1H-NMR (DMSO): 13.0 (br, 1H), 8.14 (d, 2H, J=8.5 Hz), 8.04 (d, 2H, J=8.8 Hz), 7.90 (d, 2H, J=8.8 Hz), 7.89 (d, 2H, J=8.8 Hz), 2.94 (m, 1H), 1.06 (m, 4H).

Example 16

(4-Pyridin-3-yl-phenyl)-(2S-pyrrolidin-1-ylmethyl-pyrrolidin-1-yl)-methanone

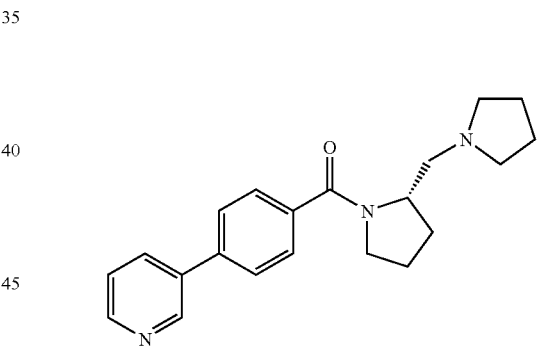

Procedure K': 377 mg of 4-pyridin-3-yl-benzoic acid (1.89 mmol), 433 mg of EDCI (2.27 mmol), 306 mg of HOBt (2.27 mmol) are put into 20 ml of 10% DMF in $CH_2Cl_2$. 610 mg of DIEA (4.73 mmol) and 292 mg of (S)(+)-1-(2-pyrrolidinyl-methyl)pyrrolidine (1.89 mmol) are added to the mixture. The mixture is stirred at room temperature for overnight. Water and $CH_2Cl_2$ are added to the mixture. The separated $CH_2Cl_2$ layer is dried over $Na_2SO_4$ and evaporated. The crude product is applied to silica-gel column chromatography ($CH_2Cl_2$:2M $NH_3$ in MeOH=20:1) to give the product (82%). The product is crystallized from $Et_2O$ for further purification (recovery yield 76%). mass spectrum (m/e): 336 (M+1); 1H-NMR (CDCl3): 8.88 (m, 1H), 8.65 (m, 1H), 7.92 (m, 1H), 7.61 (m, 4H), 7.42 (m, 1H), 4.50 (m, 1H), 3.52 (m, 2H), 2.92 (m, 1H), 2.64 (m, 3H), 2.04 (m, 4H), 1.82 (m, 4H), 1.67 (m, 2H).

Example 17

(4-Pyridin-2-yl-phenyl)-(2S-pyrrolidin-1-ylmethyl-pyrrolidin-1-yl)-methanone

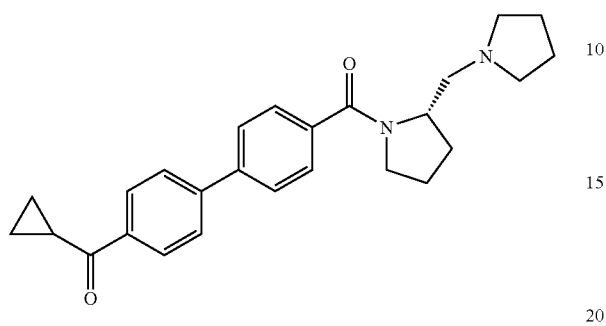

Procedure L': 317 mg of 4'-Cyclopropanecarbonyl-biphenyl-4-carboxylic acid (1.19 mmol) is dissolved in 10 ml of thionyl chloride and stirred under reflux for 1 h and excess thionyl chloride is removed in vacuo. The residue is dissolved in 1 ml of $CH_2Cl_2$ to make acid chloride solution. 275 mg of (S)(+)-1-(2-pyrrolidinylmethyl)pyrrolidine (1.mmol) and 182 mg of triethylamine are dissolved in 3 ml of $CH_2Cl_2$ and acid chloride solution is added. The reaction mixture is stirred at room temperature for 1 h. The reaction mixture is concentrated and applied to silica-gel column chromatography ($CH_2Cl_2$:2M $NH_3$ in MeOH=20:1) to give the title compound. 287 mg, yield 66%. Mass spectrum (m/e): 403 (M+1)

Example 18

4'-(2S-Pyrrolidin-1-ylmethyl-pyrrolidine-1-carbonyl)-biphenyl-4-carbonitrile

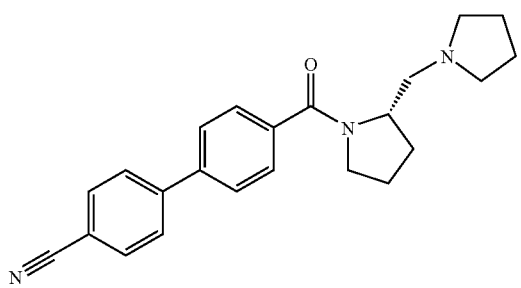

Procedure M': 223 mg of 4'-cyano[1,1'-biphenyl]-4-carboxylic acid (CAS 5728-46-1) (1.0 mmol) and 185 mg of (S)(+)-1-(2-pyrrolidinylmethyl)pyrrolidine (1.2 mmol) and 909 mg of PS-carbodiimide (1.2 mmol) are placed into a 10 ml vial with 8.9 ml of 10% DMF in $CH_2Cl_2$. The vial is capped with a teflon cap and shaken at room temperature for overnight. The reaction mixture is filtered, concentrated and applied to silica-gel column chromatography ($CH_2Cl_2$:2M $NH_3$ in MeOH=20:1) to give the title compound. 65 mg. Yield 18%; mass spectrum (m/e): 360 (M+1).

Example 19

(4-Pyridin-2-yl-phenyl)-(2S-pyrrolidin-1-ylmethyl-pyrrolidin-1-yl)-methanone

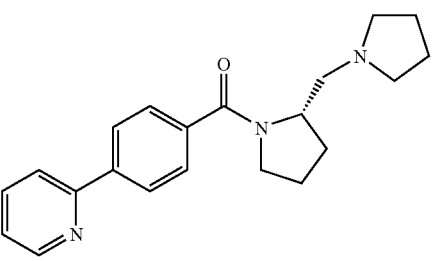

Procedure N': 185 mg of (S)(+)-1-(2-pyrrolidinylmethyl)pyrrolidine (1.2 mmol) is dissolved in 2.0 ml of THF and 0.6 ml of trimethylaluminum (2.0M solution in toluene, 1.2 mmol) is added. The reaction mixture is stirred at room temperature for 20 min. 213 mg of 4-pyridin-2-yl-benzoic acid methyl ester (CAS 98061-21-3) (1.0 mmol) in 2.0 ml of THF is added to the mixture and stirred at room temperature for 4 days. Water and $CH_2Cl_2$ are added and $CH_2Cl_2$ layer is separated, dried over $Na_2SO_4$ and evaporated. The crude product is applied to silica-gel column chromatography ($CH_2Cl_2$:2M $NH_3$ in MeOH=20:1) to give the title compound. 295 mg. Yield 88%; mass spectrum (m/e): 336 (M+1)

Example 20

(4-Pyridin-4-yl-phenyl)-(2S-pyrrolidin-1-ylmethyl-pyrrolidin-1-yl)-methanone

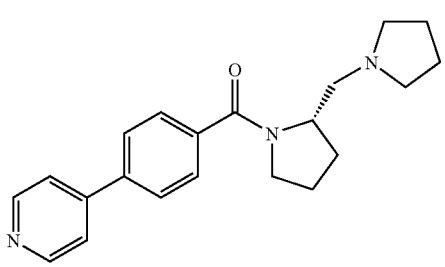

(4-Pyridin-4-yl-phenyl)-(2S-pyrrolidin-1-ylmethyl-pyrrolidin-1-yl)-methanone is prepared in a manner substantially analogous to Procedure H', J' and K'. Mass spectrum (m/e): 336 (M+1)

Example 21

4'-(2S-Pyrrolidin-1-ylmethyl-pyrrolidine-1-carbonyl)-biphenyl-4-sulfonic acid dimethylamide

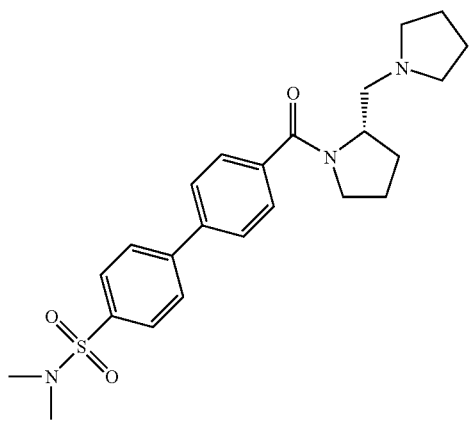

Procedure O': A 10-12 mL MeCN solution of N,N-dimethyl-4-(4,4,5,5-tetramethyl-[1,3,2]dioxaborolan-2-yl)-benzenesulfonamide (CAS 486422-04-2) (349 mg, 1.12 mmol) and (4-bromo-phenyl)-(2-(S)-pyrrolidin-1-ylmethyl-pyrrolidin-1-yl)-methanone (337 mg, 1.0 mmol) is degassed (vacuum/$N_2$ purge 3×), then the tricyclohexylphosphine (85 mg, 0.3 mmol), the Pd(OAc)$_2$ (79 mg, 0.35 mmol), and CsF (529 mg, 3.5 mmol) are added. The reaction mixture is stirred under $N_2$ at reflux until the bromide starting material is consumed (usually three to six hours). Reaction mixture is allowed to cool, is filtered through Celite and is concentrated. The crude residue is purified by SCX chromatography (MeOH wash, then elution with 2M $NH_3$/MeOH to give partially purified material. This material is then purified by silica-gel column chromatography (gradient: 100% $CH_2Cl_2$ to 10% 2M $NH_3$ in MeOH/$CH_2Cl_2$) to give the title compound (100 mg, 23% yield). MS (ES+) 442.2 (M+H)$^+$

Intermediate Preparation 8

N-tert-Butyl-4-(4,4,5,5-tetramethyl-[1,3,2]dioxaborolan-2-yl)-benzenesulfonamide

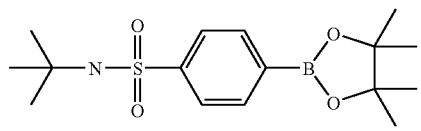

Procedure P': A 25 mL DMSO mixture of 4-bromo-N-tert-butyl-benzenesulfonamide (CAS 93281-65-3) (2000 mg, 6.84 mmol), bis(pinacolato)diboron (2090 mg, 8.21 mmol), [1,1 bis(diphenylphosphino)ferrocene]dichloropalladium(II) complex with $CH_2Cl_2$ (1:1) (175 mg, 240 mmol), and KOAc (2020 mg, 20.5 mmol) is stirred under $N_2$ at 90° C. for 7.5 hours. Reaction mixture is allowed to cool, is diluted with $H_2O$ and is extracted with $CH_2Cl_2$. The $CH_2Cl_2$ extract is washed with $H_2O$ and brine, dried (Na$_2$SO$_4$) and evaporated. The crude product is purified by silica-gel column chromatography (gradient: 100% $CH_2Cl_2$ to 5% EtOAc/$CH_2Cl_2$) give the intermediate N-tert-butyl-4-(4,4,5,5-tetramethyl-[1,3,2]dioxaborolan-2-yl)-benzenesulfonamide (2000 mg, 86% yield). (MS (ES−) 256 (boronic acid).

Example 22

4'-(2S-Pyrrolidin-1-ylmethyl-pyrrolidine-1-carbonyl)-biphenyl-4-sulfonic acid tert-butylamide

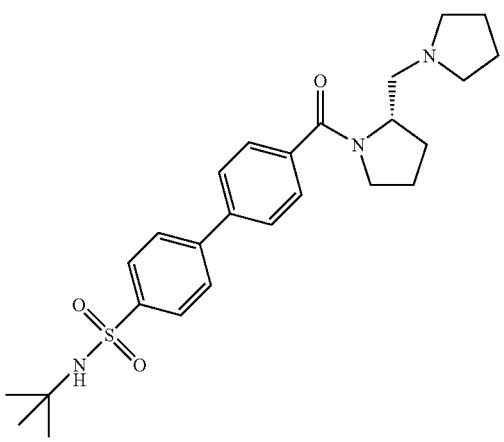

The title compound is prepared in a manner substantially analogous to Procedure O' using N-tert-butyl-4-(4,4,5,5-tetramethyl-[1,3,2]dioxaborolan-2-yl)-benzenesulfonamide) (373 mg, 1.10 mmol) and (4-bromo-phenyl)-(2-(S)-pyrrolidin-1-ylmethyl-pyrrolidin-1-yl)-methanone (337 mg, 1.0 mmol), tricyclohexylphosphine (85 mg, 0.3 mmol), Pd(OAc)$_2$ (79 mg, 0.35 mmol), and CsF (529 mg, 3.5 mmol) to give the title compound. (175 mg, 37% yield). MS (ES+) 470.2 (M+H)$^+$

Example 23

4'-(2S-Pyrrolidin-1-ylmethyl-pyrrolidine-1-carbonyl)-biphenyl-4-sulfonic acid amide

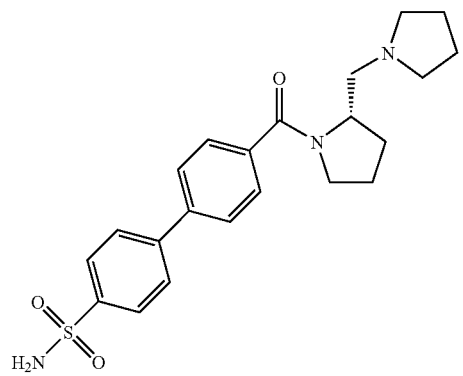

Procedure Q': A 1 mL $CH_2Cl_2$ solution of 4'-(2S-pyrrolidin-1-ylmethyl-pyrrolidine-1-carbonyl)-biphenyl-4-sulfonic acid tert-butylamide (141 mg, 0.30 mmol), anisole (0.33 mL, 3 mmol), and trifluoroacetic acid (1 mL, 13 mmol) are stirred at 50-60° C. under $N_2$ for 5-6 hours. Reaction mixture is allowed to cool and is concentrated. The crude residue is purified by SCX chromatography (MeOH wash, then elution with 2M NH₃/MeOH to give partially purified material. This material is then purified by silica-gel column chromatography (gradient: 100% CH₂Cl₂ to 10% 2M NH₃ in MeOH/CH₂Cl₂) to give the title compound (94 mg, 76% yield). MS (ES+) 414.2 (M+H)⁺

Intermediate Preparation 9

4-Bromo-N-tert-butyl-N-methyl-benzenesulfonamide

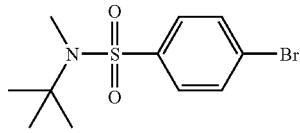

Procedure R': A 15 mL DMF mixture of 4-bromo-N-tert-butyl-benzenesulfonamide (1022 mg, 3.5 mmol), iodomethane (0.44 mL, 7 mmol), and K₂CO₃ (987 mg, 7 mmol) is stirred at room temperature overnight. Water and ethyl acetate are added to the mixture. The aqueous layer is extracted several times with ethyl acetate. The combined organic layers are washed with H₂O and brine, then dried over Na₂SO₄ and evaporated. The crude product is purified by silica-gel column chromatography (gradient: 100% CH₂Cl₂ to 20% EtOAc/CH₂Cl₂) give the intermediate 4-bromo-N-tert-butyl-N-methyl-benzenesulfonamide (1040 mg, 97% yield). MS (ES+) 251.9 (M-tBu)⁺, NMR (CDCl₃).

Intermediate Preparation 10

4'-(tert-Butyl-methyl-sulfamoyl)-biphenyl-4-carboxylic acid methyl ester

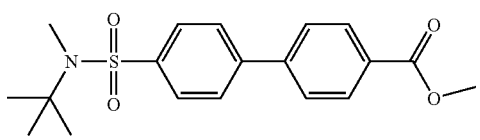

Procedure S': 4'-(tert-Butyl-methyl-sulfamoyl)-biphenyl-4-carboxylic acid methyl ester is prepared in a manner substantially analogous to Procedure O' using 4-bromo-N-tert-butyl-N-methyl-benzenesulfonamide (459 mg, 1.5 mmol), 4-(4,4,5,5-Tetramethyl-[1,3,2]dioxaborolan-2-yl)-benzoic acid methyl ester (CAS 17136-80-0) (490 mg, 1.87 mmol), tricyclohexylphosphine (65 mg, 0.23 mmol), Pd(OAc)₂ (34 mg, 0.15 mmol), and CsF (906 mg, 6 mmol) to give the intermediate 4'-(tert-Butyl-methyl-sulfamoyl)-biphenyl-4-carboxylic acid methyl ester (350 mg, 65% yield). MS (ES+) 384.1 (M+Na)⁺

Intermediate Preparation 11

4'-(tert-Butyl-methyl-sulfamoyl)-biphenyl-4-carboxylic acid

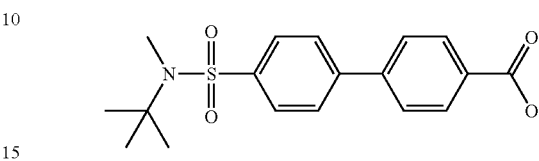

Procedure T': A 15 mL dioxane/H₂O (2:1) mixture of 4'-(tert-butyl-methyl-sulfamoyl)-biphenyl-4-carboxylic acid methyl ester (318 mg, 0.88 mmol) and LiOH—H₂O (46 mg, 1.1 mmol) is stirred at room temperature overnight. The reaction mixture is concentrated, is diluted with EtOAc, shaken with 1 N HCl, and the layers are separated. The 1 N HCl layer is extracted with EtOAc and the combined organic layers are washed with brine, then dried over Na₂SO₄ and evaporated to give the intermediate 4'-(tert-butyl-methyl-sulfamoyl)-biphenyl-4-carboxylic acid (270 mg, 88% yield). MS (ES−) 346.1 (M−H)⁻

Example 24

4'-(2S-Pyrrolidin-1-ylmethyl-pyrrolidine-1-carbonyl)-biphenyl-4-sulfonic acid tert-butyl-dimethylamide

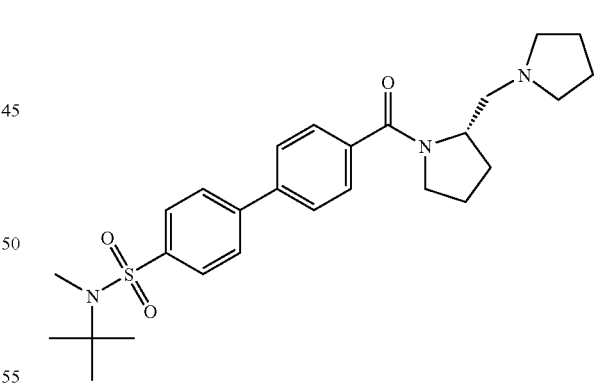

The title compound is prepared in a manner substantially analogous to Procedure B' in 10 mL 10% DMF/dichloromethane using 4'-(tert-butyl-methyl-sulfamoyl)-biphenyl-4-carboxylic acid (243 mg, 0.70 mmol), EDC-HCl (201 mg, 0.1.05 mmol), HOBt (142 mg, 1.05 mmol), DIEA (0.31 mL, 1.75 mmol) and (S)(+)-1-(2-pyrrolidinylmethyl)pyrrolidine (92 mg, 0.60 mmol) to give the title compound (220 mg, 76% yield). MS (ES+) 484.3 (M+H)⁺

Example 25

4'-(2S-Pyrrolidin-1-ylmethyl-pyrrolidine-1-carbonyl)-biphenyl-4-sulfonic acid methylamide

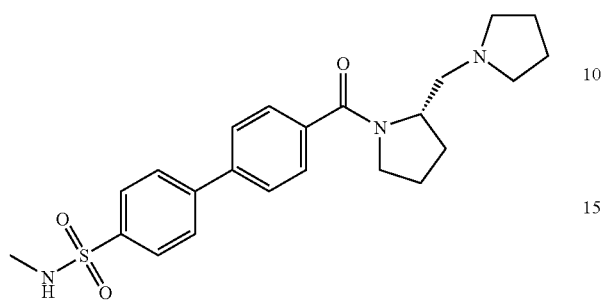

The title compound is prepared in a manner substantially analogous to Procedure Q' in 3 mL dichloromethane using 4'-(2-(S)-pyrrolidin-1-ylmethyl-pyrrolidine-1-carbonyl)-biphenyl-4-sulfonic acid tert-butyl-methyl-amide (208 mg, 0.43 mmol), anisole (0.5 mL, 4.3 mmol), and trifluoroacetic acid (1.5 mL, 20 mmol) to give the product (130 mg, 70% yield). MS (ES+) 428.2 (M+H)+

Intermediate Preparation 12

4-(5-Acetyl-pyridin-2-yl)-benzoic acid methyl ester

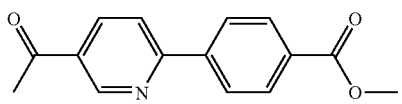

Procedure U': To a stirring solution of 1-(6-chloro-pyridin-3-yl)-ethanone (1.0 mmol, CAS #55676-22-7) and 4-methoxycarbonylphenyl boronic acid (1.2 mmol) in dioxane (0.15M), add tetrakis-(triphenylphosphine) palladium (0.044 mmol) and 2M aqueous sodium carbonate (5.0 mmol). Heat the reaction to 90° C. for three hours. After this time, remove the heat and concentrate in vacuo. Purify the title compound via radial chromatography eluting with methanol and dichloromethane. MS (m/e): 256.1 (M+1)

Intermediate Preparation 13

4-(5-Acetyl-pyridin-2-yl)-benzoic acid sodium salt

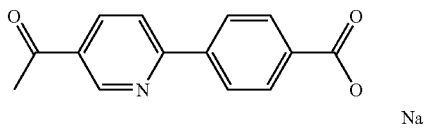

Procedure V': To a stirring solution of 4-(5-acetyl-pyridin-2-yl)-benzoic acid methyl ester (1.0 mmol) in 1:1 tetrahydrofuran/ethanol (0.20M), add 2N sodium hydroxide and heat to reflux for three hours. After this time, concentrate the reaction in vacuo. Rinse the solid with dichloromethane and decant. The title compound, remaining as a solid, requires no further purification. MS (m/e): 242.1 (M+1)

Example 26

1-{6-[4-(2-(S)-Pyrrolidin-1-ylmethyl-pyrrolidine-1-carbonyl)-phenyl]-pyridin-3-yl}-ethanone

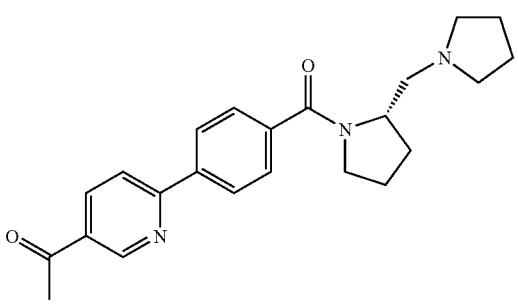

Procedure W': To a stirring solution of 4-(5-acetyl-pyridin-2-yl)-benzoic acid sodium salt (1.0 mmol) and n-methyl morpholine (1.0 mmol) in dichloromethane (0.10M) in a 0° C. ice bath, add 2-chloro-4,6-dimethoxy-1,3,5-triazine (1.0 mmol). Remove the ice bath and stir for 45 minutes. After this time, add (S)-(+)-1-(2-pyrrolidinylmethyl)pyrrolidine (1.0 mmol) and stir at room temperature for three hours. After this time, wash the reaction with saturated aqueous sodium bicarbonate while extracting with 10% isopropanol/dichloromethane (3×). Dry the organic layer with sodium sulfate, filter and concentrate in vacuo. Purify the title compound via chromatography eluting with 2M ammonia in methanol and dichloromethane. MS (m/e): 378.3 (M+1)

Intermediate Preparation 14

(4-Bromo-phenyl)-(2-(S)-pyrrolidin-1-ylmethyl-pyrrolidin-yl)methanone

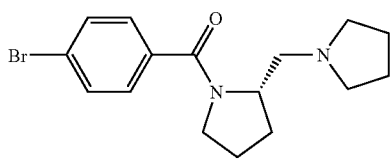

Procedure X': To a stirring solution of 4-bromobenzoic acid-2,5-dioxo-pyrrolidin-1-yl ester (3.5 g, 11.7 mmol), [which can be prepared from 4-bromobenzoic acid and N-hydroxy succinamide by the method of C. Mitsos, Chem Pharm Bull 48(2), 211-214 (2000), or purchased from Ambinter, CAS#80586-82-9], in tetrahydrofuran (0.15M), add (S)-(+)-1-(2-pyrrolidinylmethyl)pyrrolidine and heat to reflux for four hours. After this time, remove the heat and wash the reaction with water while extracting with 10% isopropanol/dichloromethane. Dry the organics with sodium sulfate, filter and concentrate in vacuo. Purify on a silica column eluting with 2M ammonia in methanol and dichloromethane to give (4-bromo-phenyl)-(2-(S)-pyrrolidin-1-ylmethyl-pyrrolidin-yl)methanone (93% yield with 80% purity). MS (m/e): 337.1 (M+1)

Intermediate Preparation 15

4'-(2-(S)-Pyrrolidin-ylmethyl-pyrrolidine-1-carbonyl)-biphenyl-4-carboxylic acid methylamide

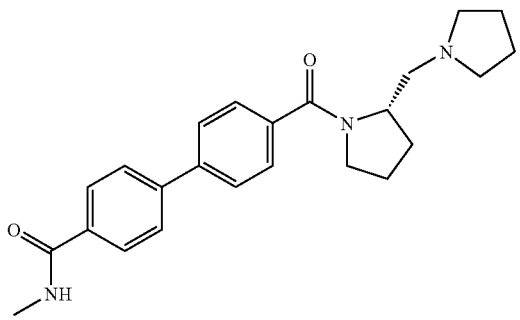

Procedure Z': To a stirring solution of 4-bromophenylmethyl amide (11.0 mmol, CAS # 27466-83-7), bis-(pinacolato)diboron (1.1 mmol) and potassium acetate (3.0 mmol) in dimethyl sulfoxide (0.10M), add palladium(II) dichloride (dppf) complex with dichloromethane (1:1) (0.08 mmol). Heat reaction to 100° C. for 1.5 hours. After this time, cool the reaction to room temperature and add (4-bromo-phenyl)-(2-(S)-pyrrolidin-1-ylmethyl-pyrrolidin-yl)methanone (the product from preparation 14) (1.0 mmol), 2M aqueous sodium carbonate (3.0 mmol) add palladium(II) chloride (dppf) complex with dichloromethane (1:1) (0.08 mmol). Heat reaction to 100° C. for 18 hours. After this time, remove the heat and wash the reaction with water while extracting with 10% isopropanol/dichloromethane. Dry the organics with sodium sulfate, filter and concentrate in vacuo. Purify the title compound via radial chromatography eluting with 2M ammonia in methanol and dichloromethane. MS (m/e): 392.3 (M+1)

Example 27

4'-(2-(S)-Pyrrolidin-ylmethyl-pyrrolidine-1-carbonyl)-biphenyl-4-carboxylic acid methylamide hydrochloride salt

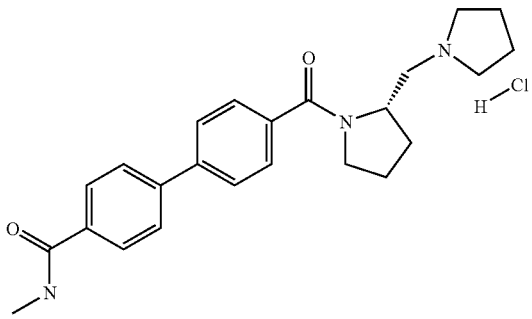

Procedure AA: Dissolve 4'-(2-(S)-Pyrrolidin-ylmethyl-pyrrolidine-1-carbonyl)-biphenyl-4-carboxylic acid methylamide in minimal dichloromethane and add 1M hydrochloric acid in ether until the solution becomes cloudy. Add 1:1 ether/hexanes and concentrate in vacuo to yield the title compound. MS (m/e): 392.3 (M+1)

Example 28

4'(2-(S)-Pyrrolidin-ylmethyl-pyrrolidine-1-carbonyl)-biphenyl-4-carboxylic acid dimethylamide hydrochloride salt

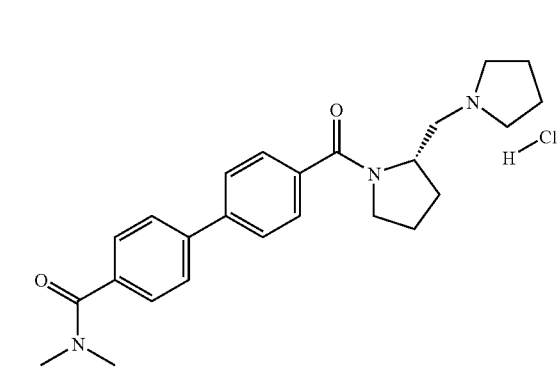

Starting with (4-Bromo-phenyl)-(2-(S)-pyrrolidin-1-ylmethyl-pyrrolidin-yl)methanone and 4-(N,N-dimethylaminocarbonyl)phenyl boronic acid perform procedures significantly analogous to those found in Procedures U' and AA. MS (m/e): 406.3 (M+1)

Example 29

4'-(Methanesulfonyl-biphenyl-4-yl)-(2-(S)-pyrrolidin-1-ylmethyl-pyrrolidin-1-yl)-methanone

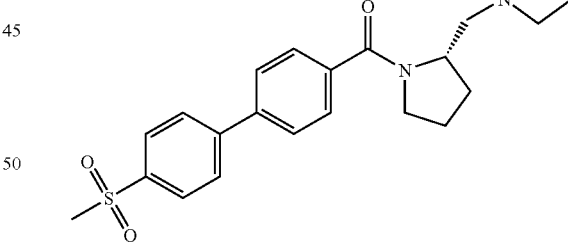

Procedure BB: To a stirring solution of (4-bromo-phenyl)-(2-(S)-pyrrolidin-1-ylmethyl-pyrrolidin-yl)methanone (1.0 mmol) and 4-methylsulfonylphenyl boronic acid (1.5 mmol) in acetonitrile (0.20M), add dichloropalladium di-triphenylphosphine (0.2 mmol) and cesium fluoride (10.0 mmol). Heat the reaction to 80° C. for 18 hours. After this time, remove the heat and wash the reaction with water while extracting with dichloromethane. Dry the organic layer with sodium sulfate, filter and concentrate in vacuo. Purify the title compound via radial chromatography eluting with 2M ammonia in methanol and dichloromethane. MS (m/e): 413.2 (M+1)

Example 30

[4'-(Pyrrolidine-1-carbonyl)-biphenyl-4-yl]-(2-(S)-pyrrolidin-1-ylmethyl-pyrrolidin-1-yl)-methanone

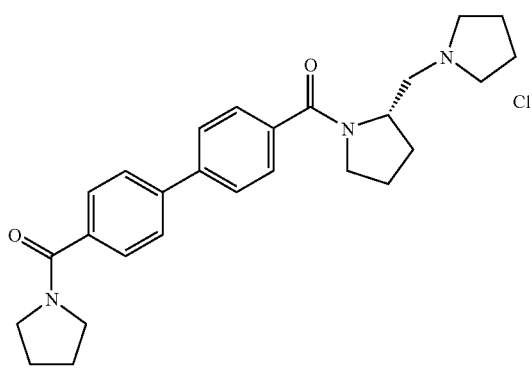

The title compound is prepared starting with (4-Bromo-phenyl)-(2-(S)-pyrrolidin-1-ylmethyl-pyrrolidin-yl)methanone and 4-methoxycarbonylphenyl boronic acid perform procedures significantly analogous to those found in Procedures BB, V', W' (with pyrrolidine in place of (S)-(+)-1-(2-pyrrolidinylmethyl)pyrrolidine) and Q. MS (m/e): 432.4 (M+1)

Intermediate Preparation 16

4-Bromo-2-fluorobenzoic acid chloride

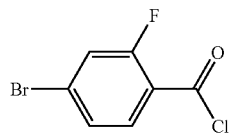

Procedure CC: To a stirring solution of 4-bromo-2-fluorobenzoic acid (1.0 mmol) and oxalyl chloride (2.0 mmol) in dichloromethane (0.10M), add 2 drops of dimethylformamide as a catalyst. Stir at room temperature for 3 hours. After this time, concentrate the reaction in vacuo. Assume total conversion to the acid chloride.

Intermediate Preparation 17

(4-Bromo-2-fluoro-phenyl)-(2-pyrrolidin-1-ylmethyl-pyrrolidin-yl)methanone

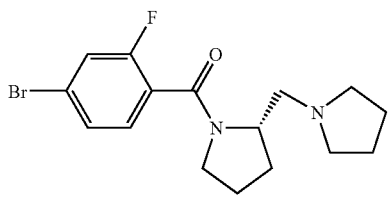

Procedure DD: To a stirring solution of (S)-(+)-1-(2-pyrrolidinylmethyl)pyrrolidine (1.0 mmol) and n-methylmorpholine (1.0 mmol) in dichloromethane (0.10M), slowly add 4-Bromo-2-fluorobenzoic acid chloride (1.0 mmol) diluted in dichloromethane. Stir reaction at room temperature for one hour. After this time wash the reaction with saturated aqueous sodium bicarbonate while extracting with dichloromethane. Dry the organic layer with sodium sulfate, filter and concentrate in vacuo to give the title compound. MS (m/e): 355.1/357.1 (M+1)

Example 31

(3-Fluoro-4'-methanesulfonyl-biphenyl-4-yl)-(2-(S)-pyrrolidin-1-ylmethyl-pyrrolidin-1-yl)-methanone

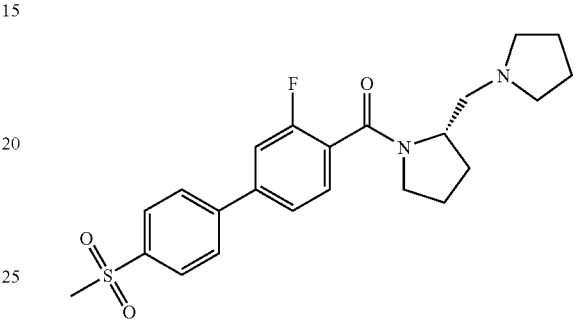

Procedure EE: In a microwave reactor vessel, add (4-bromo-2-fluoro-phenyl)-(2-(S)-pyrrolidin-1-ylmethyl-pyrrolidin-yl)methanone (1.0 mmol), 4-methanesulfonylphenyl boronic acid (2.5 mmol), dichloropalladium di-triphenylphosphine (0.2 mmol), cesium fluoride (9.0 mmol) and acetonitrile (0.20M) and run in a CEM microwave reactor for 10 minutes at 120° C. with 75 W power and cooling on. After this time, wash the reaction with water while extracting with 10% isopropanol/dichloromethane. Dry the organic layer with sodium sulfate, filter and concentrate in vacuo. Purify the title compound via radial chromatography eluting with 2M ammonia in methanol and dichloromethane. MS (m/e): 431.2 (M+1)

Example 32

N-[4'-(2-(S)-Pyrrolidin-1-ylmethyl-pyrrolidine-1-carbonyl)-biphenyl-4-yl]-methanesulfonamide

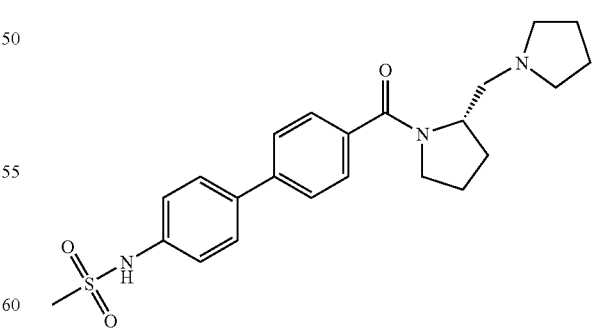

Procedure FF: In a microwave reactor vessel, place (4-bromo-phenyl)-(2-(S)-pyrrolidin-1-ylmethyl-pyrrolidin-yl)methanone (1.0 mmol), 4-methylsulfonamidephenyl boronic acid (1.5 mmol), tetrakis-(triphenylphosphine) palladium (0.044 mmol), dioxane (0.10M) and 2M aqueous sodium carbonate (5.0 mmol) and run in a CEM microwave reactor for 30 minutes at 90° C. with 20 W power and cooling on. After this time, concentrate the reaction in vacuo. Purify the title compound via radial chromatography eluting with 2M ammonia in methanol and dichloromethane. MS (m/e): 428.2 (M+1)

Example 33

N-[4'-(2-(S)-Pyrrolidin-1-ylmethyl-pyrrolidine-1-carbonyl)-biphenyl-3-yl]-methanesulfonamide

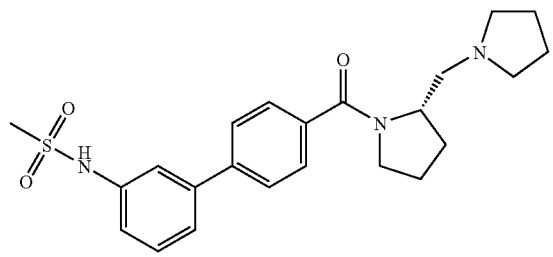

The title compound is prepared starting with (4-Bromo-phenyl)-(2-(S)-pyrrolidin-1-ylmethyl-pyrrolidin-yl)methanone and 3-methylsulfonamidephenyl boronic acid following a procedure significantly analogous to Procedure FF. MS (m/e): 428.2 (M+1)

Intermediate Preparation 18

3'-Methylsulfanyl-biphenyl-4-carboxylic acid methyl ester

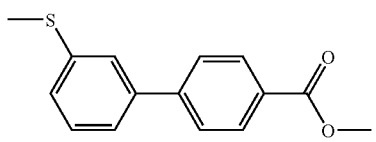

The title compound is prepared beginning with 3-thioanisole boronic acid and methyl-4-iodobenzoate following a procedure significantly analogous to that found in Procedure U'.

Intermediate Preparation 19

3'-Methanesulfonyl-biphenyl-4-carboxylic acid methyl ester

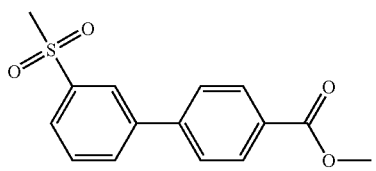

Procedure GG: To a stirring solution of 3'-methylsulfanyl-biphenyl-4-carboxylic acid methyl ester (1.0 mmol) in dichloromethane (0.15M) in a 0° C. ice bath, add 80% metachloroperoxybenzoic acid (1.9 mmol). Remove the ice bath and stir for 30 minutes. Wash the reaction with saturated aqueous sodium bicarbonate while extracting with dichloromethane. Concentrate the organic layer in vacuo and purify the title compound via radial chromatography eluting with ethyl acetate and hexane. MS (m/e): 291.1 (M+1)

Intermediate Preparation 20

3'-Methanesulfonyl-biphenyl-4-carboxylic acid

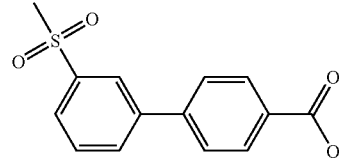

Procedure HH: To a stirring solution of 3'-Methanesulfonyl-biphenyl-4-carboxylic acid methyl ester (1.0 mmol) in 1:1 methanol/tetrahydrofuran (0.15M), add 2N sodium hydroxide (3.0 mmol) and heat to reflux for 1 hour. After this time, remove the heat and concentrate in vacuo. Wash with 1N hydrochloric acid and water while extracting with 10% isopropanol/dichloromethane. Concentrate the organic layer in vacuo to yield the title compound. MS (m/e): 275.1 (M−1)

Example 34

(3'-Methanesulfonyl-biphenyl-4-yl)-(2-(S)-pyrrolidin-1-ylmethyl-pyrrolidin-1-yl)-methanone

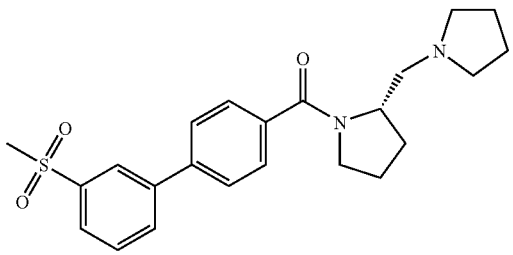

The title compound is prepared starting with 3'-methanesulfonyl-biphenyl-4-carboxylic acid following procedures significantly analogous to those found in Procedures CC and DD. Purify via radial chromatography eluting with 2M ammonia in methanol and dichloromethane. MS (m/e): 413.2 (M+1)

Intermediate Preparation 21

5-Chloro-2-ethylsulfanyl-pyridine

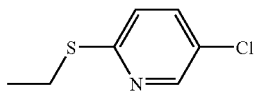

Procedure II: To a solution of 2,5-dichloropyridine (1.0 mmol) (Aldrich#19,376-3) in ethanol (0.33M), add sodium ethanethiolate (0.95 mmol) and heat reaction to reflux for 18 hours. After this time, remove the heat and concentrate in vacuo. Wash with water and saturated aqueous sodium bicarbonate while extracting with dichloromethane. Dry the organic layer with sodium sulfate, filter and concentrate in vacuo. Purify the title compound on a silica column eluting with ethyl acetate and hexane.

Intermediate Preparation 22

5-Chloro-2-ethanesulfonyl-pyridine

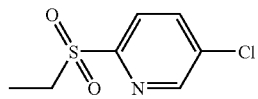

Procedure JJ: To a solution of 5-Chloro-2-ethylsulfanyl-pyridine (1.0 mmol) in ethanol (0.2M), add m-chloroperoxybenzoic acid (2.95 mmol) and stir at room temperature for four hours. After this time, concentrate the reaction in vacuo. Dilute in ethyl acetate and wash with 0.5N sodium hydroxide. Dry the organic layer with sodium sulfate, decant, and concentrate in vacuo. Purify the title compound via radial chromatography eluting with ethyl acetate and hexane. MS (m/e): 205.9 (M+1)

Intermediate Preparation 23

(2-(S)-Pyrrolidin-1-ylmethyl-pyrrolidin-1-yl)-[4-(4,4,5,5-tetramethyl-[1,3,2]dioxaborolan-2-yl)-phenyl]-methanone

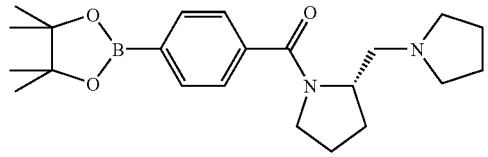

The title compound is prepared starting with 4-(4,4,5,5-Tetramethyl-[1,3,2]dioxaborolan-2-yl)-benzoic acid following a procedure significantly analogous to that found in Procedure W' with the exception that no chromatography is performed. MS (m/e): 385.3 (M+1)

Intermediate Preparation 24

[4-(6-Ethanesulfonyl-pyridin-3-yl)-phenyl]-(2-(S)-pyrrolidin-1-ylmethyl-pyrrolidin-1-yl)-methanone

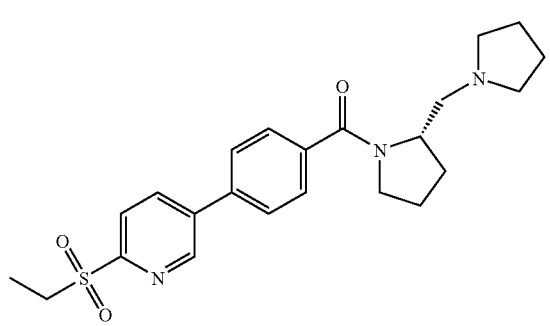

Procedure KK: Place 5-Chloro-2-ethanesulfonyl-pyridine (1.0 mmol), (2-(S)-Pyrrolidin-1-ylmethyl-pyrrolidin-1-yl)-[4-(4,4,5,5-tetramethyl-[1,3,2]dioxaborolan-2-yl)-phenyl]-methanone (1.1 mmol), ethanol (0.10M), potassium carbonate (3.0 mmol) and dihydrogen di-µ-chlorotetrakis(di-tert-butylphosphino-kP)dipalladate (2-) (0.01 mmol, also known as POPd1) in a microwave reactor vessel with a stir bar. Run the reaction in a CEM microwave reactor for 1 hour at 90° C. and 65 W power with cooling. After this time, concentrate the reaction in vacuo. Purify the title compound via radial chromatography eluting with 2M ammonia and dichloromethane. MS (m/e): 428.2 (M+1)

Example 35

[4-(6-Ethanesulfonyl-pyridin-3-yl)-phenyl]-(2-(S)-pyrrolidin-1-ylmethyl-pyrrolidin-1-yl)-methanone dihydrochloride salt

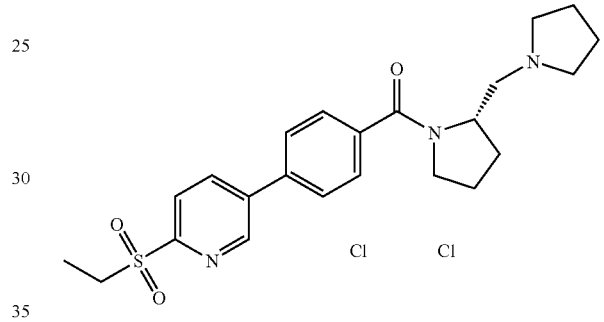

The title compound is prepared starting [4-(6-Ethanesulfonyl-pyridin-3-yl)-phenyl]-(2-(S)-pyrrolidin-1-ylmethyl-pyrrolidin-1-yl)-methanone following a procedure significantly analogous to that found in Procedure AA. MS (m/e): 428.2 (M+1)

Example 36

[4-(6-Ethanesulfonyl-pyridin-3-yl)-2-fluorophenyl]-(2-(S)-pyrrolidin-1-ylmethyl-pyrrolidin-1-yl)-methanone dihydrochloride salt

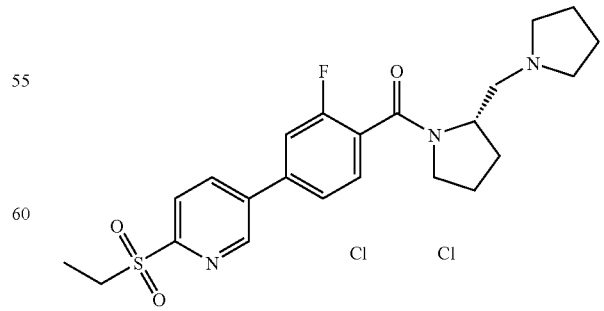

The title compound is prepared starting with 5-chloro-2-ethanesulfonyl-pyridine and 4-carboxy-3-fluorophenylboronic acid following procedures significantly analogous to those found in Procedures KK, CC, DD, and AA. MS (m/e): 446.2 (M+1)

Intermediate Preparation 25

[4-(6-Amino-pyridin-3-yl)-phenyl]-(2-(S)-pyrrolidin-1-ylmethyl-pyrrolidin-1-yl)-methanone

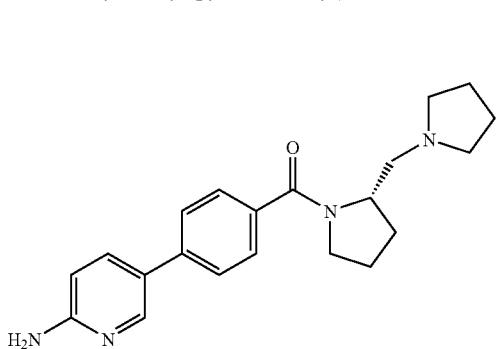

The title compound is prepared starting with 5-iodo-pyridin-2-ylamine and (2-(S)-Pyrrolidin-1-ylmethyl-pyrrolidin-1-yl)-[4-(4,4,5,5-tetramethyl-[1,3,2]dioxaborolan-2-yl)-phenyl]-methanone following a procedure significantly analogous to Procedure FF. MS (m/e): 351.2 (M+1)

Intermediate Preparation 26

N-{5-[4-(2-(S)-Pyrrolidi-1-ylmethyl-pyrrolidine-1-carbonyl)-phenyl]-pyridin-2-yl}-methanesulfonamide

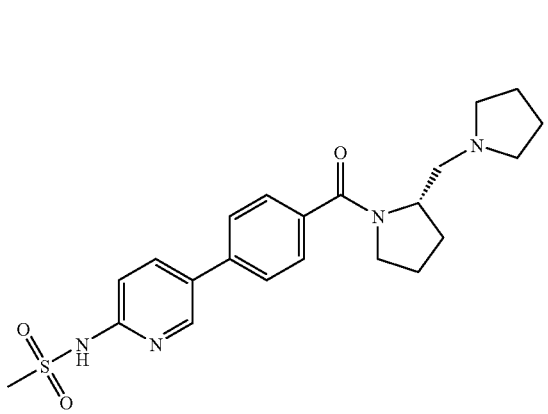

Procedure LL: To a stirring solution of [4-(6-amino-pyridin-3-yl)-phenyl]-(2-(S)-pyrrolidin-1-ylmethyl-pyrrolidin-1-yl)-methanone (1.0 mmol) in 3:1 dichloromethane/pyridine (0.10M), add methanesulfonyl chloride (1.3 mmol) and stir at room temperature for 48 hours. After this time, wash the reaction with 1N hydrochloric acid while extracting with dichloromethane. Using 2N sodium hydroxide, make the aqueous phase basic and extract with 10% isopropanol/dichloromethane. The product remains in the aqueous layer during the acid/base workup. Concentrate the aqueous layer in vacuo and purify the title compound via radial chromatography eluting with 2M ammonia and dichloromethane. MS (m/e): 429.2 (M+1)

Example 37

N-{5-[4-(2-(S)-Pyrrolidin-1-ylmethyl-pyrrolidine-1-carbonyl)-phenyl]-pyridin-2-yl}-methanesulfonamide dihydrochloride salt

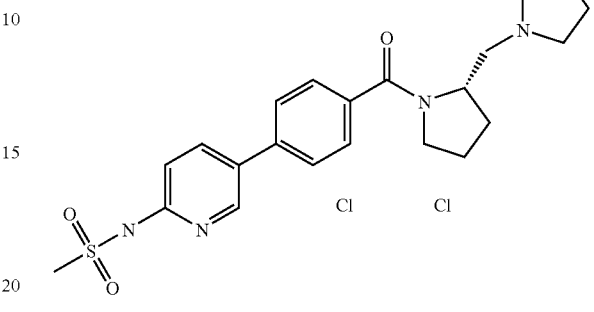

The title compound is prepared starting with N-{5-[4-(2-(S)-pyrrolidin-1-ylmethyl-pyrrolidine-1-carbonyl)-phenyl]-pyridin-2-yl}-methanesulfonamide following a procedure significantly analogous to Procedure AA. MS (m/e): 429.2 (M+1)

Example 38

(2-(S)-Pyrrolidin-1-ylmethyl-pyrrolidin-1-yl)-(4'-trifluoromethanesulfonyl-biphenyl-4-yl)-methanone hydrochloride salt

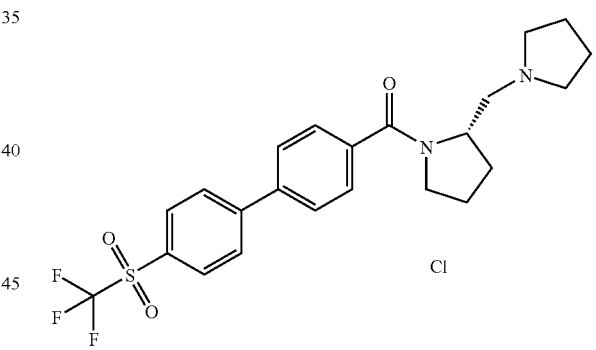

The title compound is prepared starting with 4-(trifluoromethylthio)bromobenzene and 4-methoxycarbonylphenyl boronic acid following procedures significantly analogous to Procedures U', JJ, HH, CC, DD, and AA to yield the desired compound. MS (m/e): 467.1 (M+1)

Intermediate Preparation 27

N-(4-Bromo-2-fluoro-phenyl)-methanesulfonamide

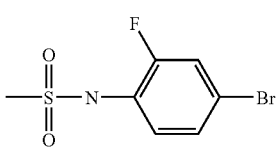

Procedure MM: To a stirring solution of 4-bromo-2-fluoroaniline (1.0 mmol) in 3:1 dichloromethane/pyridine, add methanesulfonyl chloride (1.5 mmol) and stir at room temperature for 18 hours. After this time, wash the reaction with 1N hydrochloric acid while extracting with dichloromethane. Purify the title compound via radial chromatography eluting with ethyl acetate and hexane.

Example 39

N-[3-Fluoro-4'-(2-(S)-pyrrolidin-1-ylmethyl-pyrrolidine-1-carbonyl)-biphenyl-4-yl]-methanesulfonamide

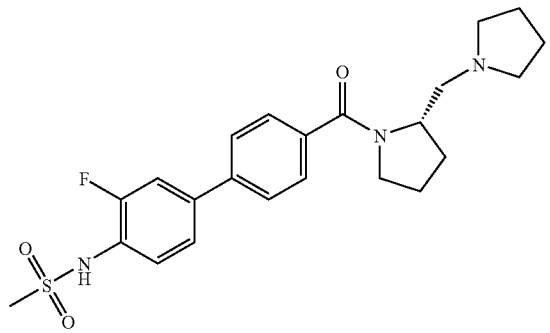

The title compound is prepared starting with (2-(S)-pyrrolidin-1-ylmethyl-pyrrolidin-1-yl)-[4-(4,4,5,5-tetramethyl-[1,3,2]dioxaborolan-2-yl)-phenyl]-methanone and N-(4-Bromo-2-fluoro-phenyl)-methanesulfonamide following a procedure significantly analogous to Procedure FF. MS (m/e): 446.2 (M+1)

Example 40

(4'-Ethanesulfonyl-biphenyl-4-yl)-(2-(S)-pyrrolidin-1-ylmethyl-pyrrolidin-1-yl)-methanone

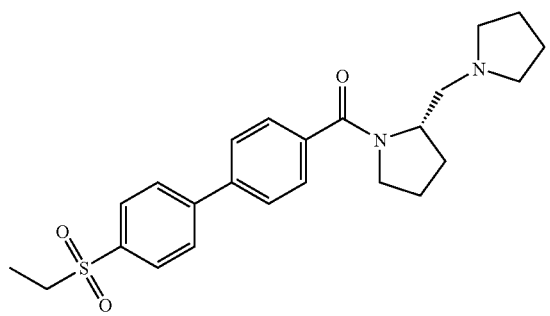

The title compound is prepared starting with (4-Bromo-phenyl)-(2-(S)-pyrrolidin-1-ylmethyl-pyrrolidin-yl)methanone and 4-ethanesulfonylphenyl boronic acid perform a procedure analogous to Procedure FF. MS (m/e): 427.2 (M+1)

Example 41

(S)-(4'-Nitro-biphenyl-4-yl)-(2-pyrrolidin-1-ylmethyl-pyrrolidin-1-yl)-methanone

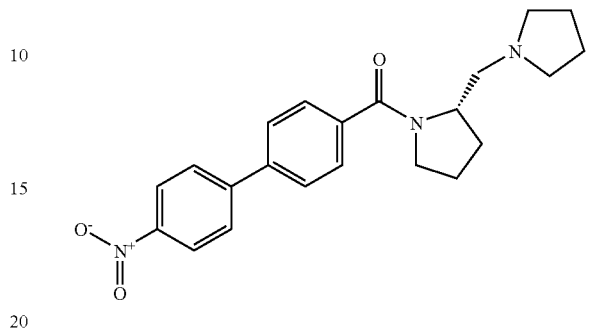

Procedure NN: 4'-Nitro-biphenyl-4-carboxylic acid 200 mg (0.82 mmol), 152 mg of (S)(+)-1-(2-pyrrolidinylmethyl)pyrrolidine (0.99 mmol), 515 mg of bromo-tris-pyrrolidino-phosphonium hexafluorophosphate (PyBOP) (0.99 mmol) and 100 mg of triethylamine (0.99 mmol) are put into 5 ml of dichloromethane and stirred at room temperature for overnight. The reaction mixture is diluted with dichloromethane, washed by brine, dried over Na$_2$SO$_4$ and evaporated. The crude product is applied to silica-gel column chromatography (CH$_2$Cl$_2$:2M NH$_3$ in MeOH=20:1), followed by SCX column to give the product. 163 mg (52%) Observed mass; 380 (M+1)

Example 42

(S)-(4'-Amino-biphenyl-4-yl)-(2-pyrrolidin-1-ylmethyl-pyrrolidin-1-yl)-methanone

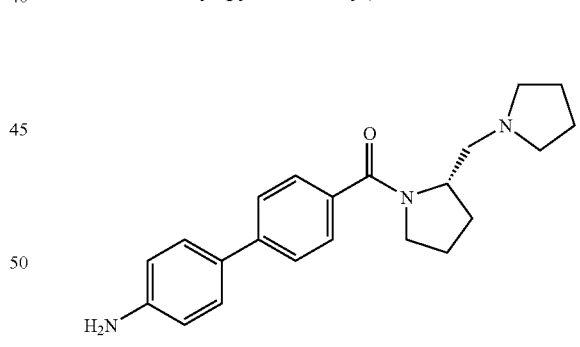

Procedure OO: 160 mg of (4'-Nitro-biphenyl-4-yl)-(2-(S)-pyrrolidin-1-ylmethyl-pyrrolidin-1-yl)-methanone (0.43 mmol) is put into the solution of 485 mg of SnCl$_2$.2H$_2$O (2.15 mmol) in 1.0 ml of EtOH. 1.0 ml of conc. HCl is added to the mixture and heated at 60° C. for 30 min. EtOH is removed in vacuo and the solution is made it to pH=12.0 by aqueous NaOH. This mixture is extracted with dichloromethane, dried over Na$_2$SO$_4$ and evaporated. The crude product is applied to SCX column and washed by MeOH and the desired product is eluted with 2M NH$_3$ in MeOH. The elution is concentrated and applied to silica-gel column chromatography (CH$_2$Cl$_2$:

2M NH₃ in MeOH=20:1) to give the title compound. 77 mg (51%) Observed mass; 350 (M+1)

Example 43

(S)-(4'-Methoxy-biphenyl-4-yl)-(2-pyrrolidin-1-ylm-ethyl-pyrrolidin-1-yl)-methanone

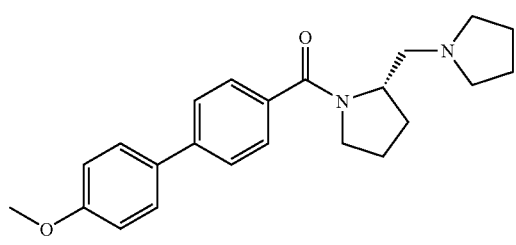

The title compound is prepared from 4'-methoxy-biphenyl-4-carboxylic acid in a manner substantially similar to Procedure M'. Observed mass 365.

Example 44

(S)-(4'-Bromo-biphenyl-4-yl)-(2-pyrrolidin-1-ylm-ethyl-pyrrolidin-1-yl)-methanone

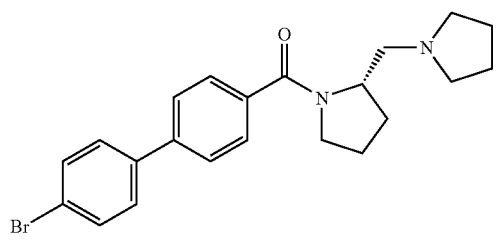

The title compound is prepared from 4'-bromo[1,1'-biphenyl]-4-carboxylic acid in a manner substantially similar to Procedure M'. Observed mass 414.

Example 45

(S)-(2'-Nitro-biphenyl-4-yl)-(2-pyrrolidin-1-ylm-ethyl-pyrrolidin-1-yl)-methanone

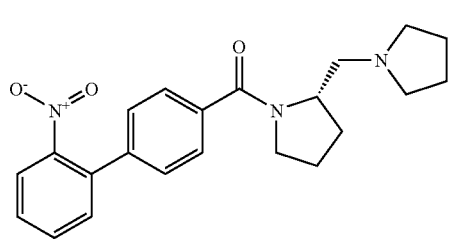

The title compound is prepared from 2'-Nitro-biphenyl-4-carboxylic acid in a manner substantially similar to Procedure M'. Observed mass 380.

Example 46

(S)-(4'-Ethyl-biphenyl-4-yl)-(2-pyrrolidin-1-ylm-ethyl-pyrrolidin-1-yl)-methanone

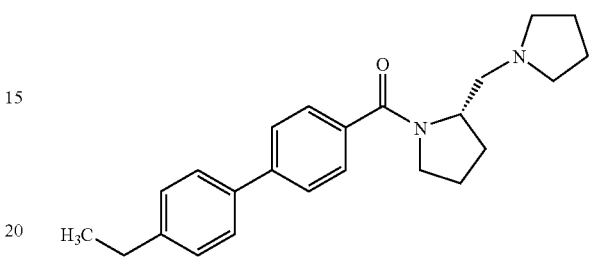

The title compound is prepared from 4'-ethyl-4-biphenylcarboxylic acid in a manner substantially similar to Procedure M'. Observed mass 363.

Example 47

(S)-Biphenyl-4-yl-(2-pyrrolidin-1-ylmethyl-pyrrolidin-1-yl)-methanone

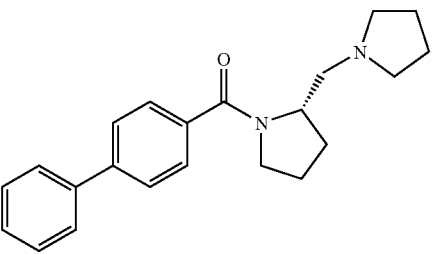

The title compound is prepared from 4-biphenylcarboxylic acid in a manner substantially similar to Procedure M'. Observed mass 335.

Example 48

(S)-(4'-Propyl-biphenyl-4-yl)-(2-pyrrolidin-1-ylm-ethyl-pyrrolidin-1-yl)-methanone

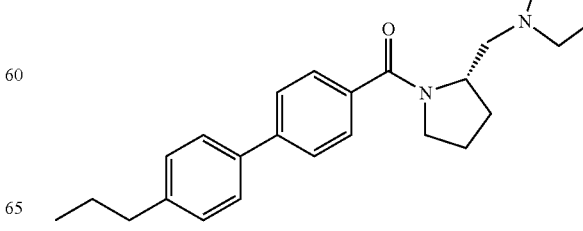

The title compound is prepared from 4-(4-N-propylphenyl) benzoic acid in a manner substantially similar to Procedure M'. Observed mass 377.

Example 49

(S)-[4'-(2-Piperidin-1-yl-ethoxy)-biphenyl-4-yl]-(2-pyrrolidin-1-ylmethyl-pyrrolidin-1-yl)-methanone

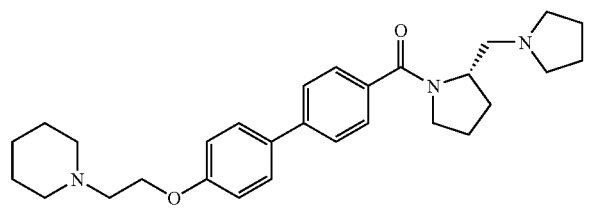

The title compound is prepared from 4'-(2-Piperidin-1-yl-ethoxy)-biphenyl-4-carboxylic acid in a manner substantially similar to Procedure M'. Observed mass 462.

Example 50

(S)-(4'-tert-Butyl-biphenyl-4-yl)-(2-pyrrolidin-1-ylmethyl-pyrrolidin-1-yl)-methanone

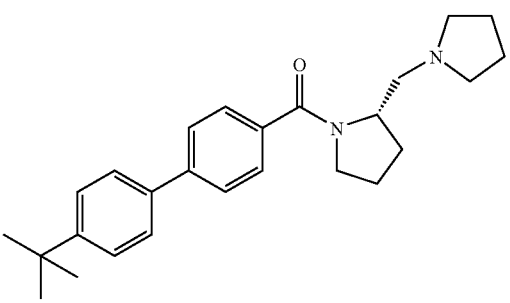

The title compound is prepared from 4-(4-t-butylphenyl)benzoic acid in a manner substantially similar to Procedure M'. Observed mass 391.

Example 51

(S)-(4'-Hexyl-biphenyl-4-yl)-(2-pyrrolidin-1-ylmethyl-pyrrolidin-1-yl)-methanone

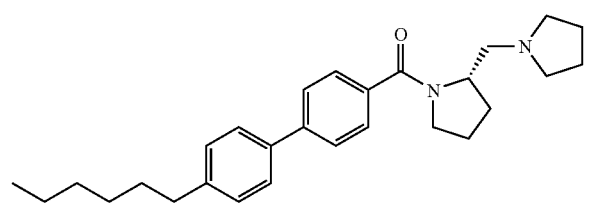

The title compound is prepared from 4-n-hexylbiphenyl-4'-carboxylic acid in a manner substantially similar to Procedure M'. Observed mass 419.

Example 52

(S)-(2-Pyrrolidin-1-ylmethyl-pyrrolidin-1-yl)-[1,1';3',1"]terphenyl-4-yl-methanone

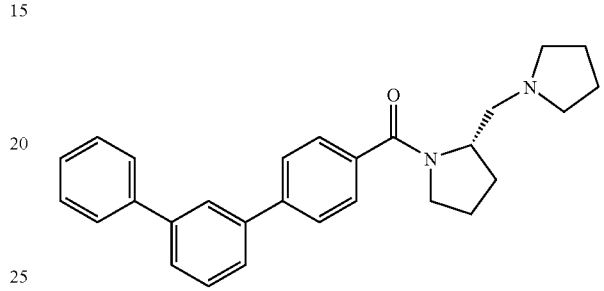

The title compound is prepared from [1,1';3',1"]Terphenyl-4-carboxylic acid (CAS 5731-09-9) in a manner substantially similar to Procedure M'. Observed mass 411.

Intermediate Preparation 28

(2S-Pyrrolidin-1-ylmethyl-pyrrolidin-1-yl)-(-4-bromo-3-fluoro-phenyl-4-yl)-methanone

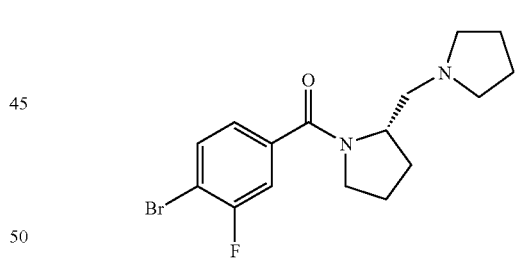

Procedure PP: 4-Bromo-3-fluorobenzoic acid (CAS 153556-42-4) (0.5 g, 2.28 mmol) is dissolved in dichloromethane (25 ml) containing dimethylformamide (200 µl) with stirring at room temperature. Oxalyl chloride (0.5 ml, 5.7 mmol) is added and the reaction is left to stir overnight. The solvent is removed under reduced pressure and the residue is taken up in dichloromethane (15 ml) and added dropwise to a solution of triethylamine (1 ml) and (S)(+)-1-(2-pyrrolidinylmethyl)pyrrolidine (0.36 g, 2.3 mmol) and this mixture is stirred at room temperature for two hours. Aqueous sodium hydroxide solution is added to the mixture and the organic layer is collected, dried over $MgSO_4$ and evaporated to give the product. MS (FIA) 354/356 ($MH^+$)

Example 53

3-Fluoro-4-pyridin-4-yl-phenyl)-(2S-Pyrrolidin-1-ylmethyl-pyrrolidin-1-yl)-methanone

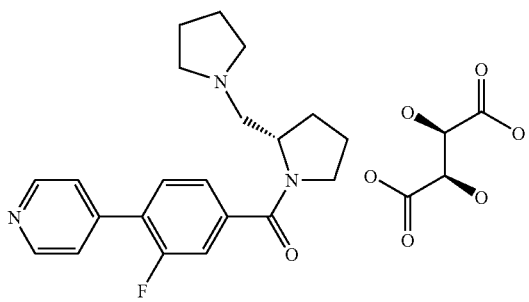

Procedure QQ: (2S-Pyrrolidin-1-ylmethyl-pyrrolidin-1-yl)-(-4-bromo-3-fluoro-phenyl-4-yl)-methanone (0.3 g, 0.845 mmol), pyridine-4-boronic acid (0.11 g, 0.89 mmol) and sodium carbonate (0.46 g, 4.2 mmol) are suspended in dioxane/water (9:1) (25 ml). The mixture is degassed for 20 minutes with a nitrogen stream, tetrakis (triphenylphosphine) palladium (0.05 g, 0.04 mmol) is added and the mixture is heated to reflux under nitrogen overnight. The mixture is concentrated under reduced pressure, taken up in methanol and absorbed onto an SCX-2 column, washed with methanol and eluted off with 2M $NH_3$ in methanol and concentrated under reduced pressure to give the crude product. The crude product is purified by silica-gel column chromatography (gradient: 100% $CH_2Cl_2$ to 10% 2M $NH_3$ in MeOH/$CH_2Cl_2$) give the product. MS (FIA) 354 (MH$^+$). This product was dissolved in methanol, L-tartaric acid (1 equivalent) was added and the mixture was heated to dissolve all solids. The mixture was allowed to cool and diethyl ether was added until the mixture became cloudy. The mixture was left to stand overnight and then filtered to collect the salt.

Example 54

(2-Fluoro-4'-methanesulfonyl-biphenyl-4-yl)-(2S-pyrrolidin-1-ylmethyl-pyrrolidin-1-yl)-methanone

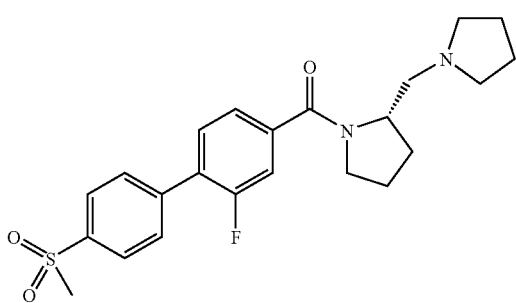

Is prepared in a manner substantially analogous to Procedure QQ staring with (2S-Pyrrolidin-1-ylmethyl-pyrrolidin-1-yl)-(-4-bromo-3-fluoro-phenyl-4-yl)-methanone and 4-Methylsulfonyl benzene boronic acid. MS (FIA) 431 (MH$^+$)

Example 55

[4-(2-Methoxy-pyrimidin-5-yl)-phenyl]-(2-(S)-pyrrolidin-1-ylmethyl-pyrrolidin-1-yl)-methanone

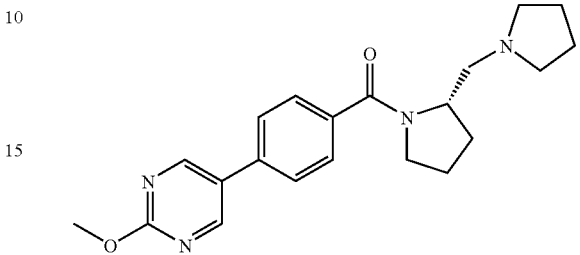

Procedure SS: To a stirred solution of (4-bromo-phenyl)-(2-(S)-pyrrolidin-1-ylmethyl-pyrrolidin-1-yl)-methanone (100 mg, 0.297 mmol), sodium carbonate (94.4 mg, 0.890 mmol) and 2-Methoxy-5-pyrimidine boronic acid (230 mg, 1.48 mmol) in toluene (5 ml), water (1 ml) and ethanol (1.5 ml) under nitrogen was added Tetrakis (triphenylphosphine) palladium (0) (34.3 mg, 0.030 mmol). The reaction was then heated to reflux for 48 h. The reaction was allowed to cool and bound to a SCX-2 cartridge (5 g). The cartridge was washed with two cartridge volumes of dimethylformamide and one volume of methanol. The product was eluted using 2M ammonia in methanol. The ammonia/methanol solution was evaporated on a Genevac HT4. The sample was further purified by prep-LCMS. The resulting acetonitrile/water fractions were combined and evaporated using a Genevac to give 51 mg of a colourless oil (47%). MS (ES+) 367.3

Example 56

[4-(6-Methoxy-pyridin-3-yl)-phenyl]-(2-(S)-pyrrolidin-1-ylmethyl-pyrrolidin-1-yl)-methanone

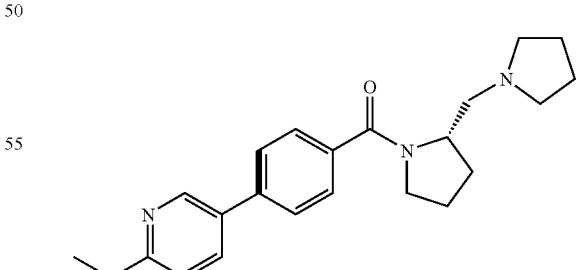

The title compound is prepared in a manner substantially analogous to Procedure SS starting from 2-Methoxy-5-pyridine boronic acid and (4-bromo-phenyl)-(2-(S)-pyrrolidin-1-ylmethyl-pyrrolidin-1-yl)-methanone. MS (ES+) 366.4

Example 57

(4-Benzo[1,3]dioxol-5-yl-phenyl)-(2-(S)-pyrrolidin-1-ylmethyl-pyrrolidin-1-yl)-methanone

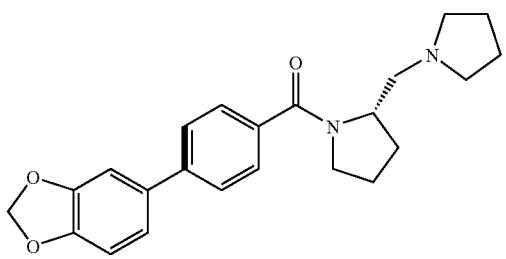

The title compound is prepared in a manner substantially analogous to Procedure SS starting from 3,4-Methylene-dioxybenzene boronic acid and (4-bromo-phenyl)-(2-(S)-pyrrolidin-1-ylmethyl-pyrrolidin-1-yl)-methanone. MS (ES+) 379.4

Example 58

[4-(2,3-Dihydro-benzo[1,4]dioxin-6-yl)-phenyl]-(2-(S)-pyrrolidin-1-ylmethyl-pyrrolidin-1-yl)-methanone

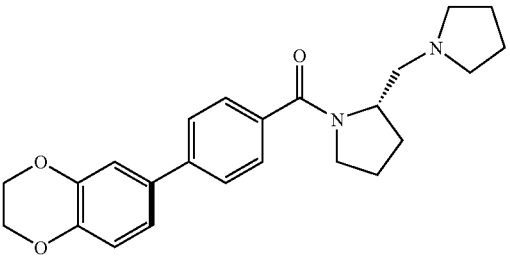

The title compound is prepared in a manner substantially analogous to Procedure SS starting from 2,3-Dihydro-1,4-benzodioxin-6-yl boronic acid and (4-bromo-phenyl)-(2-(S)-pyrrolidin-1-ylmethyl-pyrrolidin-1-yl)-methanone. MS (ES+) 393.2

Example 59

(2-Fluoro-4-pyridin-4-yl-phenyl)-(2 (S)-pyrrolidin-1-ylmethyl-pyrrolidin-1-yl)-methanone

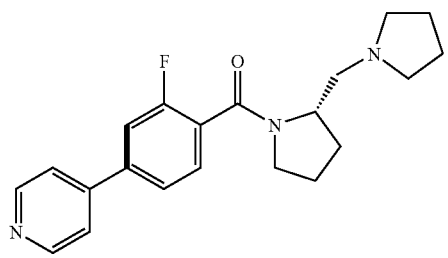

The title compound is prepared in a manner substantially analogous to Procedure FF, T' and B' starting from 4-pyridine boronic acid and 4-bromo-2-fluoro-benzoic acid methyl ester. MS (ES+) 354.2

Intermediate Preparation 29

(2-(S)-Hydroxymethyl-pyrrolidin-1-yl)-(4'-trifluoromethyl-biphenyl-4-yl)-methanone

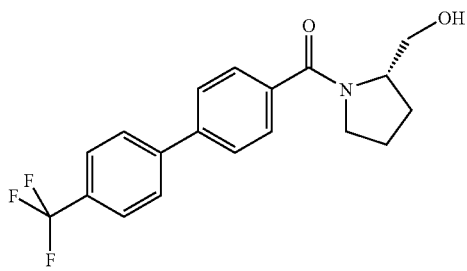

The title compound is prepared in a manner substantially analogous to Procedure B' from 4'-trifluoromethyl-biphenyl-4-carboxylic acid, lithium salt using (S)-2-pyrrolidine methanol as the amine. MS (ES+) 350.2,

Example 60 (Isomer 1) & Example 61 (Isomer 2)

[2-(S)-(2-Methyl-pyrrolidin-1-ylmethyl)-pyrrolidin-1-yl]-(4'-trifluoromethyl-biphenyl-4-yl)-methanone,

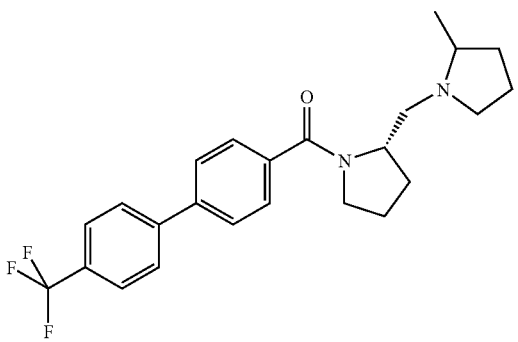

Procedure RR: A mixture of (2-(S)-Hydroxymethyl-pyrrolidin-1-yl)-(4'-trifluoromethyl-biphenyl-4-yl)-methanone (1.0 g, 2.9 mmol) and triethylamine (0.48 mL, 3.4 mmol) in dichloromethane (20 mL) is cooled to 0° C. Methanesulfonyl chloride is added (0.28 mL, 3.6 mmol), and the ice bath removed and the mixture allowed to stir at room temperature for 2 h. The solvent is then removed and the crude material used in the next reactions without further purification.

The crude mesylate (0.57 mmol) is dissolved in THF (10 mL) and methyl pyrrolidine is added (0.97 g, 5.7 mmol). The mixture is heated for 48 h at 70° C. The solvent is then removed in vacuo, and the crude residue taken up in ethyl acetate and washed several times with water, followed by brine. The organic layer is dried over $Na_2SO_4$, and the crude reaction mixture purified by flash chromatography (10% MeOH/CH₂Cl₂) to yield 25 mg of each diastereomer. MS (ES+) 417.2 (both isomers).

Example 62

(2-Fluoro-3-pyridin-4-yl-phenyl)-(2 (S)-pyrrolidin-1-ylmethyl-pyrrolidin-1-yl)-methanone

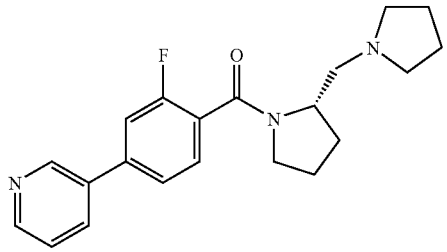

The title compound is prepared in a manner substantially analogous to Procedure FF starting from 3-pyridine boronic acid and (4-bromo-2-fluoro-phenyl)-(2-(S)-pyrrolidin-1-ylmethyl-pyrrolidin-1-yl)-methanone. MS (ES+) 354.2

Intermediate Preparation 30

(4-Bromo-2-trifluoromethyl-phenyl)-(2-(S)-pyrrolidin-1-ylmethyl-pyrrolidin-1-yl)-methanone

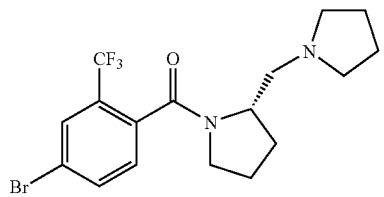

The title compound is prepared in a manner substantially analogous to Procedure E' from 2-trifluoromethyl-4 bromobenzoic acid (CAS 320-31-0). MS (FIA) 373/375 (MH⁺)

Intermediate Preparation 31

(4-Bromo-2,6-difluoro-phenyl)-(2-(S)-pyrrolidin-1-ylmethyl-pyrrolidin-1-yl)-methanone

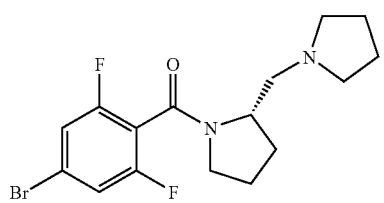

The title compound is prepared in a manner substantially analogous to Procedure E' from 2,6-difluoro-4-bromobenzoic acid (CAS 183065-68-1). MS (FIA) 373/375 (MH⁺)

Example 63

(4'-Methanesulfonyl-4-trifluoromethyl-biphenyl-3-yl)-(2-(S)-pyrrolidin-1-ylmethyl-pyrrolidin-1-yl)-methanone

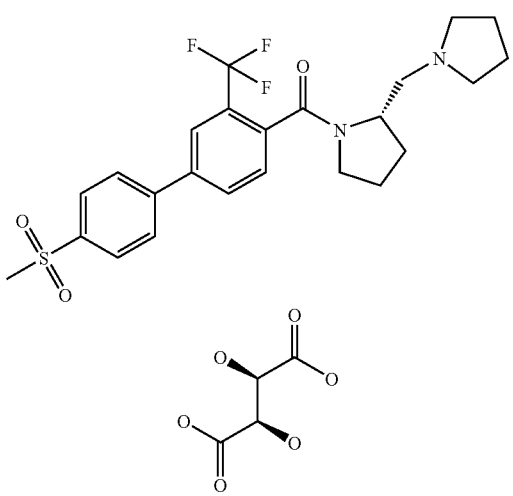

The title compound is prepared in a manner substantially analogous to Example 14 via Procedure F' from (4-bromo-2-trifluoromethyl-phenyl)-(2-(S)-pyrrolidin-1-ylmethyl-pyrrolidin-1-yl)-methanone and 4-methanesulfonylbenzene boronic acid (CAS 149104-88-1). MS (FIA) 481 (MH⁺)

Example 64

(5-Pyridin-4-yl-2-trifluoromethyl-phenyl)-(2-(S)-pyrrolidin-1-ylmethyl-pyrrolidin-1-yl)-methanone

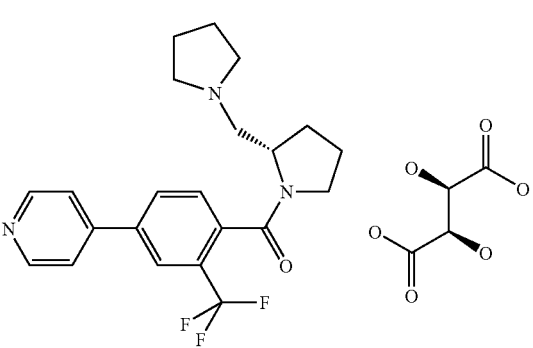

The title compound is prepared in a manner substantially analogous to Example 14 via Procedure F' from (4-bromo-2-trifluoromethyl-phenyl)-(2-(S)-pyrrolidin-1-ylmethyl-pyrrolidin-1-yl)-methanone and pyridine-4-boronic acid. MS (FIA) 404 (MH⁺)

Example 65

(3,5-Difluoro-4'-methanesulfonyl-biphenyl-4-yl)-(2-(S)-pyrrolidin-1-ylmethyl-pyrrolidin-1-yl)-methanone

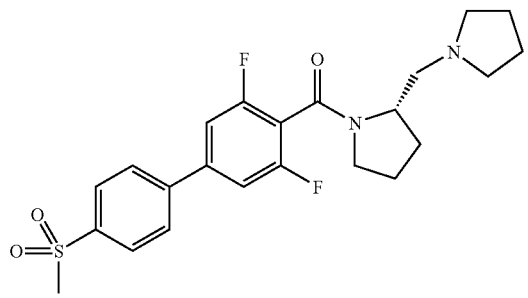

The title compound is prepared in a manner substantially analogous to Example 14 via Procedure F' from (4-bromo-2,6-difluoro-phenyl)-(2-(S)-pyrrolidin-1-ylmethyl-pyrrolidin-1-yl)-methanone and 4-methanesulfonylbenzene boronic acid (CAS 1491 04-88-1). MS (FIA) 489 (MH$^+$)

Example 66

(2,6-Difluoro-4-pyridin-4-yl-phenyl)-(2-(S)-pyrrolidin-1-ylmethyl-pyrrolidin-1-yl)-methanone

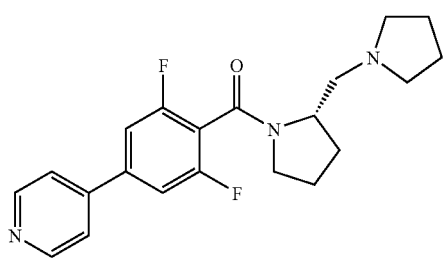

The title compound is prepared in a manner substantially analogous to Example 14 via Procedure F' from (4-bromo-2,6-difluoro-phenyl)-(2-(S)-pyrrolidin-1-ylmethyl-pyrrolidin-1-yl)-methanone and pyridine-4-boronic acid. MS (FIA) 372 (MH$^+$)

Example 67

[2,6-Difluoro-4-(2-methoxy-pyrimidin-5-yl)-phenyl]-(2-(S)-pyrrolidin-1-ylmethyl-pyrrolidin-1-yl)-methanone

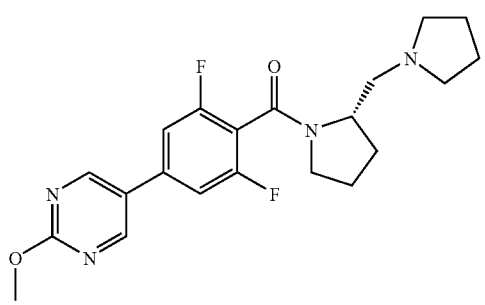

The title compound is prepared in a manner substantially analogous to Example 14 via Procedure F' from (4-bromo-2,6-difluoro-phenyl)-(2-(S)-pyrrolidin-1-ylmethyl-pyrrolidin-1-yl)-methanone and 2-methoxypyrimidine-5-boronic acid (CAS 628692-15-9). MS (FIA) 403 (MH$^+$)

Intermediate 32

3-Fluoro-4'-methanesulfonylamino-biphenyl-4-carboxylic acid

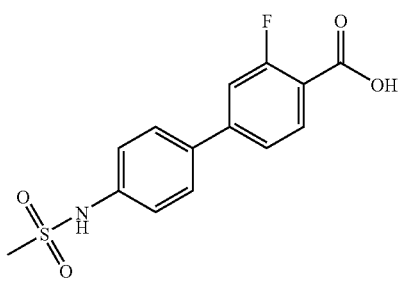

The title compound is prepared starting with 4-bromo-2-fluorobenzoic acid and 4-methylsulfonamidephenyl boronic acid and following a procedure significantly analogous to Procedure FF. Purify via aqueous work-up. MS (m/e): 308.1 (M−1)

Example 68

N-[3'-Fluoro-4'-(2-(S)-pyrrolidin-1-ylmethyl-pyrrolidine-1-carbonyl)-biphenyl-4-yl]-methanesulfonamide

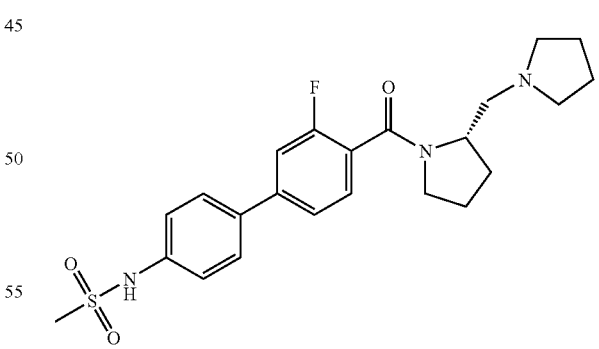

The title compound is prepared starting with 3-Fluoro-4'-methanesulfonylamino-biphenyl-4-carboxylic acid (See Intermediate Preparation 32) and following procedures significantly analogous to Procedures CC, and DD. Purify the title compound via radial chromatography eluting with 2M ammonia in methanol and dichloromethane. MS (m/e): 446.2 (M+1)

Intermediate 33

3-Fluoro-4'-(methanesulfonyl-methyl-amino)-biphenyl-4-carboxylic acid methyl ester

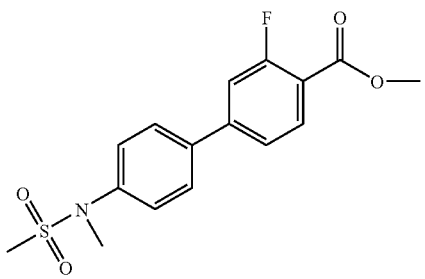

Procedure TT: To a stirring solution of 3-Fluoro-4'-methanesulfonylamino-biphenyl-4-carboxylic acid (See Intermediate Preparation 32) (1.0 mmol) and potassium carbonate (2.2 mmol) in dimethylformamide (0.10M), slowly add methyl iodide (2.0 mmol). Stir the reaction at room temperature for 15 minutes before heating (approximately 60° C.) and stirring for an additional 30 minutes. After this time, perform an aqueous work up while extracting with dichloromethane. Dry the organics with sodium sulfate, decant and concentrate in vacuo. Purify via radial chromatography eluting with ethyl acetate and hexane. MS (m/e): 338.1 (M+1)

Intermediate 34

3-Fluoro-4'-(methanesulfonyl-methyl-amino)-biphenyl-4-carboxylic acid

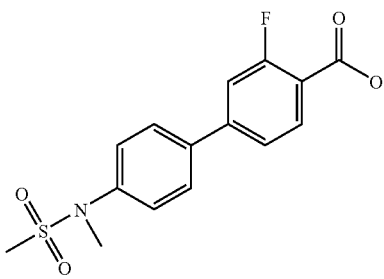

Procedure UU: To a stirring solution of 3-Fluoro-4'-(methanesulfonyl-methyl-amino)-biphenyl-4-carboxylic acid methyl ester (see Intermediate Preparation 33) (1.0 mmol) in 1:1 methanol/tetrahydrofuran, add 2N sodium hydroxide (3.0 mmol) and stir at room temperature for 4 hours. After this time wash the reaction with 1N hydrochloric acid while extracting with dichloromethane. Dry the organics with sodium sulfate, decant, and concentrate in vacuo. MS (m/e): 322.1 (M−1)

Example 69

N-[3'-Fluoro-4'-(2-(S)-pyrrolidin-1-ylmethyl-pyrrolidine-1-carbonyl)-biphenyl-4-yl]-N-methyl-methanesulfonamide

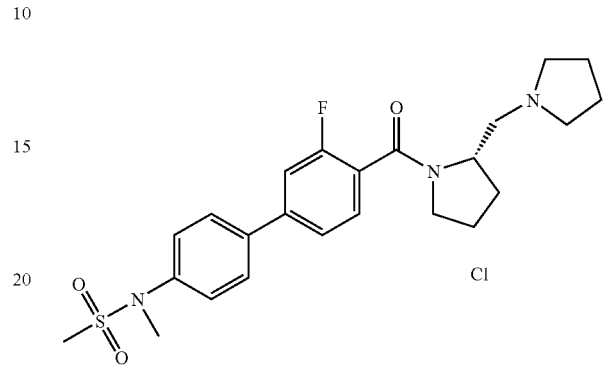

The title compound is prepared by starting with 3-Fluoro-4'-(methanesulfonyl-methyl-amino)-biphenyl-4-carboxylic acid (See Intermediate Preparation 34) and following procedure significantly analogous to Procedures CC, DD, and AA. MS (m/e): 460.2 (M+1)

Example 70

[2-(S)-(2-(R)-Methyl-pyrrolidin-1-ylmethyl)-pyrrolidin-1-yl]-(4'-trifluoromethyl-biphenyl-4-yl)-methanone

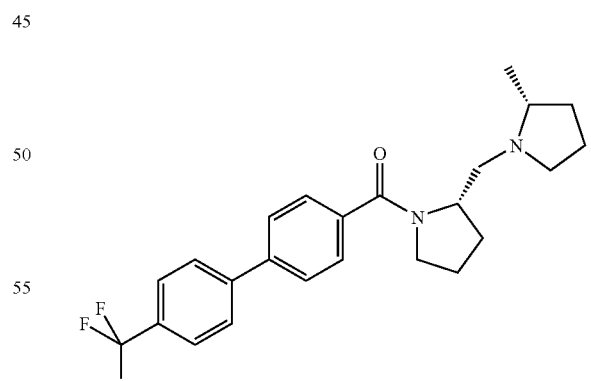

The title compound is prepared in a manner substantially analogous to Procedure RR from (2-(S)-Hydroxymethyl-pyrrolidin-1-yl)-(4'-trifluoromethyl-biphenyl-4-yl)-methanone and (R)-methylpyrrolidine as the amine. MS (ES+) 417.2

Example 71

(3-Fluoro-3'-trifluoromethyl-biphenyl-4-yl)-(2-(S)-pyrrolidin-1-ylmethyl-pyrrolidin-1-yl)-methanone

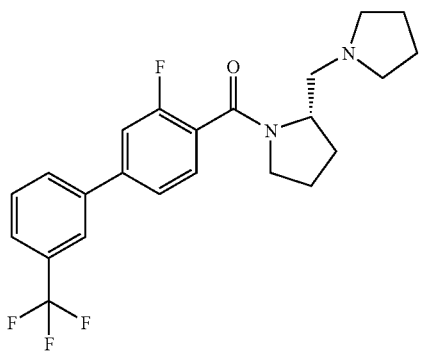

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 3-Trifluoromethyl benzene boronic acid. MS (M+H) 421.2

Example 72

(3-Fluoro-4'-trifluoromethyl-biphenyl-4-yl)-(2-(S)-pyrrolidin-1-ylmethyl-pyrrolidin-1-yl)-methanone

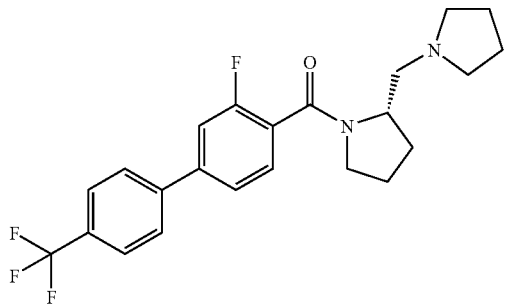

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 3-Trifluoromethyl benzene boronic acid. MS (M+H) 421.1

Example 73

3'-Fluoro-4'-(2-(S)-pyrrolidin-1-ylmethyl-pyrrolidine-1-carbonyl)-biphenyl-3-carbonitrile

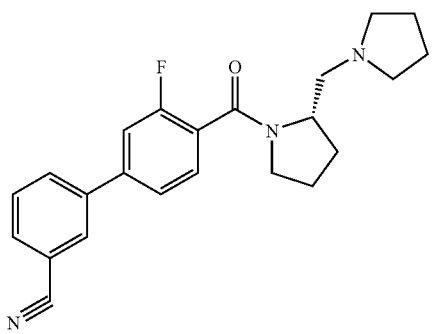

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 3-Cyanobenzene boronic acid. MS (M+H) 378.2

Example 74

(3-Fluoro-3'-trifluoromethoxy-biphenyl-4-yl)-(2-(S)-pyrrolidin-1-ylmethyl-pyrrolidin-1-yl)-methanone

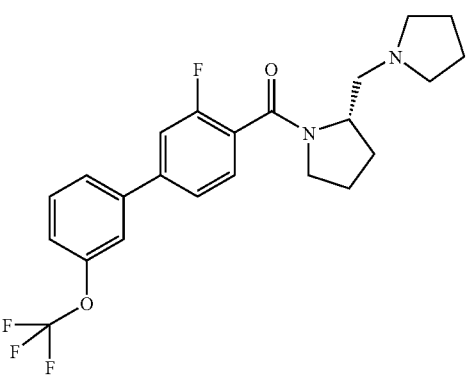

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 3-Trifluoromethoxybenzene boronic acid. MS (M+H) 437.1

Example 75

(3-Fluoro-4'-trifluoromethoxy-biphenyl-4-yl)-(2-(S)-pyrrolidin-1-ylmethyl-pyrrolidin-1-yl)-methanone

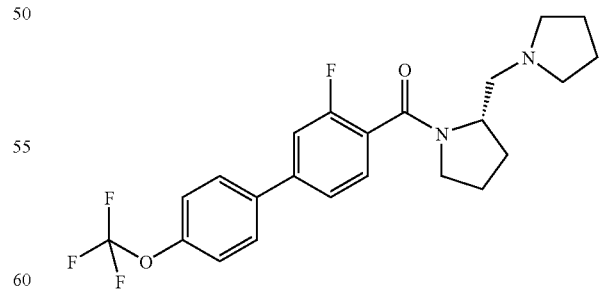

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 4-Trifluoromethoxybenzene boronic acid. MS (M+H) 437.1

Example 76

(3-Fluoro-2',4'-dimethoxy-biphenyl-4-yl)-(2-(S)-pyrrolidin-1-ylmethyl-pyrrolidin-1-yl)-methanone

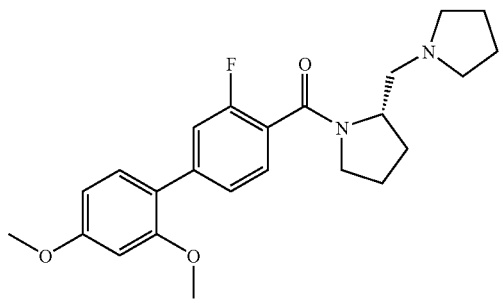

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 2,4-Dimethoxybenzene boronic acid. MS (M+H) 413.2

Example 77

(3-Fluoro-4'-methoxy-biphenyl-4-yl)-(2-(S)-pyrrolidin-1-ylmethyl-pyrrolidin-1-yl)-methanone

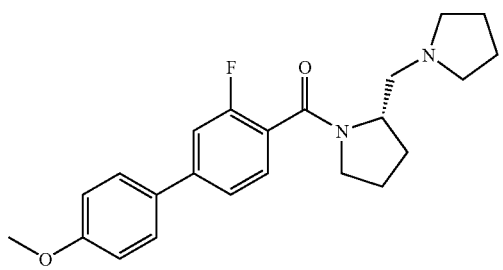

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 4-Methoxybenzene boronic acid. MS (M+H) 383.2

Example 78

(3-Fluoro-3',4'-dimethoxy-biphenyl-4-yl)-(2-(S)-pyrrolidin-1-ylmethyl-pyrrolidin-1-yl)-methanone

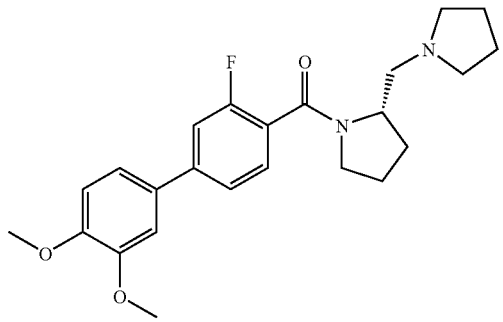

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 3,4-Dimethoxybenzene boronic acid. MS (M+H) 413.2

Example 79

(3,4'-Difluoro-biphenyl-4-yl)-(2-(S)-pyrrolidin-1-ylmethyl-pyrrolidin-1-yl)-methanone

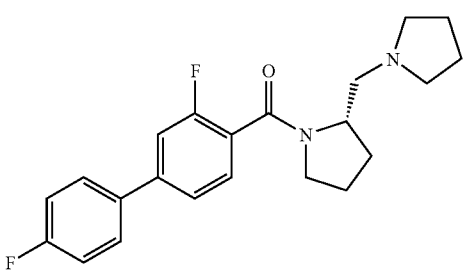

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 4-Fluorobenzene boronic acid. MS (M+H) 371.2

Example 80

(4-Benzo[1,3]dioxol-5-yl-2-fluoro-phenyl)-(2-(S)-pyrrolidin-1-ylmethyl-pyrrolidin-1-yl)-methanone

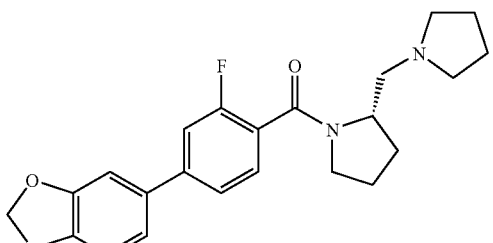

The title compound is prepared in a manner substantially analogous to Procedure SS starting from (4-bromo-2-fluorophenyl)-(2-(S)-pyrrolidin-1-ylmethyl-pyrrolidin-1-yl)-methanone and 3,4-Methylenedioxybenzene boronic acid. MS (M+H) 397.2

Example 81

[4-(2,3-Dihydro-benzo[1,4]dioxin-6-yl)-2-fluoro-phenyl]-(2-(S)-pyrrolidin-1-ylmethyl-pyrrolidin-1-yl)-methanone

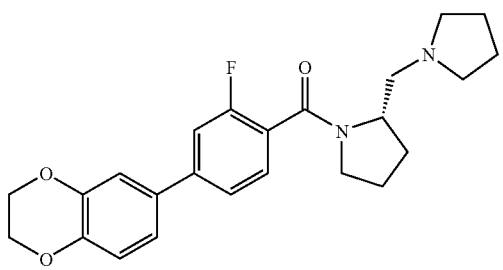

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 2,3-Dihydro-1,4-benzodioxin-6-yl boronic acid. MS (M+H) 411.2

Example 82

(3-Fluoro-3'-pyrrolidin-1-yl-biphenyl-4-yl)-(2-(S)-pyrrolidin-1-ylmethyl-pyrrolidin-1-yl)-methanone

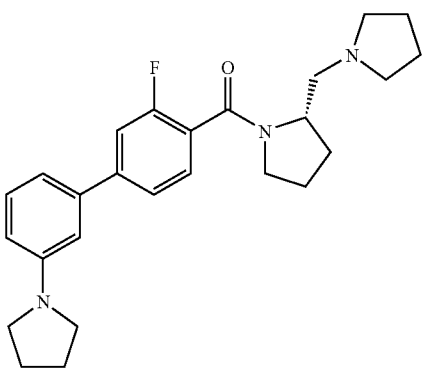

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 3-Pyrrolidine benzene boronic acid. MS (M+H) 422.2

Example 83

(3-Fluoro-3'-methanesulfonyl-biphenyl-4-yl)-(2-(S)-pyrrolidin-1-ylmethyl-pyrrolidin-1-yl)-methanone

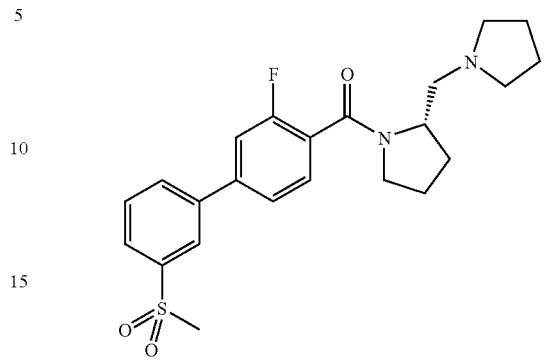

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 3-Methylsulfonyl benzene boronic acid. MS (M+H) 431.1

Example 84

(4'-Ethanesulfonyl-3-fluoro-biphenyl-4-yl)-(2-(S)-pyrrolidin-1-ylmethyl-pyrrolidin-1-yl)-methanone

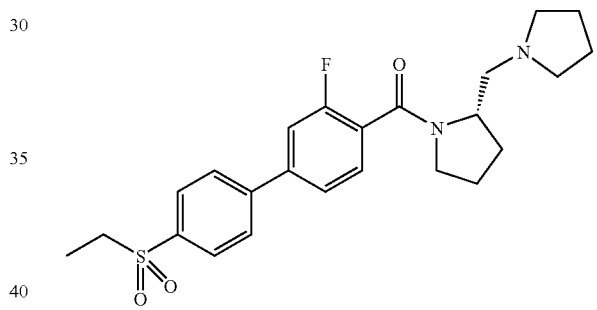

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 4-Ethylsulfonyl benzene boronic acid. MS (M+H) 445.2

Example 85

(3-Fluoro-4'-methanesulfinyl-biphenyl-4-yl)-(2-(S)-pyrrolidin-1-ylmethyl-pyrrolidin-1-yl)-methanone

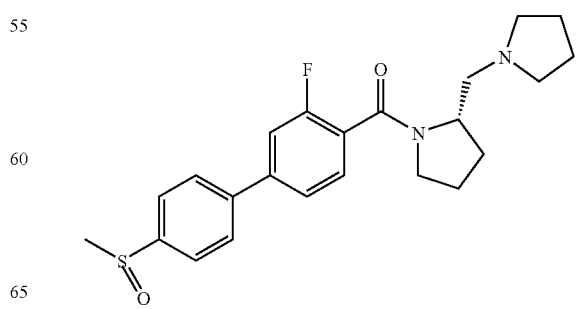

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 4-Methylsulfinyl benzene boronic acid. MS (M+H) 415.1

Example 86

(2-Fluoro-4-pyrimidin-5-yl-phenyl)-(2-(S)-pyrrolidin-1-ylmethyl-pyrrolidin-1-yl)-methanone

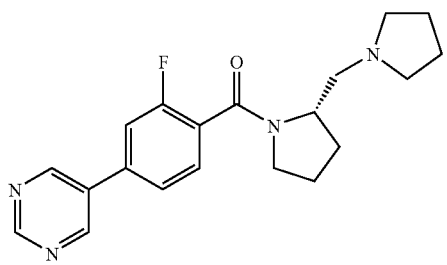

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 5-Pyrimidine boronic acid. MS (M+H) 355.2

Example 87

[2-Fluoro-4-(2-methoxy-pyrimidin-5-yl)-phenyl]-(2-(S)-pyrrolidin-1-ylmethyl-pyrrolidin-1-yl)-methanone

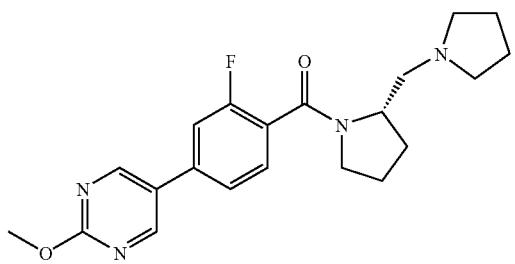

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 2-Methoxy-5-pyrimidine boronic acid. MS (M+H) 385.2

Example 88

[2-Fluoro-4-(6-methoxy-pyridin-3-yl)-phenyl]-(2-(S)-pyrrolidin-1-ylmethyl-pyrrolidin-1-yl)-methanone

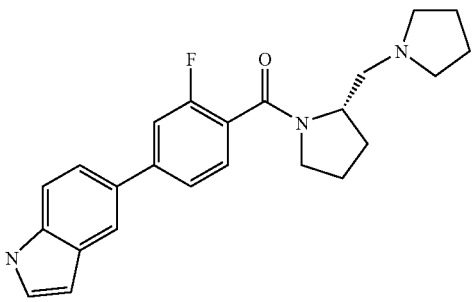

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 2-Methoxy-5-pyridine boronic acid. MS (M+H) 384.2

Example 89

[2-Fluoro-4-(1H-indol-5-yl)-phenyl]-(2-(S)-pyrrolidin-1-ylmethyl-pyrrolidin-1-yl)-methanone

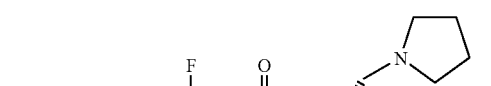

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 5-Indole boronic acid. MS (M+H) 392.2

Example 90

(2-Fluoro-4-quinolin-3-yl-phenyl)-(2-(S)-pyrrolidin-1-ylmethyl-pyrrolidin-1-yl)-methanone

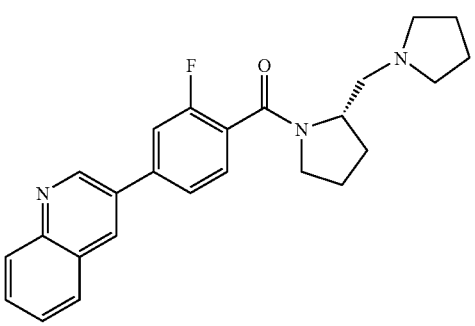

The title compound is prepared in a manner substantially analogous to Procedure SS starting from (4-bromo-2-fluoro-phenyl)-(2-(S)-pyrrolidin-1-ylmethyl-pyrrolidin-1-yl)-methanone and 2-Quinoline boronic acid. MS (M+H) 404.2

Intermediate Preparation 35

2-(R)-Methyl-1-(2-(S)-pyrrolidinylmethyl)pyrrolidine

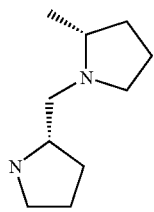

(S) BOC proline (CAS 15761-39-4) and 2-(R)Methyl-pyrrolidine hydrochloride (CAS 135324-85-5) are coupled in a manner substantially analogous to Procedure B' in dichloromethane to give 2(S)-(2(R)-Methyl-pyrrolidine-1-carbonyl)-pyrrolidine-1-carboxylic acid tert-butyl ester. The material is deprotected by stirring in dichloromethane at 5-10° C. while trifluoroacetic acid (10 eq,) is added and then stirred at room temperature for 18 hours. Reaction is concentrated, is dissolved in $H_2O$, pH is adjusted to 8-9 with $K_2CO_3$, and is extracted several times with $CH_2Cl_2$. The extracts are combined, dried ($Na_2SO_4$) and concentrated in vacuo to give (2(R)-Methyl-pyrrolidin-1-yl)-pyrrolidin-2-yl-methanone.
A 1 M Lithium Aluminum Hydride/THF solution (3 eq.) is diluted with an equal volume of THF and stirred under $N_2$ as a THF solution of (2(R)-methyl-pyrrolidin-1-yl)-pyrrolidin-2-yl-methanone is added dropwise, allowing the reaction to mildly exotherm. The reaction mixture is stirred at 40° C. for 45 minutes, then at room temperature 18 hours. The mixture is cooled in an ice bath and is quenched with $H_2O$ (3 eq.), 4 N NaOH (3 eq.), then $H_2O$ (9 eq.) while keeping reaction temperature less than 15° C. The mixture is stirred overnight, filtered and the precipitate is washed three times with THF. The filtrate and washes are combined and concentrated to give 2-(R)-methyl-1-(2-(S)-pyrrolidinylmethyl)pyrrolidine. MS (ES+) 169.3 (M+H)+ The title compound is used as such or is purified by SCX chromatography or distillation.

Example 91

(3-Fluoro-4'-methanesulfonyl-biphenyl-4-yl)-[2-(S)-(2-(R)-methyl-pyrrolidin-1-ylmethyl)-pyrrolidin-1-yl]-methanone

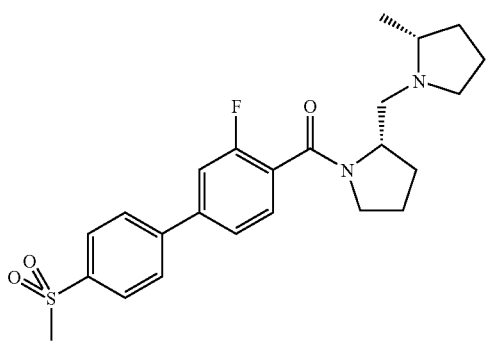

The title compound is prepared in a manner substantially analogous to Procedure A', T' and B' starting from 4-bromo-2-fluoro-benzoic acid, 4-methanesulfonylphenyl boronic acid and 2-(R)-Methyl-1-(2-(S)-pyrrolidinylmethyl)pyrrolidine. MS (M+H) 445.2. Alternatively, the title compound maybe prepared by methylation of 3'-fluoro-4-[(2-(R)-methyl-1-(2-(S)-pyrrolidinylmethyl)pyrrolidine-1-carbonyl]-biphenyl-4-sulfinic acid using NaH and iodomethane at 0° C.

Example 92

(4'-Ethanesulfonyl-3-fluoro-biphenyl-4-yl)-[2-(S)-(2-(R)-methyl-pyrrolidin-1-ylmethyl)-pyrrolidin-1-yl]-methanone

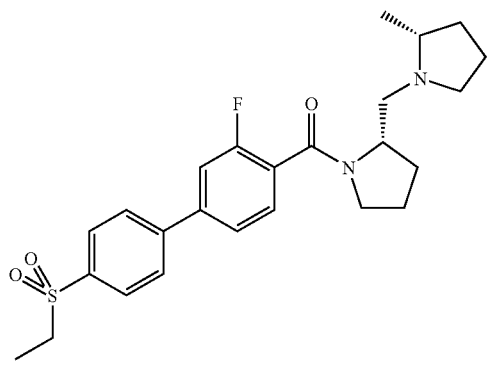

The title compound is prepared in a manner substantially analogous to Procedure A', T' and B' starting from 4-bromo-2-fluoro-benzoic acid, 4-ethanesulfonylphenyl boronic acid and 2-(R)-Methyl-1-(2-(S)-pyrrolidinylmethyl)pyrrolidine. MS (M+H) 459.2

Example 93

[2-(2,5-trans-Dimethyl-pyrrolidin-1-ylmethyl)-pyrrolidin-1-yl]-(4'-trifluoromethyl-biphenyl-4-yl)-methanone

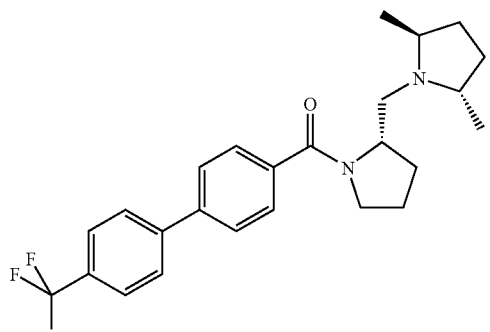

The title compound is prepared in a manner substantially analogous to Procedure RR starting from (2-(S)-Hydroxymethyl-pyrrolidin-1-yl)-(4'-trifluoromethyl-biphenyl-4-yl)-methanone and trans-2,5-dimethyl-pyrrolidine. MS (M+H) 431.2

Example 94

[2-(2,5-cis-Dimethyl-pyrrolidin-1-ylmethyl)-pyrrolidin-1-yl]-(4'-trifluoromethyl-biphenyl-4-yl)-methanone

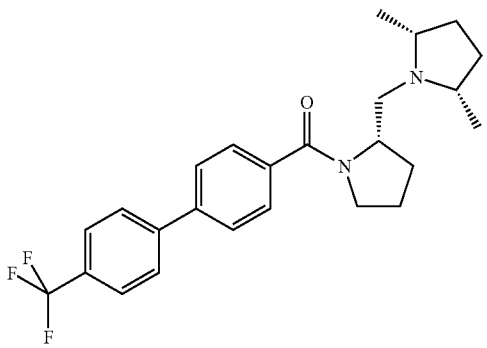

The title compound is prepared in a manner substantially analogous to Procedure RR starting from (2-(S)-Hydroxymethyl-pyrrolidin-1-yl)-(4'-trifluoromethyl-biphenyl-4-yl)-methanone and mixture of cis and trans-2,5-dimethyl-pyrrolidine. MS (M+H) 431.2

Intermediate Preparation 36

(2-(R)-Hydroxymethyl-pyrrolidin-1-yl)-(4'-trifluoromethyl-biphenyl-4-yl)-methanone

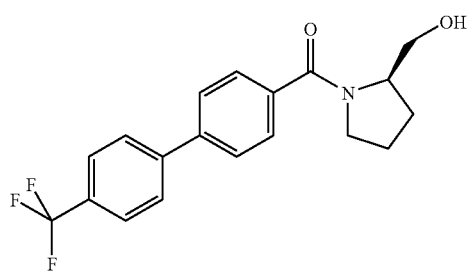

The title compound is prepared in a manner substantially analogous to Procedure B' from 4'-trifluoromethyl-biphenyl-4-carboxylic acid, lithium salt using (R)-2-pyrrolidine methanol as the amine. MS (ES+) 350.2

Example 95

(2-(R)-Pyrrolidin-1-ylmethyl-pyrrolidin-1-yl)-(4'-trifluoromethyl-biphenyl-4-yl)-methanone

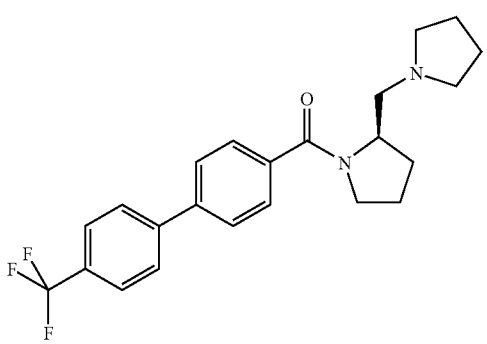

The title compound is prepared in a manner substantially analogous to Procedure RR starting from (2-(R)-hydroxymethyl-pyrrolidin-1-yl)-(4'-trifluoromethyl-biphenyl-4-yl)-methanone and pyrrolidine. MS (M+H) 403.2

Example 96

[2-(S)-(2-(R)-Ethyl-pyrrolidin-1-ylmethyl)-pyrrolidin-1-yl]-(4'-trifluoromethyl-biphenyl-4-yl)-methanone

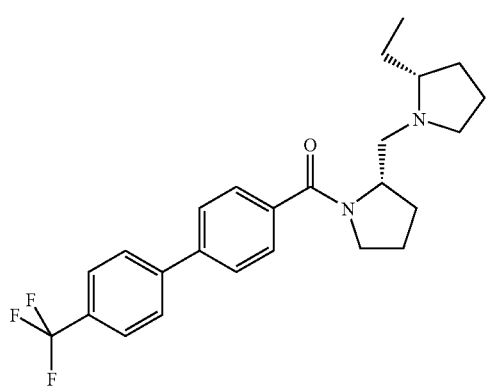

The title compound is prepared in a manner substantially analogous to Procedure RR starting from (2-(S)-hydroxymethyl-pyrrolidin-1-yl)-(4'-trifluoromethyl-biphenyl-4-yl)-methanone and 2-(R)-ethyl-pyrrolidine (CAS 460748-80-5) MS (M+H) 431.3.

Example 97

[2-(S)-(2-(S)-Fluoromethyl-pyrrolidin-1-ylmethyl)-pyrrolidin-1-yl]-(4'-trifluoromethyl-biphenyl-4-yl)-methanone

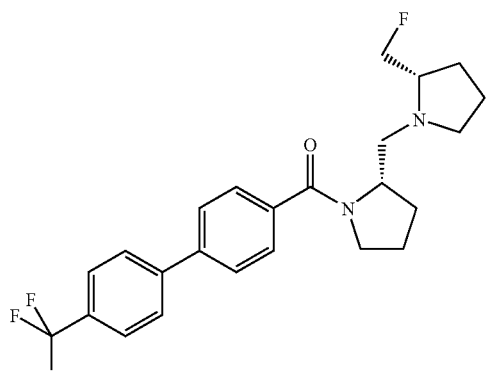

The title compound is prepared in a manner substantially analogous to Procedure RR starting from (2-(S)-hydroxymethyl-pyrrolidin-1-yl)-(4'-trifluoromethyl-biphenyl-4-yl)-methanone and 2-(S)-Fluoromethyl-pyrrolidine (CAS 460748-85-0) MS (M+H) 435.2

Example 98

(4'-methanesulfonyl-biphenyl-4-yl)-[2-(S)-(2-(R)-methyl-pyrrolidin-1-ylmethyl)-pyrrolidin-1-yl]-methanone

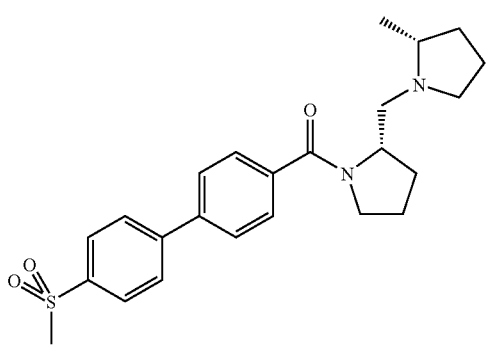

The title compound is prepared in a manner substantially analogous to Procedure B' starting from 4'-methanesulfonyl-biphenyl-4-carboxylic acid (CAS 16734-98-8) and 2-(R)-Methyl-1-(2-(S)-pyrrolidinylmethyl)pyrrolidine. MS (M+H) 427.2

Example 99

(4'-Cyclopropanecarbonyl-3-fluoro-biphenyl-4-yl)-(2-(S)-pyrrolidin-1-ylmethyl-pyrrolidin-1-yl)-methanone

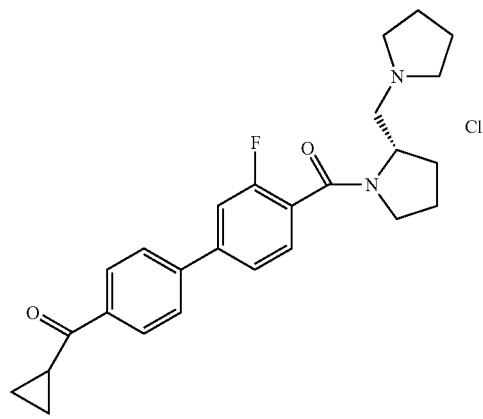

The title compound is prepared in a manner substantially analogous to Procedures P' and FF starting from (4-Bromo-2-fluoro-phenyl)-(2-(S)-pyrrolidin-1-ylmethyl-pyrrolidin-yl)methanone and commercially available (4-Bromo-phenyl)-cyclopropyl-methanone and bis(pinacolato) diboron. MS (M+H) 421.3

Example 100

Cyclopropyl-{3'-fluoro-4'-[2-(S)-(2-(R)-methyl-pyrrolidin-1-ylmethyl)-pyrrolidine-1-carbonyl]-biphenyl-4-yl}-methanone

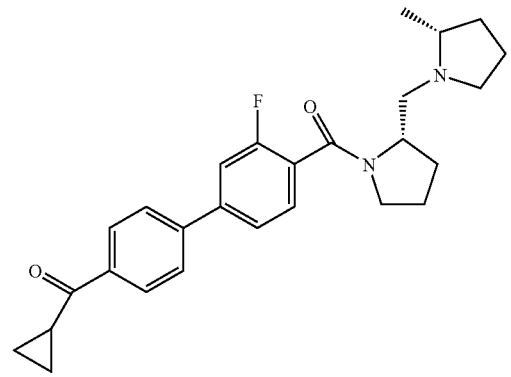

The title compound is prepared in a manner substantially analogous to Procedures QQ and B' starting from commercially available (4-Bromo-phenyl)-cyclopropyl-methanone and (4-carboxy-3-fluorophenyl)boronic acid (CAS#120153-08-4), then 2-(R)-Methyl-1-(2-(S)-pyrrolidinylmethyl)pyrrolidine. MS (M+H) 435.2

Intermediate Preparation 37

(4-Bromo-2,6-difluoro-phenyl)-(2-(R)-methyl-1-(2-(S)-pyrrolidinylmethyl)pyrrolidin-1-yl)-methanone

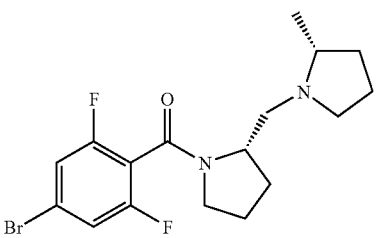

The title compound is prepared in a manner substantially analogous to Procedure E' from 2,6-difluoro-4-bromobenzoic acid (CAS 183065-68-1) and 2-(R)-Methyl-1-(2-(S)-pyrrolidinylmethyl)pyrrolidine. MS (FIA) 387/389 (MH+)

Example 101

(3,5-Difluoro-4'-methanesulfonyl-biphenyl-4-yl)-(2-(R)-methyl-1-(2-(S)-pyrrolidinylmethyl)pyrrolidin-1-yl)-methanone

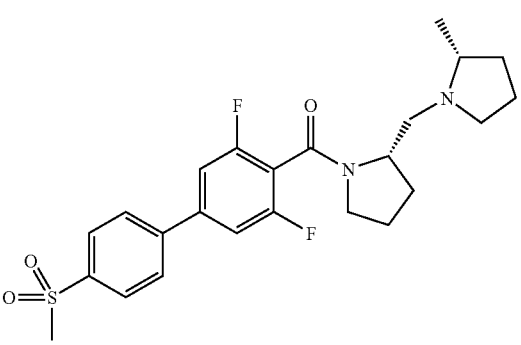

The title compound is prepared in a manner substantially analogous to Example 14 via Procedure F' from (4-bromo-2,6-difluoro-phenyl)-(2-(R)-methyl-1-(2-(S)-pyrrolidinylmethyl)pyrrolidin-1-yl)-methanone and 4-methanesulfonyl-benzene boronic acid (CAS 149104-88-1). MS (FIA) 463.0 (MH+).

Intermediate Preparation 38

(4-Bromo-2-fluoro-phenyl)-(2-(R)-methyl-1-(2-(S)-pyrrolidinylmethyl)pyrrolidin-1-yl)-methanone

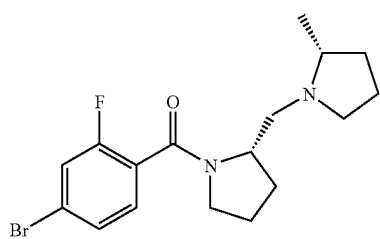

The title compound is prepared in a manner substantially analogous to Procedure PP from 4-bromo-2-fluoro-benzoic acid (CAS 112704-79-7) and 2-(R)-Methyl-1-(2-(S)-pyrrolidinylmethyl)pyrrolidine. MS (FIA) 369/371 (MH+)

Example 102

(2-Fluoro-4-[2-methoxy-pyrimidin-5-yl]-phenyl)-(2-(R)-methyl-1-(2-(S)-pyrrolidinylmethyl)pyrrolidin-1-yl)-methanone L-tartrate

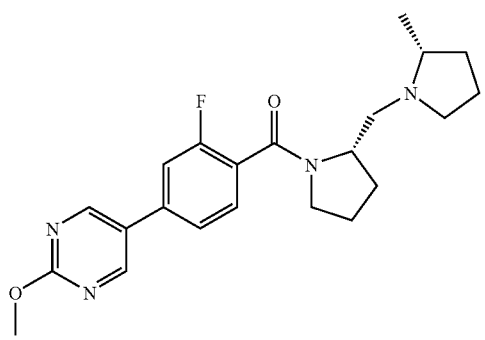

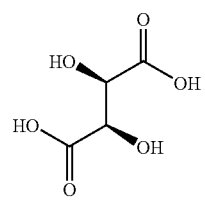

The title compound is prepared in a manner substantially analogous to Example 14 via Procedure F' from (4-bromo-2-fluoro-phenyl)-(2-(R)-methyl-1-(2-(S)-pyrrolidinylmethyl)pyrrolidin-1-yl)-methanone and 2-methoxypyrimidine-5-boronic acid (CAS 628692-15-9). The free base is dissolved in methanol with one equivalent of L-tartaric acid. the solvent is removed under reduced pressure and replaced with propan-2-ol. The mixture is heated until complete dissolution occurs and then allowed to cool. (2-Fluoro-4-[2-methoxy-pyrimidin-5-yl]-phenyl)-(2-(R)-methyl-1-(2-(S)-pyrrolidinylmethyl)pyrrolidin-1-yl)-methanone L-tartrate is collected by filtration MS (FIA) 399 (MH+)

Example 103

(2-Fluoro-4-[6-methoxy-pyridin-3-yl]-phenyl)-(2-(R)-methyl-1-(2-(S)-pyrrolidinylmethyl)pyrrolidin-1-yl)-methanone

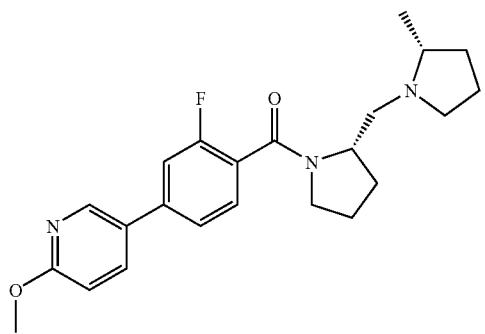

The title compound is prepared in a manner substantially analogous to Example 14 via Procedure F' from (4-bromo-2-fluoro-phenyl)-(2-(R)-methyl-1-(2-(S)-pyrrolidinylmethyl)pyrrolidin-1-yl)-methanone and 2-methoxypyridine-5-boronic acid (CAS 163105-89-3). MS (FIA) 398 (MH+)

Example 104

(2-Fluoro-4-pyridin-3-yl-phenyl)-(2-(R)-methyl-1-(2-(S)-pyrrolidinylmethyl)pyrrolidin-1-yl)-methanone

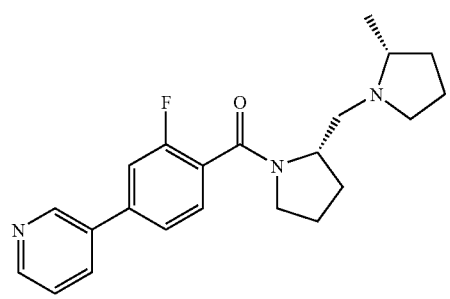

The title compound is prepared in a manner substantially analogous to Example 14 via Procedure F' from (4-bromo-2-fluoro-phenyl)-(2-(R)-methyl-1-(2-(S)-pyrrolidinylmethyl)pyrrolidin-1-yl)-methanone and pyridine-3-boronic acid (CAS 1692-25-7). MS (FIA) 368 (MH+)

Example 105

(3-Fluoro-4'-methylthio-biphenyl-4-yl)-(2-(R)-methyl-1-(2-(S)-pyrrolidinylmethyl)pyrrolidin-1-yl)-methanone

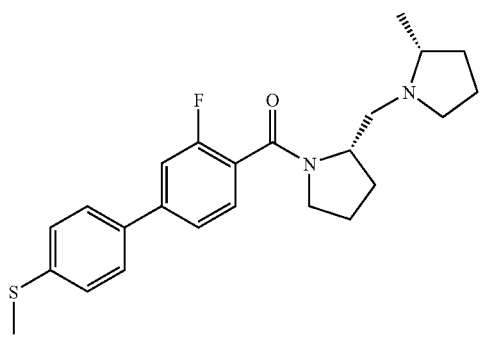

The title compound is prepared in a manner substantially analogous to Example 14 via Procedure F' from (4-bromo-2-fluoro-phenyl)-(2-(R)-methyl-1-(2-(S)-pyrrolidinylmethyl)pyrrolidin-1-yl)-methanone and 4-(methylthio)benzeneboronic acid (CAS 98546-51-1). MS (FIA) 413 (MH+)

Example 106

(3-Fluoro-4'-methanesulfinyl-biphenyl-4-yl)-(2-(R)-methyl-1-(2-(S)-pyrrolidinylmethyl)pyrrolidin-1-yl)-methanone

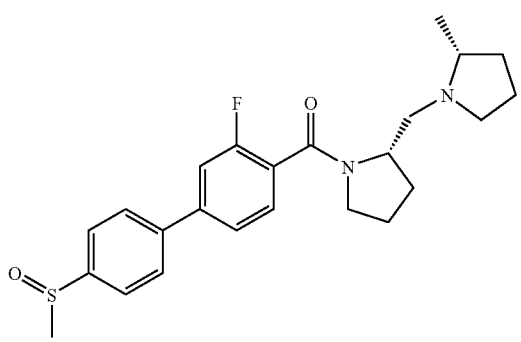

(3-Fluoro-4'-methylthio-biphenyl-4-yl)-(2-(R)-methyl-1-(2-(S)-pyrrolidinylmethyl)pyrrolidin-1-yl)-methanone is dissolved in Dioxane and stirred at room temperature. An aqueous solution of Oxone™ is added dropwise and the reaction monitored by TLC until the majority of the starting material is consumed. Reaction mixture is concentrated. The crude residue is purified by SCX chromatography (MeOH wash, then elution with 2M NH$_3$/MeOH to give partially purified material. This material is then purified by silica-gel column chromatography (gradient: 100% CH$_2$Cl$_2$ to 10% 2M NH$_3$ in MeOH/CH$_2$Cl$_2$) to give the title compound (94 mg, 76% yield). MS (FIA) 429 (MH+)

Intermediate Preparation 39

2-Fluoro-4-(4,4,5,5-tetramethyl-[1,3,2]dioxaborolan-2-yl)-benzoic acid

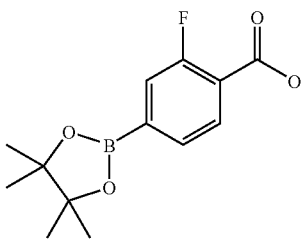

3-Fluoro-4-carboxy-phenylboronic acid (CAS 120153-08-4) (1.0 g, 5.4 mmol) and pinacol (0.645 g, 5.4 mmol) were stirred in Toluene/EtOH (1:1) (30 ml) with heating to give a thick white slurry. The mixture was concentrated under reduced pressure, toluene (30 ml) was added and the mixture was again concentrated under reduced pressure to a white solid. LCMS (−ve ion mode) showed a single peak trace with 265 (M−H RP). The material was dried under high vacuum overnight to give 1.42 g.

Intermediate Preparation 40

2-Fluoro-4-(4,4,5,5-tetramethyl-[1,3,2]dioxaborolan-2-yl)-phenyl-(2-(R)-methyl-1-(2-(S)-pyrrolidinylmethyl)pyrrolidin-1-yl)-methanone

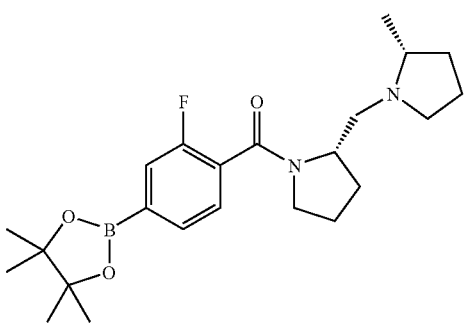

The title compound is prepared in a manner substantially analogous to Procedure PP from 2-fluoro-4-(4,4,5,5-tetramethyl-[1,3,2]dioxaborolan-2-yl)-benzoic acid and 2-(R)-Methyl-1-(2-(S)-pyrrolidinylmethyl)pyrrolidine. MS (FIA) 417 (MH+)

Example 107

3'-Fluoro-4-[(2-(R)-methyl-1-(2-(S)-pyrrolidinylmethyl)pyrrolidine-1-carbonyl]-biphenyl-4-sulfinic acid

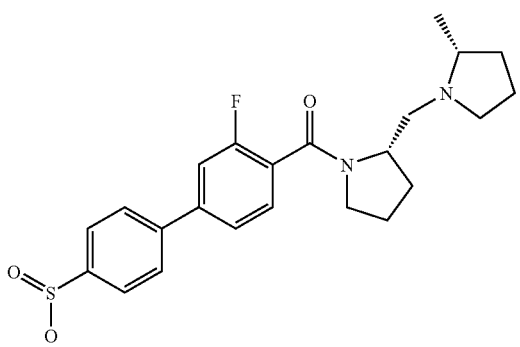

2-Fluoro-4-(4,4,5,5-tetramethyl-[1,3,2]dioxaborolan-2-yl)-phenyl-(2-(R)-methyl-1-(2-(S)-pyrrolidinylmethyl)pyrrolidin-1-yl)-methanone (0.782 g, 1.88 mmol), ethyl-4-bromobenzenesulfinate ester (CAS 6517-41-5) (0.75 g, 3.0 mmol) are dissolved in dry THF (50 ml) and dried potassium phosphate (1.9 g, 8.95 mmol) are added. The mixture is degassed with a nitrogen stream for 30 minutes, Pd(PPh$_3$)$_4$ (75 mg) is added and the mixture is heated to reflux overnight. The mixture is allowed to cool, filtered (Celite) and concentrated under reduced pressure. The residue is taken up in MeCN and absorbed onto SCX (2×10 g cartridges), washed with MeCN and eluted off with 25% Et$_3$N in MeCN. LCMS of this eluted material showed mostly RP as a mixture of ester (MH$^+$ 459) and sulfinic acid (MH$^+$ 431) due to hydrolysis in the LCMS eluent). The eluted material is concentrated under reduced pressure to 682 mg oil. The oil is dissolved in MeOH/water (4:1), NaHCO$_3$ (400 mg, 4.76 mmol) is added and the mixture is heated at 90° C. for 40 mins. FIA MS shows no ester remaining so the mixture is concentrated under reduced pressure and partitioned between aqueous and EtOAc. The aqueous phase is brought to Ph7 with dil. HCl (aq) and freeze-dried overnight. The freeze-dried residue is taken up in EtOH, filtered and concentrated to give 3'-fluoro-4-[(2-(R)-methyl-1-(2-(S)-pyrrolidinylmethyl)pyrrolidine-1-carbonyl]-biphenyl-4-sulfinic acid as a beige solid (440 mg). MS (FIA) 431 (MH$^+$)

Intermediate Preparation 41

4-(6-Ethanesulfonyl-pyridin-3-yl)-2-fluoro-benzoic acid

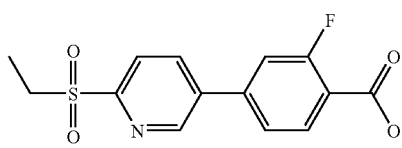

Procedure VV: To a stirring solution of 2-Ethanesulfonyl-5-iodo-pyridine (1.0 mmol) and (4-carboxy-3-fluorophenyl) boronic acid (1.3 mmol) in dioxane (0.1M), add dichloro[1,1'-bis(diphenylphosphino)ferrocene]palladium dichloromethane complex (0.03 mmol) and 2M aqueous sodium carbonate (3.0 mmol). Heat the reaction to reflux for 4 hours. After this time, remove the heat and concentrate in vacuo. Wash with dichloromethane while extracting with water. Acidify the aqueous layer with 1N hydrochloric acid and extract with 10% isopropanol/dichloromethane four times. Combine the organics, dry with sodium sulfate, decant and concentrate in vacuo. MS (m/e): 310.3 (M+1)

Example 108

[4-(6-Ethanesulfonyl-pyridin-3-yl)-2-fluoro-phenyl]-[2-(S)-(2-(R)-methyl-pyrrolidin-1-ylmethyl)-pyrrolidin-1-yl]-methanone dihydrochloride salt

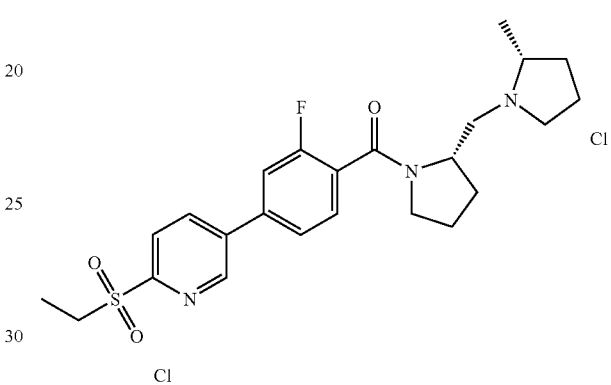

The title compound is prepared in a manner substantially analogous to Procedures CC, DD and AA starting from 4-(6-Ethanesulfonyl-pyridin-3-yl)-2-fluoro-benzoic acid and 2-(R)-Methyl-1-(2-(S)-pyrrolidinylmethyl)pyrrolidine. MS (m/e): 460.2 (M+1)

Example 109

(2,6-Difluoro-4-pyridin-3-yl-phenyl)-((S)-2-pyrrolidin-1-ylmethyl-pyrrolidin-1-yl)-methanone

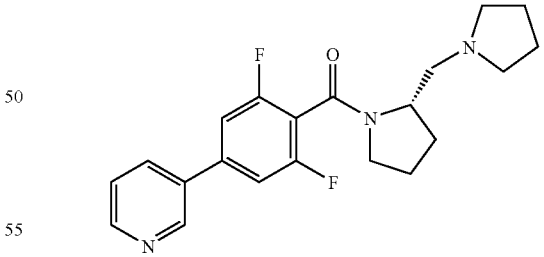

Procedure WW: To a stirred solution of (4-Bromo-2,6-difluoro-phenyl)-((S)-2-pyrrolidin-1-ylmethyl-pyrrolidin-1-yl)-methanone (100 mg, 0.268 mmol), sodium carbonate (85 mg, 0.802 mmol) and 3-pyridine boronic acid (164 mg, 1.34 mmol) in toluene (5 ml), water (1 ml) and ethanol (1.5 ml) under nitrogen is added Tetrakis (triphenylphosphine) palladium (0) (31.0 mg, 0.027 mmol). The reaction is heated at reflux for 48 h. The reaction is allowed to cool and bound to a SCX-2 cartridge (10 g). The cartridge is washed with one cartridge volume of dimethylformamide and two volumes of

Example 110

(2,6-Difluoro-4-pyrimidin-5-yl-phenyl)-((S)-2-pyrrolidin-1-ylmethyl-pyrrolidin-1-yl)-methanone

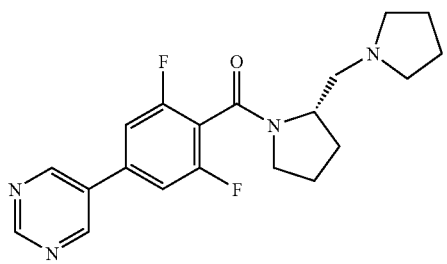

The title compound is prepared in a manner substantially analogous to Procedure WW starting from 5-pyrimidine boronic acid and (4-bromo-2,6-difluoro-phenyl)-((S)-2-pyrrolidin-1-ylmethyl-pyrrolidin-1-yl)-methanone to give 8 mg (8%). MS (ES+) 373 m/z

Example 111

(3,5-Difluoro-4'-methanesulfinyl-biphenyl-4-yl)-((S)-2-pyrrolidin-1-yl methyl-pyrrolidin-1-yl)-methan one

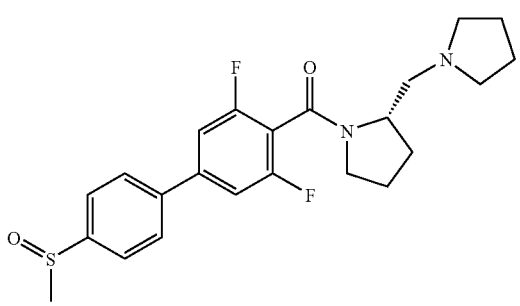

The title compound is prepared in a manner substantially analogous to Procedure WW starting from 4-(methylsulfinyl)phenyl boronic acid and (4-bromo-2,6-difluoro-phenyl)-((S)-2-pyrrolidin-1-ylmethyl-pyrrolidin-1-yl)-methanone to give 2 mg (2%). MS (ES+) 433 m/z methanol. The product is eluted using 2M ammonia in methanol. The ammonia/methanol solution is evaporated on a Genevac HT4. The sample is further purified by prep-LCMS. The resulting acetonitrile/water fractions are combined and evaporated using a Genevac to give 2.2 mg of a colourless oil (2%). MS (ES+) 372.2 m/z

Example 112

([2,6-Difluoro-4-(5-methoxy-pyridin-3-yl)-phenyl]-((S)-2-pyrrolidin-1-ylmethyl-pyrrolidin-1-yl)-methanone

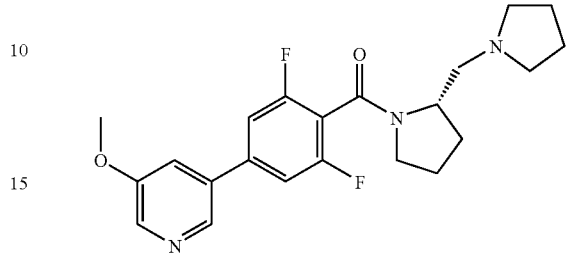

The title compound is prepared in a manner substantially analogous to Procedure WW starting from 3-methoxypyridine-5-boronic acid and (4-bromo-2,6-difluoro-phenyl)-((S)-2-pyrrolidin-1-ylmethyl-pyrrolidin-1-yl)-methanone to give 20 mg (19%). MS (ES+) 402 m/z

Example 113

[2-(S)-(2-(R)-Methyl-pyrrolidin-1-ylmethyl]-(4-pyrimidin-2-yl-phenyl)-methanone

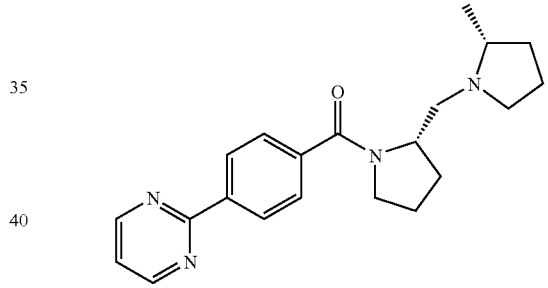

The title compound is prepared in a manner substantially analogous to General Procedure F' using [2-(S)-(2-(R)-Methyl-pyrrolidin-1-ylmethyl)-pyrrolidin-1-yl]-[4-(4,4,5,5-tetramethyl-[1,3,2]dioxaborolan-2-yl)-phenyl]-methanone (319 mg, 0.8 mmol) and 2-Bromo-pyrimidine (CAS 4595-60-2) (127 mg, 0.8 mmol) to give 137 mg (49% yield). MS (ES+) 351.0 (M+H)+

Intermediate 42

4-(6-Methoxy-pyridin-2-yl)-benzoic acid

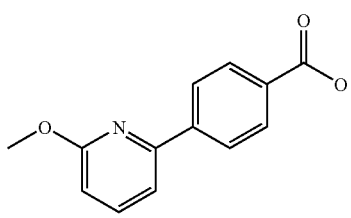

The title intermediate is prepared in a manner substantially analogous to General Procedure C' using 4-(6-Methoxy-pyridin-2-yl)-benzaldehyde (CAS 618092-16-3) and is confirmed by NMR. NMR (DMSO) 13.05 (s, 1H), 8.35-7.65 (m, 6H), 6.85 (m, 1H), 3.95 (s, 3H).

Example 114

[4-(6-Methoxy-pyridin-2-yl)-phenyl]-[2-(S)-(2-(R)-Methyl-pyrrolidin-1-ylmethyl)-pyrrolidin-1-yl]-methanone

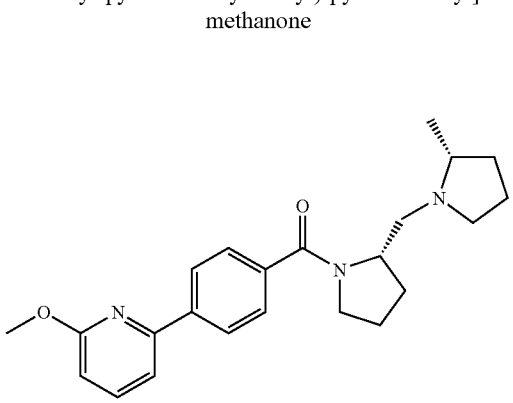

The title compound is prepared in a manner substantially analogous to General Procedure B' using 4-(6-Methoxy-pyridin-2-yl)-benzoic acid (573 mg, 2.5 mmol) and 2-(R)-methyl-1-(2-(S)-pyrrolidinylmethyl)pyrrolidine (337 mg, 2.0 mmol) to give 580 mg (76% yield). MS (ES+) 380.2 (M+H)+

Example 115

[2-Fluoro-4-(6-fluoro-pyridin-3-yl)-phenyl]-[2-(S)-(2-(R)-Methyl-pyrrolidin-1-ylmethyl)-pyrrolidin-1-yl]-methanone

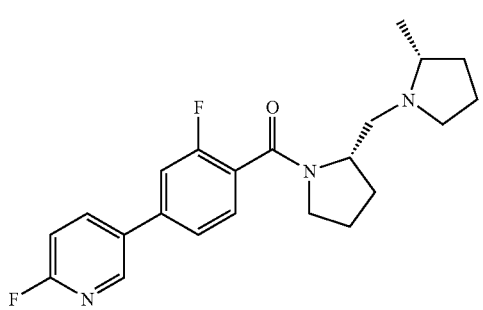

The title compound is prepared in a manner substantially analogous to General Procedure F' using (4-Bromo-2-fluoro-phenyl)-(2-(R)-methyl-1-(2-(S)-pyrrolidinylmethyl)pyrrolidin-1-yl)-methanone (454 mg, 1.23 mmol) and 2-fluoro-5-pyridine boronic acid (CAS 351019-18-6) (207 mg, 1.47 mmol) to give 386 nag (81% yield). MS (ES+) 386.2 (M+H)+

Intermediate 43

(4-Bromo-phenyl)-[2-(S)-(2-(R)-Methyl-pyrrolidin-1-ylmethyl)-pyrrolidin-1-yl]-methanone

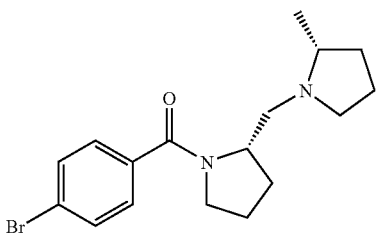

The title compound is prepared in a manner substantially analogous to General Procedure PP using commercially available 4-bromo benzoic acid, 2-(R)-methyl-1-(2-(S)-pyrrolidinylmethyl)pyrrolidine, and thionyl chloride in place of oxalyl chloride. (MS (ES+) 352.3 (M+H)+

Example 116

[4-(6-Fluoro-pyridin-3-yl)-phenyl]-[2-(S)-(2-(R)-Methyl-pyrrolidin-1-ylmethyl)-pyrrolidin-1-yl]-methanone

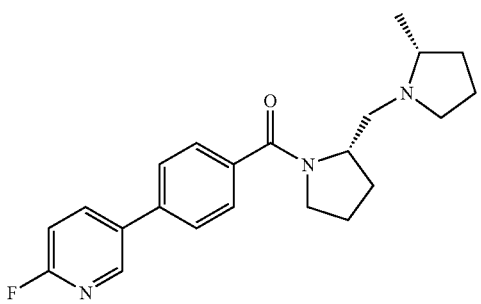

The title compound is prepared in a manner substantially analogous to General Procedure F' using (4-Bromo-phenyl)-[2-(S)-(2-(R)-Methyl-pyrrolidin-1-ylmethyl)-pyrrolidin-1-yl]-methanone and (2-fluoro-5-pyridine boronic acid (CAS 351019-18-6) to give 324 mg (63% yield). MS (ES+) 368.3 (M+H)+

87

Intermediate 44

[2-(S)-(2-(R)-Methyl-pyrrolidin-1-ylmethyl)-pyrrolidin-1-yl]-[4-(4,4,5,5-tetramethyl-[1,3,2]dioxaborolan-2-yl)-phenyl]-methanone

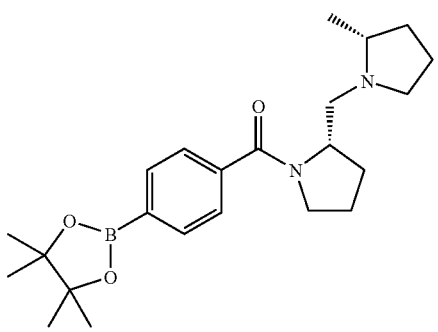

The title intermediate is prepared in a manner substantially analogous General Procedure PP, except thionyl chloride is used instead of oxalyl chloride, using 2-(R)-methyl-1-(2-(S)-pyrrolidinylmethyl)pyrrolidine and 4-(4,4,5,5-tetramethyl-[1,3,2]dioxaborolan-2-yl)-benzoic acid (CAS 180516-87-4). MS (ES+) 399.5 (M+H)+

88

Example 117

[4-(6-Methyl-pyridazin-3-yl)-phenyl]-[2-(S)-(2-(R)-Methyl-pyrrolidin-1-ylmethyl)-pyrrolidin-1-yl]-methanone

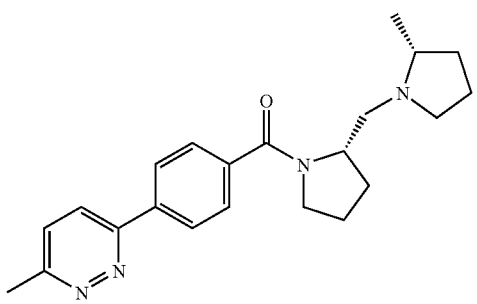

The title compound is prepared in a manner substantially analogous to General Procedure F' using [2-(S)-(2-(R)-Methyl-pyrrolidin-1-ylmethyl]-[4-(4,4,5,5-tetramethyl-[1,3,2] dioxaborolan-2-yl)-phenyl]-methanone (399 mg, 1.0 mmol) and 3-Iodo-6-methyl-pyridazine (CAS 1618-47-9) (220 mg, 1.0 mmol) to give 125 mg (34% yield). MS (ES+) 365.2 (M+H)+

Further embodiments of the invention include the compounds of formulae X1 to X115.

| Formula Number | Structure |
|---|---|
| X1 | 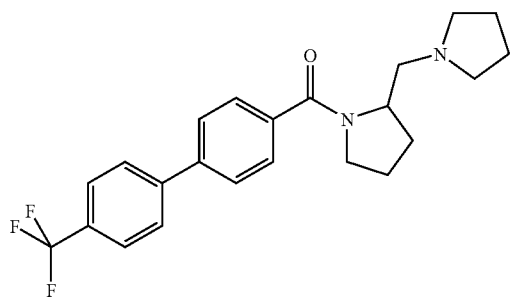 |
| X2 | 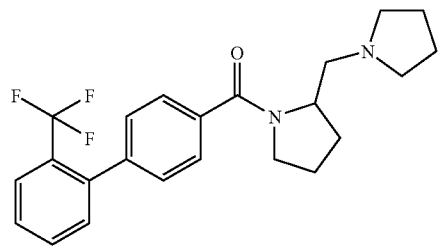 |
| X3 | 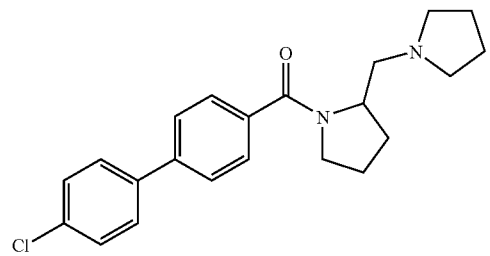 |

-continued
| Formula Number | Structure |
|---|---|
| X4 | 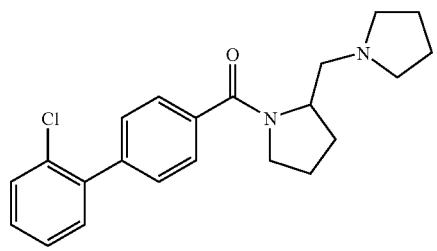 |
| X5 | 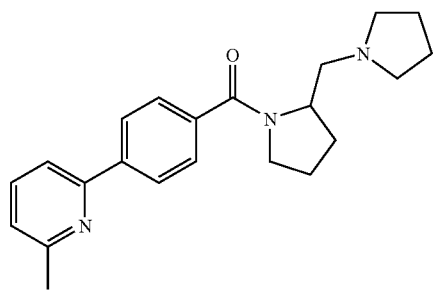 |
| X6 | 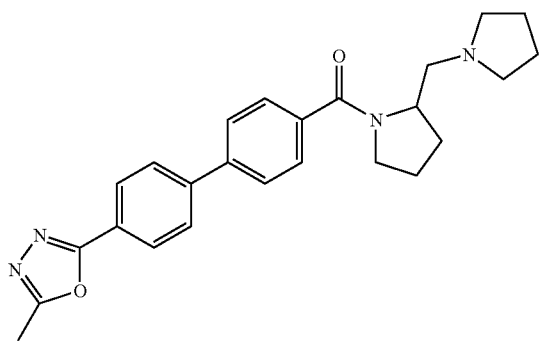 |
| X7 | 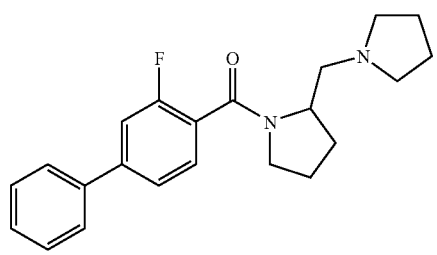 |
| X8 | 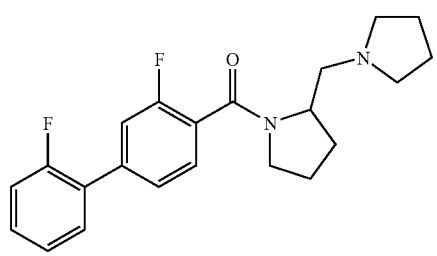 |

-continued
| Formula Number | Structure |
|---|---|
| X9 | 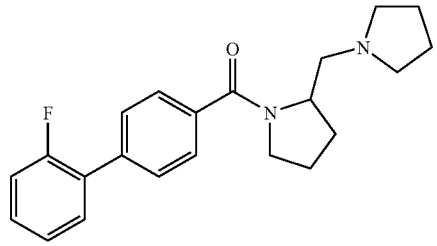 |
| X10 | 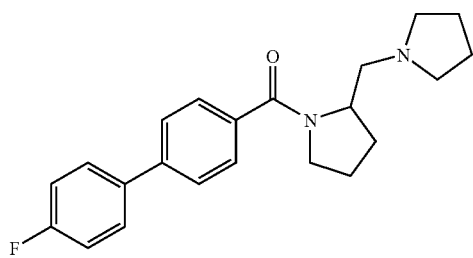 |
| X11 | 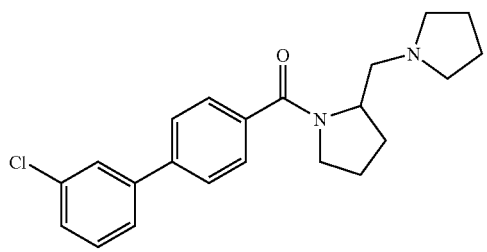 |
| X12 | 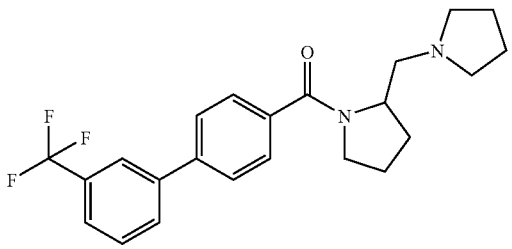 |
| X13 | 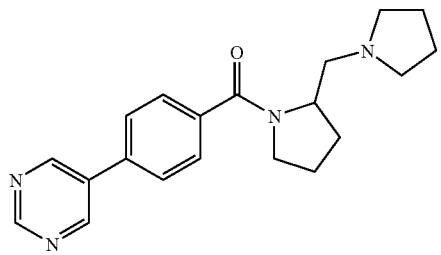 |
| X14 | 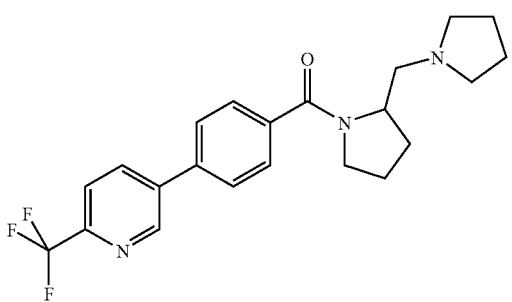 |

| Formula Number | Structure |
|---|---|
| X15 | 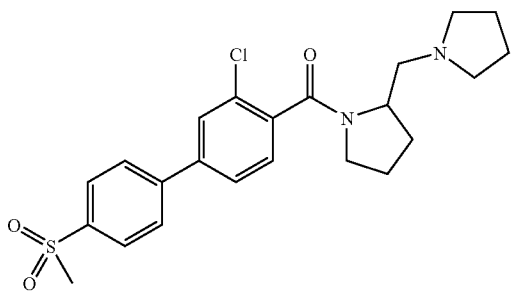 |
| X16 | 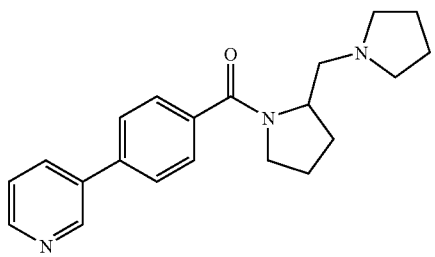 |
| X17 | 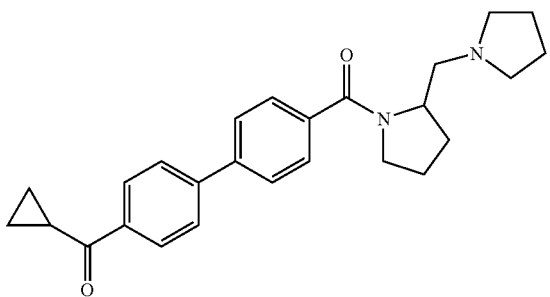 |
| X18 | 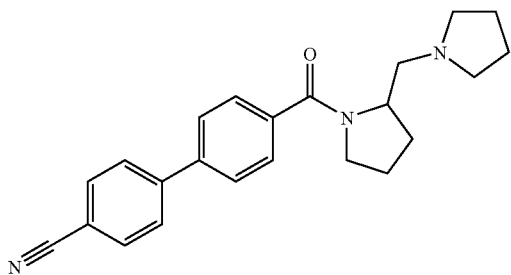 |
| X19 | 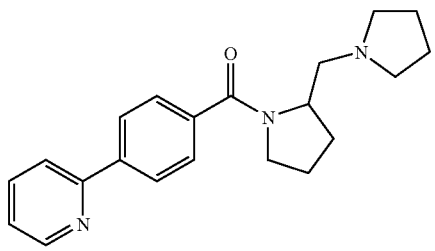 |

-continued
| Formula Number | Structure |
|---|---|
| X20 | 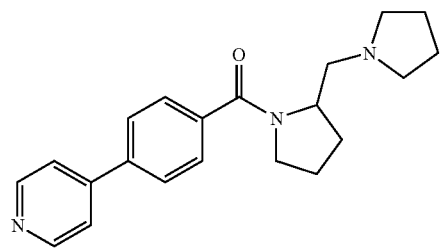 |
| X21 | 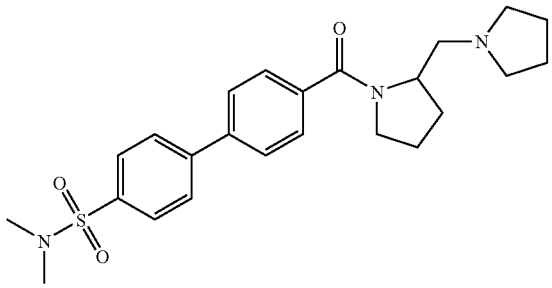 |
| X22 | 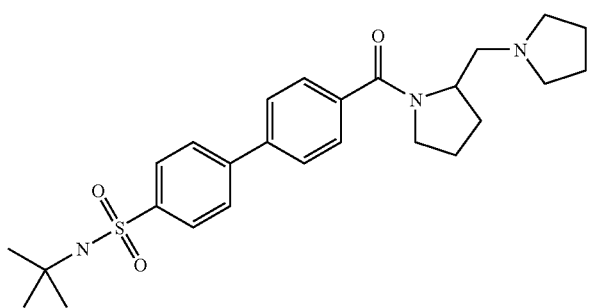 |
| X23 | 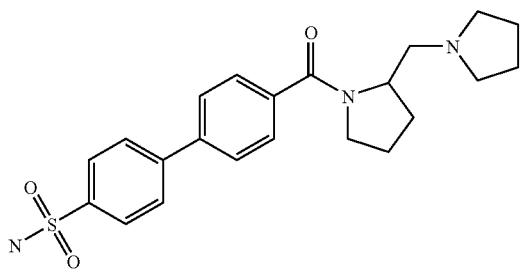 |
| X24 | 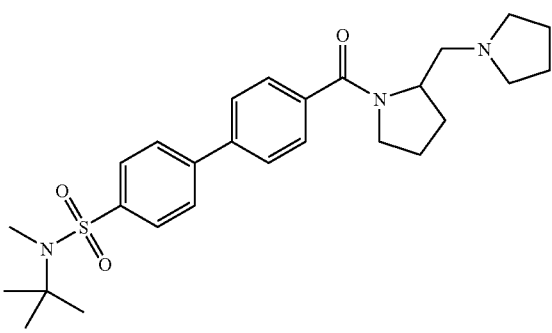 |

-continued
| Formula Number | Structure |
|---|---|
| X25 | 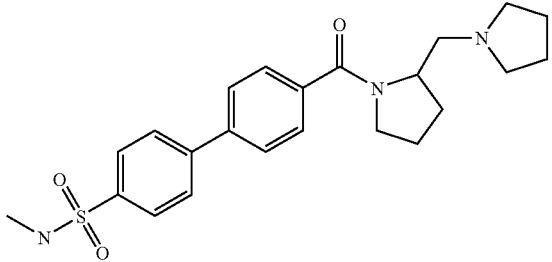 |
| X26 | 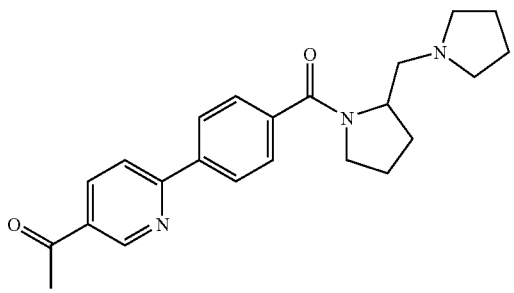 |
| X27 | 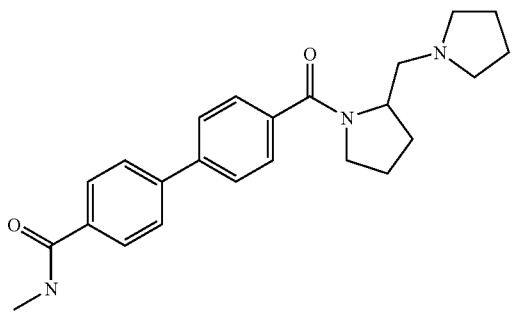 |
| X28 | 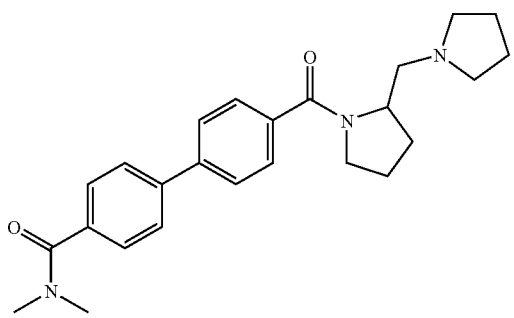 |
| X29 | 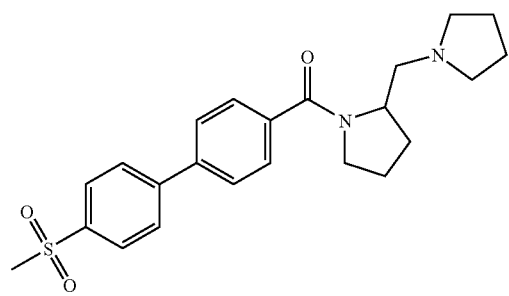 |

-continued
| Formula Number | Structure |
|---|---|
| X30 | 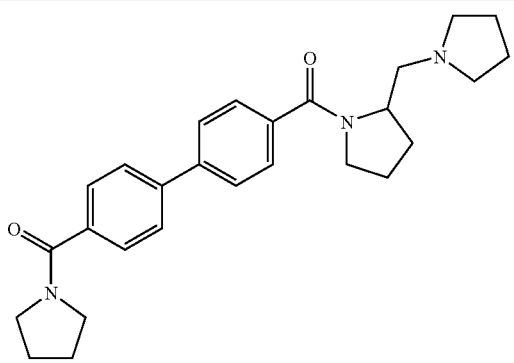 |
| X31 | 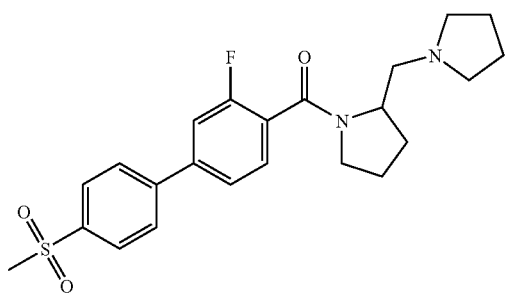 |
| X32 | 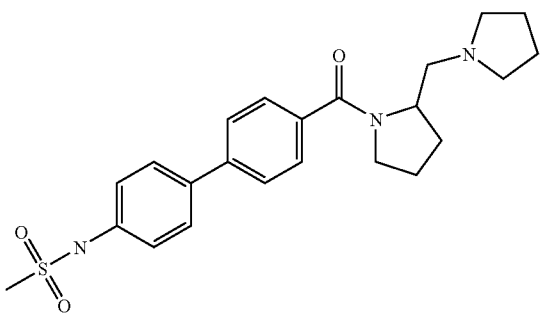 |
| X33 | 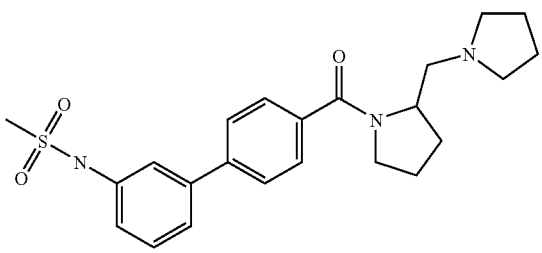 |
| X34 | 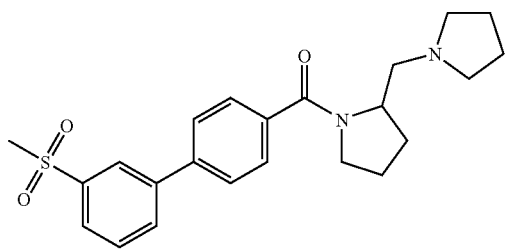 |

-continued
| Formula Number | Structure |
|---|---|
| X35 | 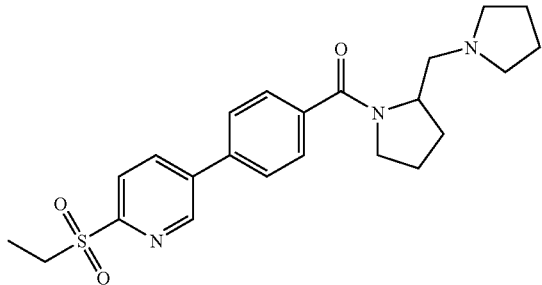 |
| X36 | 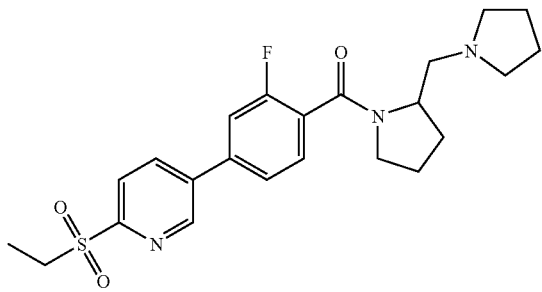 |
| X37 | 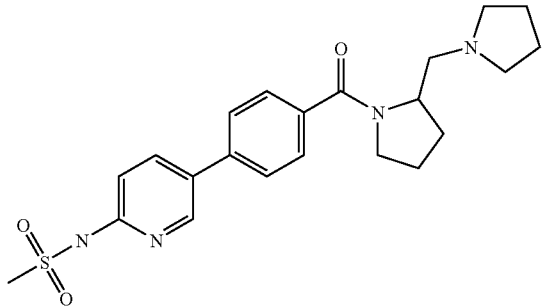 |
| X38 | 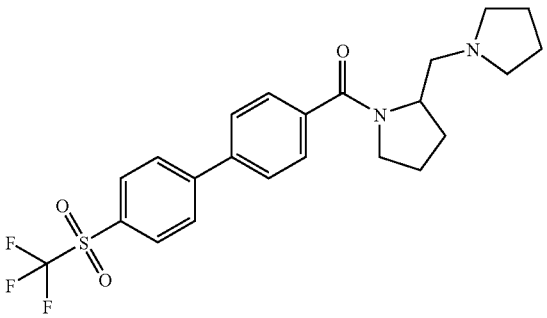 |
| X39 | 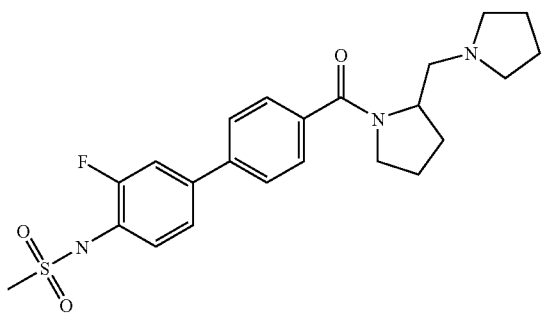 |

| Formula Number | Structure |
|---|---|
| X40 | 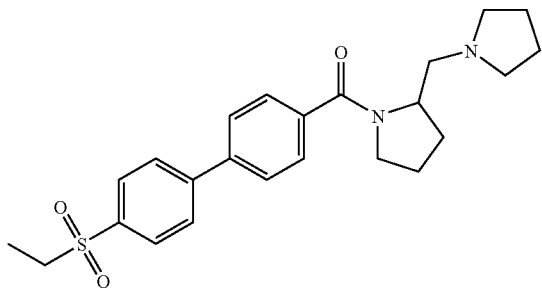 |
| X41 | 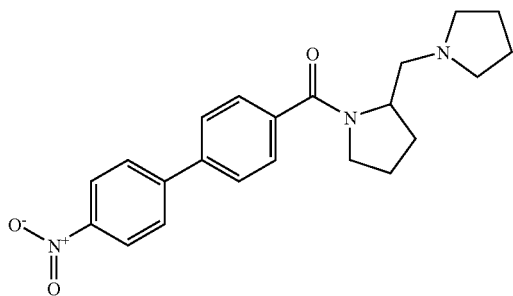 |
| X42 | 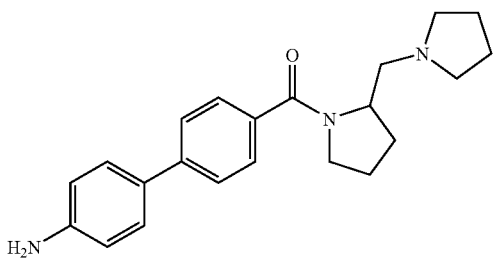 |
| X43 | 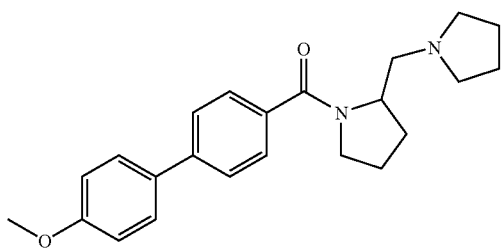 |
| X44 | 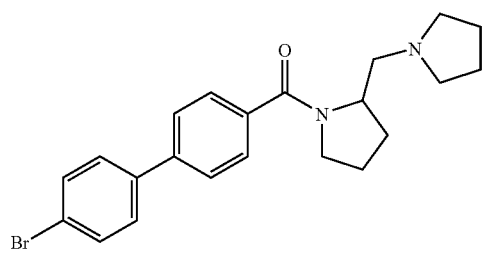 |

| Formula Number | Structure |
|---|---|
| X45 | *(2-nitrobiphenyl-4-yl)(2-(pyrrolidin-1-ylmethyl)pyrrolidin-1-yl)methanone)* |
| X46 | *(4'-ethylbiphenyl-4-yl)(2-(pyrrolidin-1-ylmethyl)pyrrolidin-1-yl)methanone* |
| X47 | *biphenyl-4-yl(2-(pyrrolidin-1-ylmethyl)pyrrolidin-1-yl)methanone* |
| X48 | *(4'-propylbiphenyl-4-yl)(2-(pyrrolidin-1-ylmethyl)pyrrolidin-1-yl)methanone* |
| X49 | *(4'-(2-(piperidin-1-yl)ethoxy)biphenyl-4-yl)(2-(pyrrolidin-1-ylmethyl)pyrrolidin-1-yl)methanone* |
| X50 | *(4'-tert-butylbiphenyl-4-yl)(2-(pyrrolidin-1-ylmethyl)pyrrolidin-1-yl)methanone* |

-continued
| Formula Number | Structure |
|---|---|
| X51 | 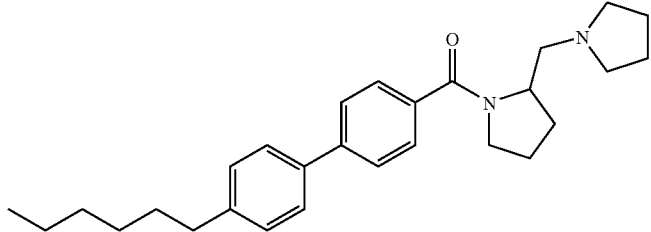 |
| X52 | 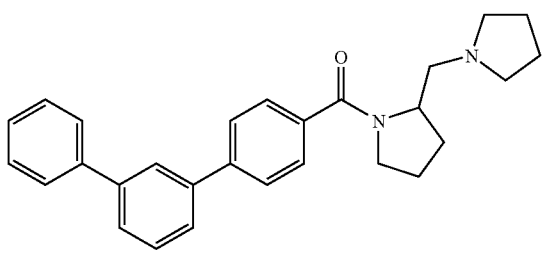 |
| X53 | 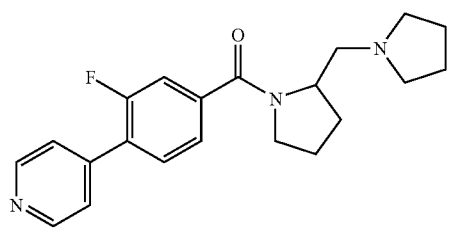 |
| X54 | 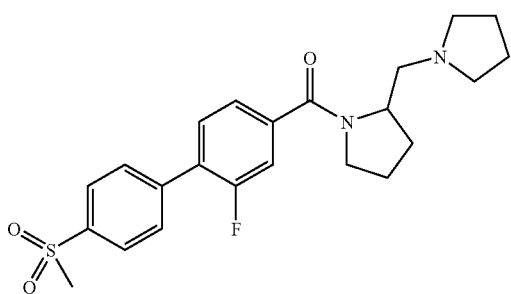 |
| X55 | 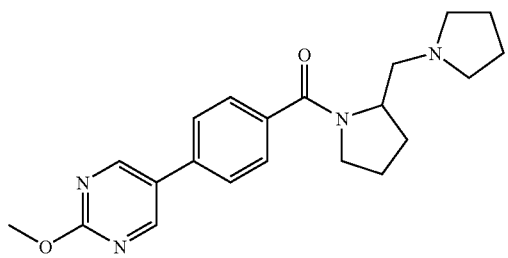 |
| X56 | 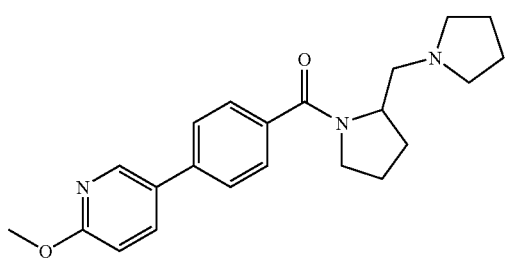 |

| Formula Number | Structure |
| --- | --- |
| X57 | 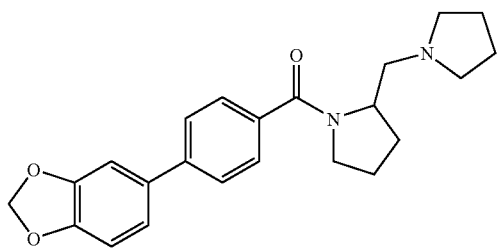 |
| X58 | 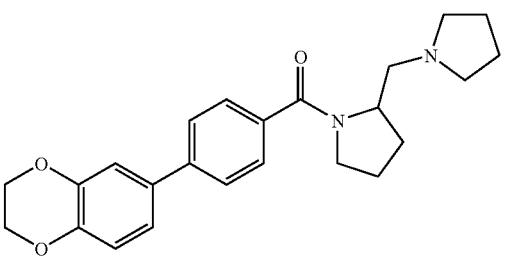 |
| X59 | 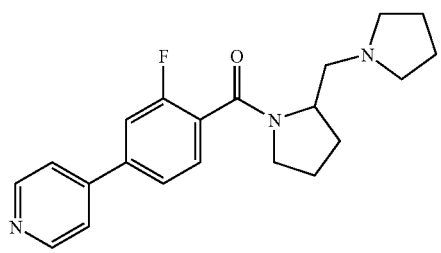 |
| X60 | 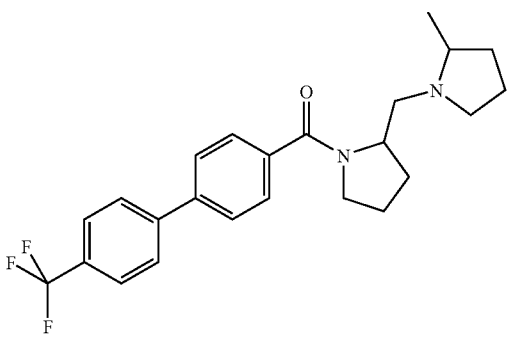 |
| X61 | 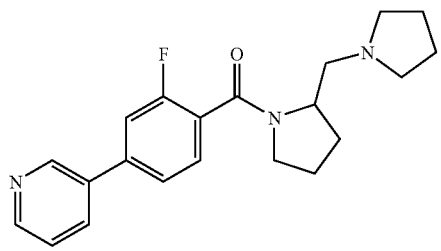 |

-continued
| Formula Number | Structure |
|---|---|
| X62 | 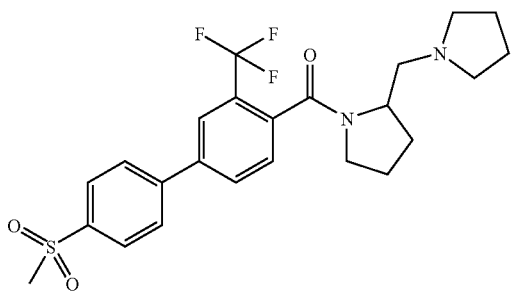 |
| X63 | 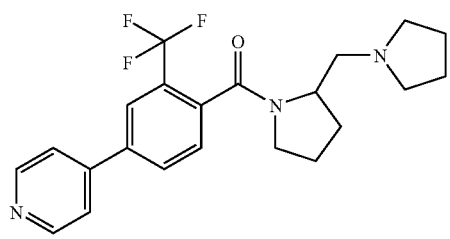 |
| X64 | 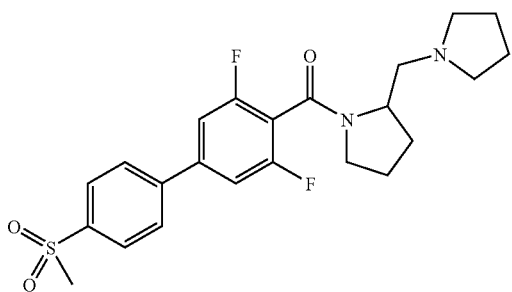 |
| X65 | 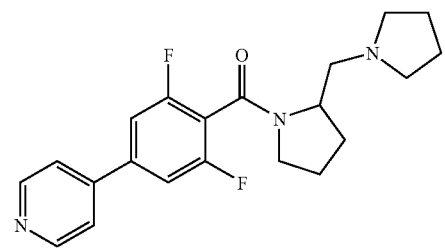 |
| X66 | 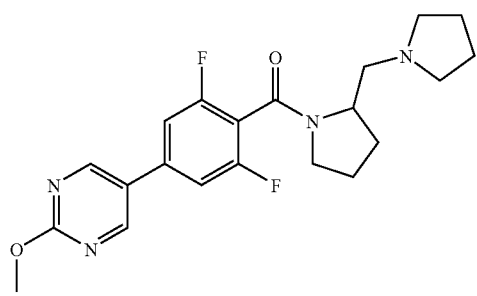 |

-continued
| Formula Number | Structure |
|---|---|
| X67 | 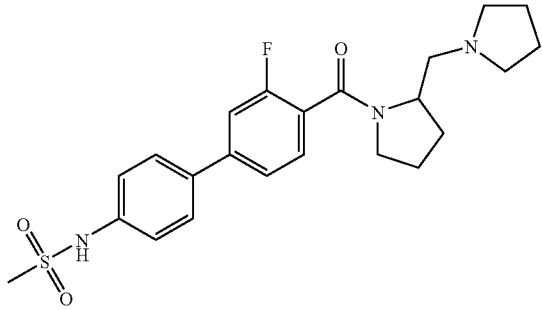 |
| X68 | 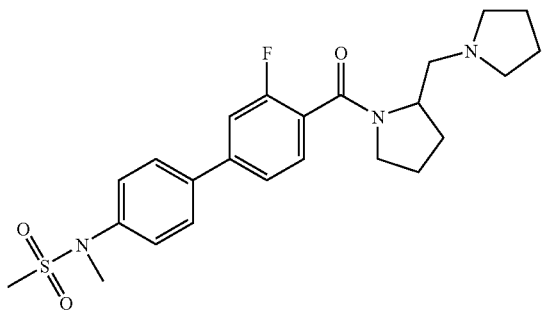 |
| X69 | 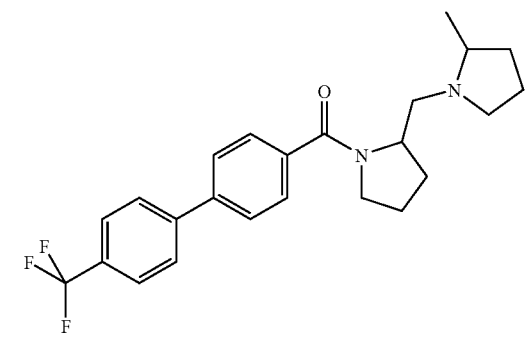 |
| X70 | 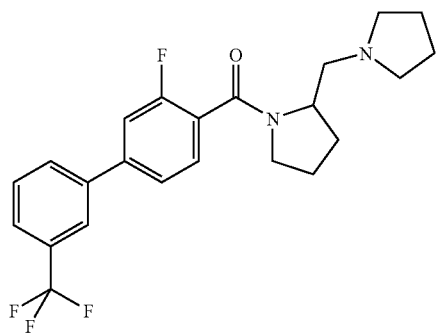 |

-continued
| Formula Number | Structure |
|---|---|
| X71 | 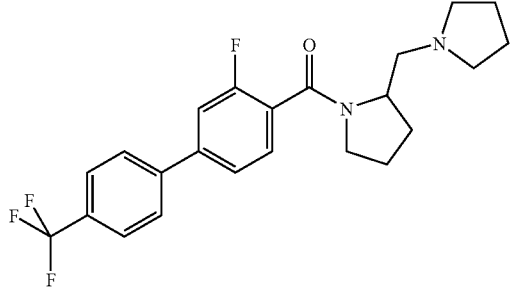 |
| X72 | 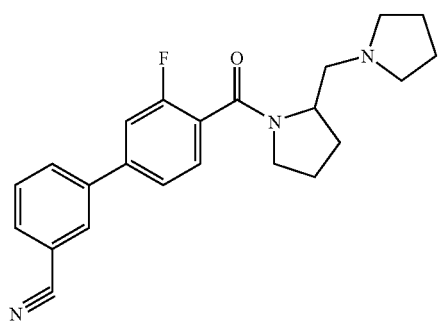 |
| X73 | 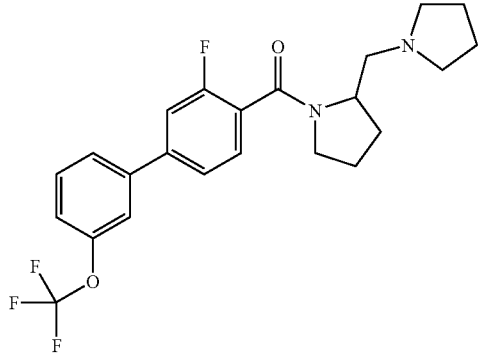 |
| X74 | 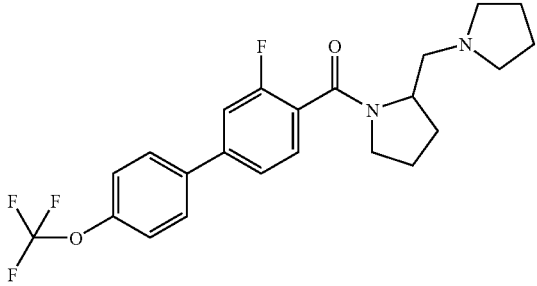 |
| X75 | 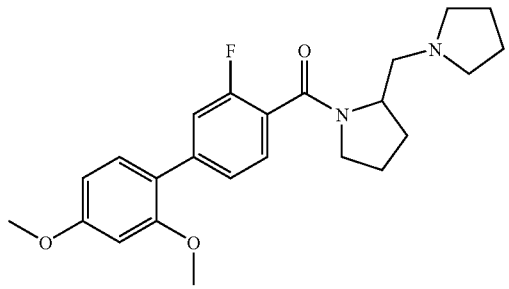 |

-continued
| Formula Number | Structure |
|---|---|
| X76 | 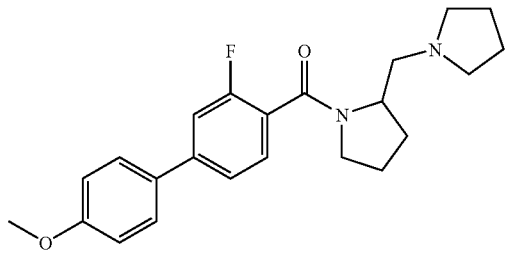 |
| X77 | 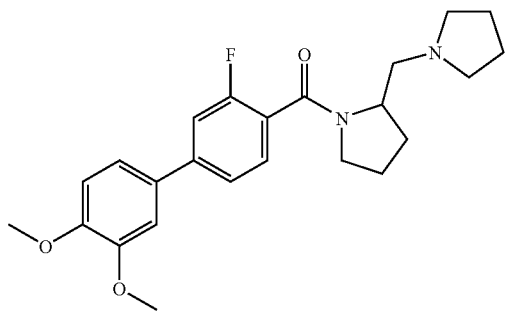 |
| X78 | 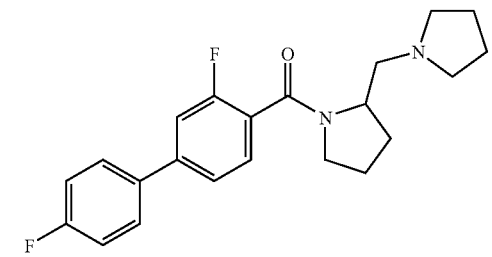 |
| X79 | 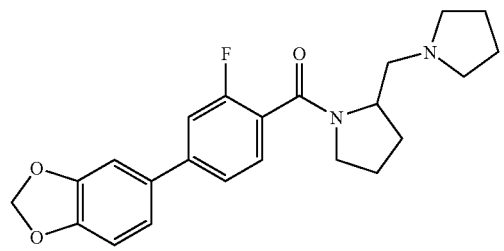 |
| X80 | 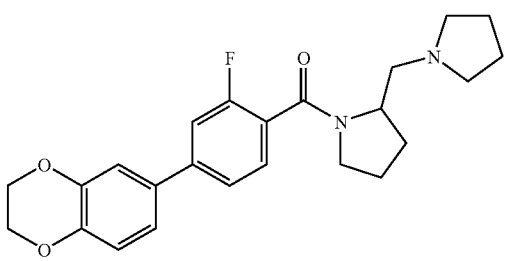 |

-continued
| Formula Number | Structure |
|---|---|
| X81 | 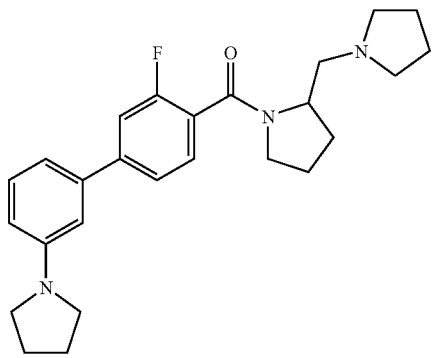 |
| X82 | 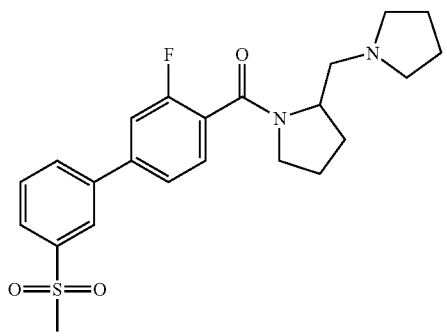 |
| X83 | 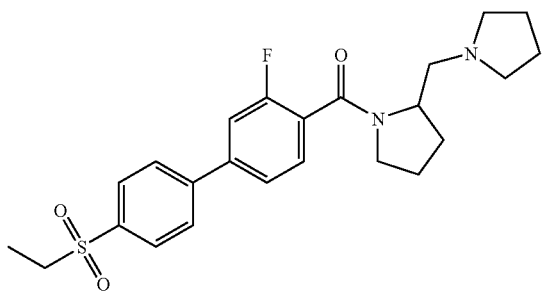 |
| X84 | 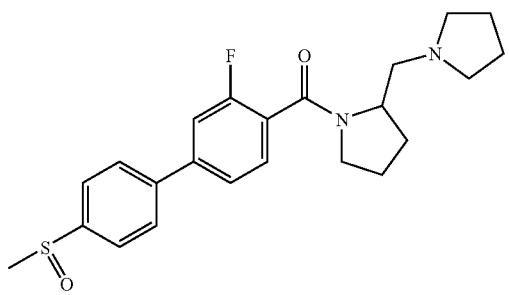 |
| X85 | 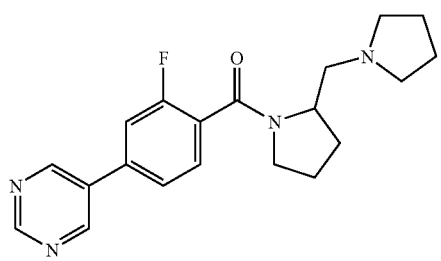 |

-continued
| Formula Number | Structure |
|---|---|
| X86 | 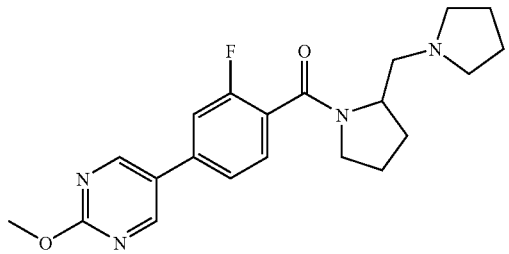 |
| X87 | 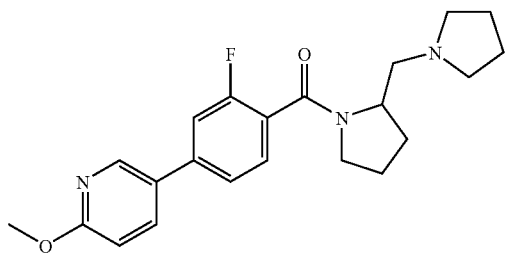 |
| X88 | 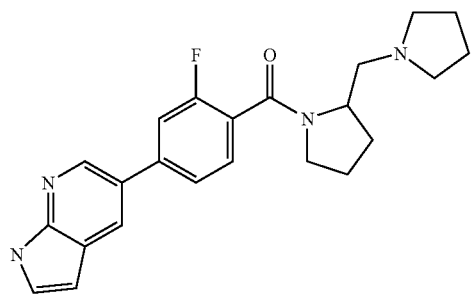 |
| X89 | 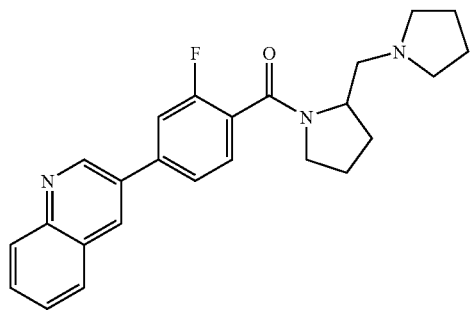 |
| X90 | 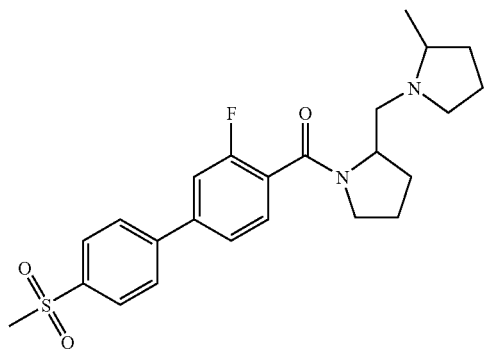 |

-continued
| Formula Number | Structure |
|---|---|
| X91 | 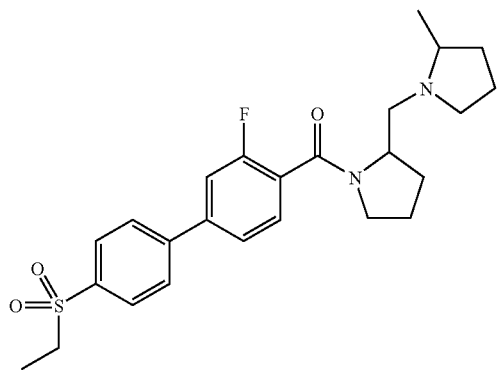 |
| X92 | 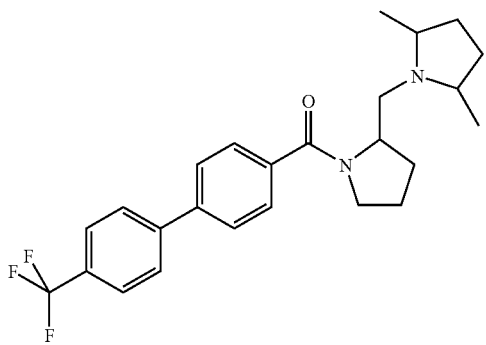 |
| X93 | 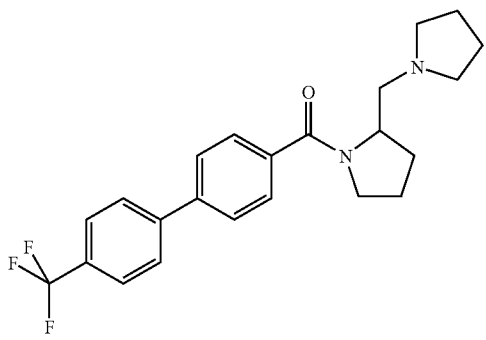 |
| X94 | 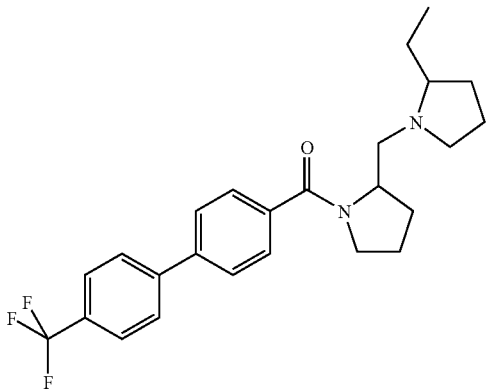 |

-continued
| Formula Number | Structure |
|---|---|
| X95 | 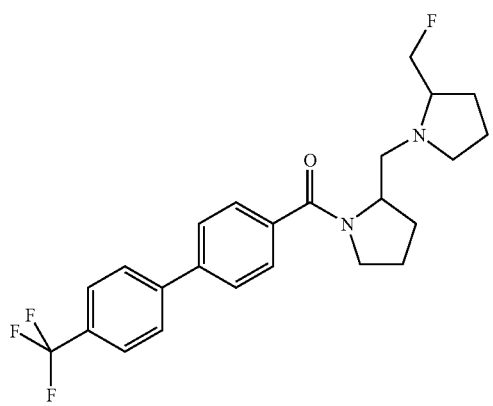 |
| X96 | 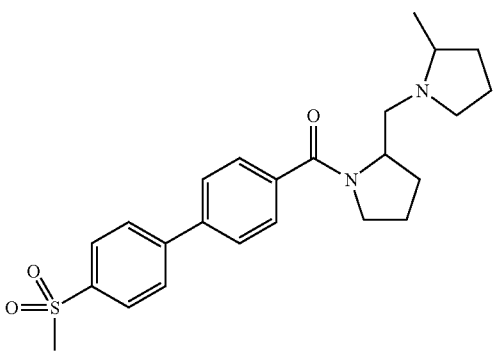 |
| X97 | 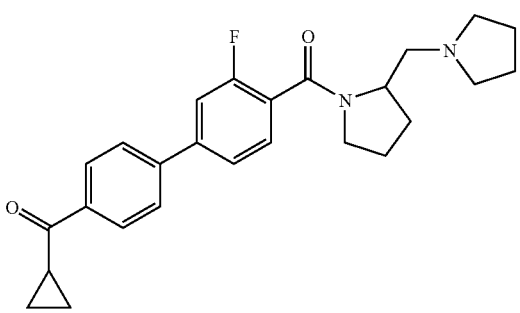 |
| X98 | 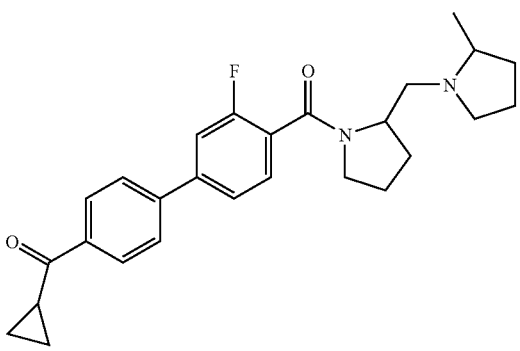 |

-continued
| Formula Number | Structure |
|---|---|
| X99 | 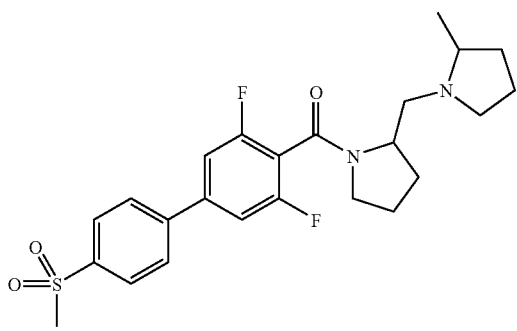 |
| X100 | 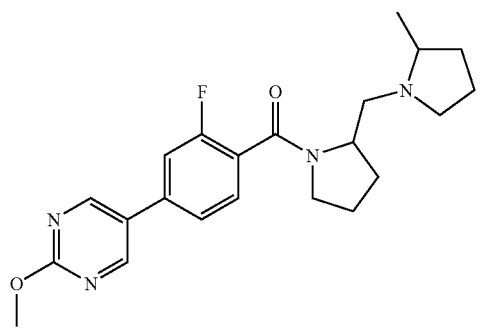 |
| X101 | 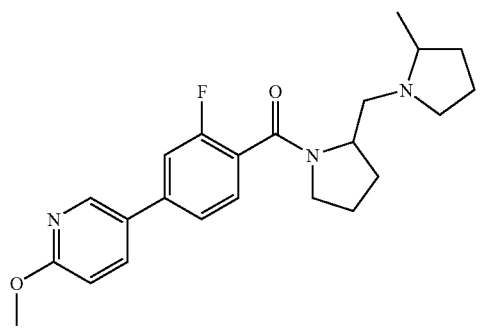 |
| X102 | 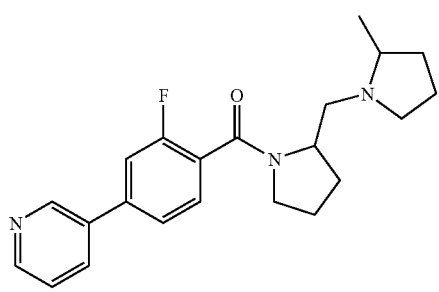 |

-continued
| Formula Number | Structure |
|---|---|
| X103 | 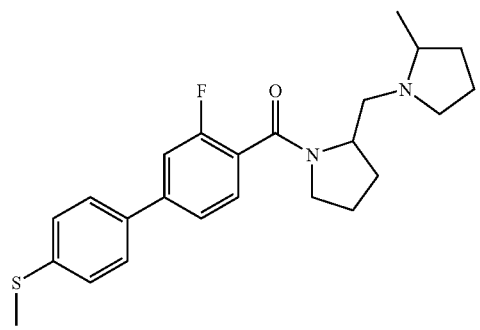 |
| X104 | 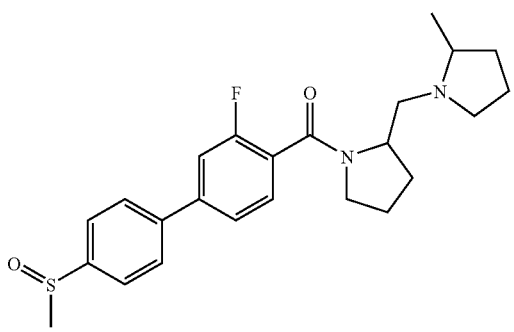 |
| X105 | 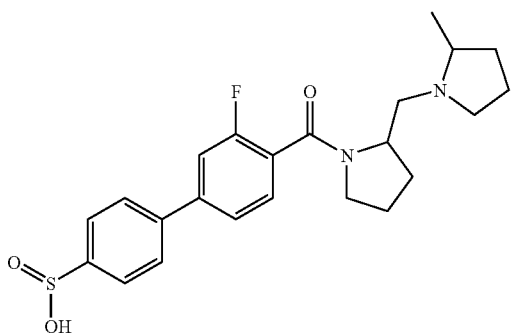 |
| X106 | 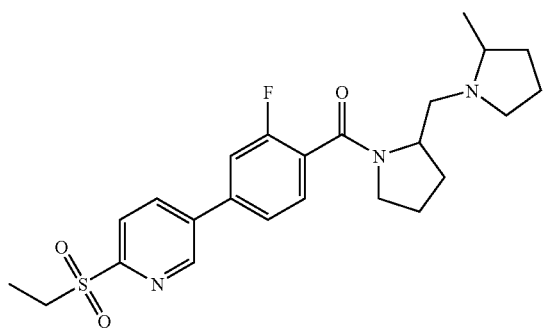 |
| X107 | 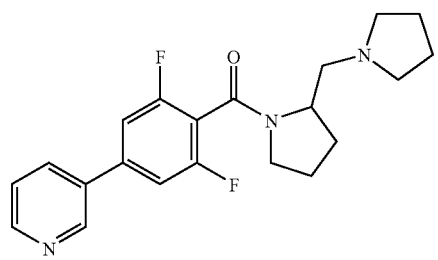 |

-continued
| Formula Number | Structure |
|---|---|
| X108 | 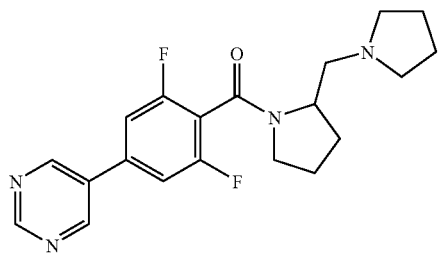 |
| X109 | 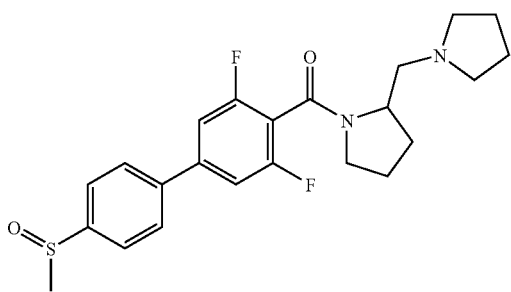 |
| X110 | 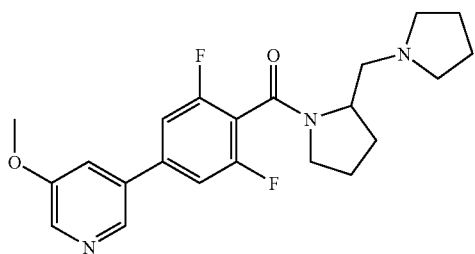 |
| X111 | 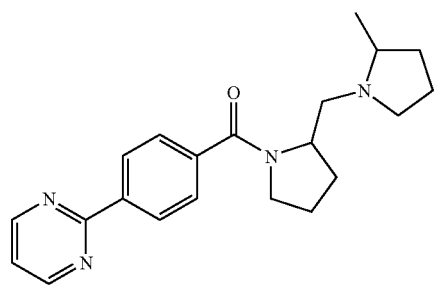 |
| X112 | 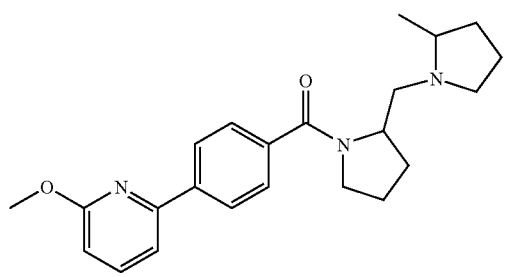 |

| Formula Number | Structure |
|---|---|
| X113 | 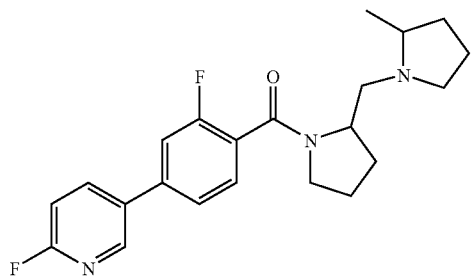 |
| X114 | 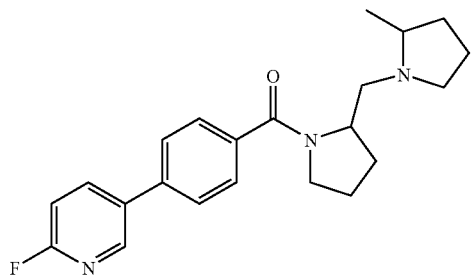 |
| X115 | 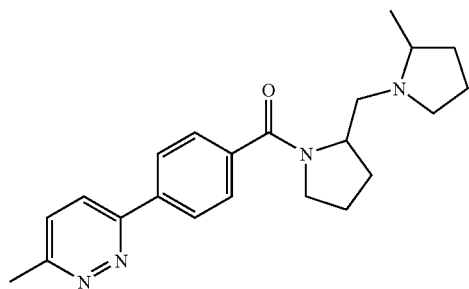 |

The pharmaceutical salts of the invention are typically formed by reacting a compound of Formula I or Formula II with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole. The embodiments of this invention include each of the compounds described in Table 1 in the form of a salt with each of the chemically compatible salt counterions described herein.

The optimal time for performing the reactions of the Schemes, Preparations, and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I or Formula II may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The compound of Formula I or Formula II is preferably formulated in a unit dosage form prior to administration. Therefore, yet another embodiment of the present invention is a pharmaceutical composition comprising a compound of Formula I or Formula II and one or more pharmaceutically acceptable carriers, diluents or excipients.

The present pharmaceutical compositions are prepared by known procedures using well-known and readily available ingredients. In making the formulations of the present invention, the active ingredient (Formula I or Formula II compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as a re conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

Utility

Compounds of Formula I or Formula II are effective as antagonists or inverse agonists of the histamine H3 receptor, and thus inhibit the activity of the H3 receptor. More particularly, these compounds are selective antagonists or inverse agonists of the histamine H3 receptor. As selective antagonists or inverse agonists, the compounds of Formula I or Formula II are useful in the treatment of diseases, disorders, or conditions responsive to the inactivation of the histamine H3 receptor, including but not limited to obesity and other eating-related disorders, and cognitive disorders. It is postulated that selective antagonists or inverse agonists of H3R will raise brain histamine levels and possibly that of other monoamines resulting in inhibition of food consumption while minimizing peripheral consequences. Although a number of H3R antagonists are known in the art, none have proven to be satisfactory obesity or cognitive drugs. There is increasing evidence that histamine plays an important role in energy homeostasis. Histamine, acting as a neurotransmitter in the hypothalamus, suppressed appetite. Histamine is an almost ubiquitous amine found in many cell types and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor GPRv53 has been recently identified. GPRv53 is found in high levels in peripheral white blood cells; only low levels have been identified in the brain by some investigators while others cannot detect it in the brain. However, any drug discovery effort initiated around H3R must consider GPRv53 as well as the other subtypes.

The compounds of the present invention can readily be evaluated by using a competitive inhibition Scintillation Proximity Assay (SPA) based on a H3R binding assay using [3H] α methylhistamine as ligand. Stable cell lines, including but not limited to HEK can be transfected with cDNA coding for H3R to prepare membranes used for the binding assay.

The technique is illustrated below (Preparation of Histamine Receptor Subtype Membranes) for the histamine receptor subtypes.

Membranes isolated as described in (Preparation of Histamine Receptor Subtype Membranes) were used in a [35S] GTP$_\gamma$S functional assay. Binding of [35S]GTP$_\gamma$S to membranes indicates agonist activity. Compounds of the invention of Formula I or Formula II were tested for their ability to inhibit binding in the presence of agonists. Alternately, the same transfected cell lines were used for a cAMP assay wherein H3R agonists inhibited forskolin-activated synthesis of cAMP. Compounds of Formula I or Formula II were tested for their ability to permit forskolin-stimulated cAMP synthesis in the presence of agonist.

Preparation of Histamine Receptor Subtype Membranes

A. Preparation H1R Membranes cDNA for the human histamine 1 receptor (H1R) was cloned into a mammalian expression vector containing the CMV promoter (pcDNA3.1(+), Invitrogen) and transfected into HEK293 cells using the FuGENE Transfection Reagent (Roche Diagnostics Corporation). Transfected cells were selected using G418 (500 µ/ml). Colonies that survived selection were grown and tested for histamine binding to cells grown in 96-well dishes using a scintillation proximity assay (SPA) based radioligand binding assay. Briefly, cells, representing individual selected clones, were grown as confluent monolayers in 96-well dishes (Costar Clear Bottom Plates, #3632) by seeding wells with 25,000 cells and growing for 48 hours (37° C., 5% $CO_2$). Growth media was removed and wells were rinsed two times with PBS (minus $Ca^{2+}$ or $Mg^{2+}$). For total binding, cells were assayed in a SPA reaction containing 50 mM Tris-HCL (assay buffer), pH 7.6, 1 mg wheat germ agglutinin SPA beads (Amersham Pharmacia Biotech, #RPN0001), and 0.8 nM $^3$H-pyrilamine (Net-594, NEN) (total volume per well=200 µl). Astemizole (10 µM, Sigma #A6424) was added to appropriate wells to determine non-specific binding. Plates were covered with FasCal and incubated at room temperature for 120 minutes. Following incubation, plates were centrifuged at 1,000 rpm (~800 g) for 10 minutes at room temperature. Plates were counted in a Wallac Trilux 1450 Microbeta scintillation counter. Several clones were selected as positive for binding, and a single clone (H1R40) was used to prepare membranes for binding studies. Cell pellets, representing ~10 grams, were resuspended in 30 ml assay buffer, mixed by vortexing, and centrifuged (40,000 g at 4° C.) for 10 minutes. The pellet resuspension, vortexing, and centrifugation was repeated 2 more times. The final cell pellet was resuspended in 30 ml and homogenized with a Polytron Tissue Homogenizer. Protein determinations were done using the Coomassie Plus Protein Assay Reagent (Pierce). Five micrograms of protein was used per well in the SPA receptor-binding assay.

B. Preparation H2R membranes cDNA for the human histamine 2 receptor was cloned, expressed and transfected into HEK 293 cells as described above. Histamine binding to cells was assayed by SPA described above. For total binding, cells were assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM $^3$H-tiotidine (Net-688, NEN) (total volume per well=200 µl). Cimetidine (10 µM, Sigma #C4522) was added to appropriate wells to determine non-specific binding.

Several clones were selected as positive for binding, and a single clone (H2R10) was used to prepare membranes for binding studies. Five micrograms of protein was used per well in the SPA receptor-binding assay.

C. Preparation of H3R Membranes cDNA for the human histamine 3 receptor was cloned and expressed as described in (A. Preparation H1R membranes), above. Transfected cells were selected using G418 (500 µ/ml), grown, and tested for histamine binding by the SPA described above. For total binding, cells were assayed in a SPA reaction described above containing 50 mM Tris-HCL (assay buffer), pH 7.6, 1 mg wheat germ agglutinin SPA beads (Amersham Pharmacia Biotech, #RPNQ0001), and 1 nM (3H)-n-alpha-methylhistamine (NEN, NET1027) (total volume per well=200 µl). Thioperimide was added to determine non-specific binding. Several clones were selected as positive for binding, and a single clone (H3R8) was used to prepare membranes for binding studies described above. Five micrograms of protein was used per well in the SPA receptor-binding assay.

All compounds set forth in the examples exhibit affinity for the H3 receptor greater than 1 uM. Preferred compounds of the invention exhibit affinity for the H3 receptor greater than 200 nM. Most preferred compounds of the invention exhibit affinity for the H3 receptor greater than 20 nM.

D. Preparation of GPRv53 Membranes cDNA for the human GPRv53 receptor was cloned and expressed as described in (A. Preparation H1R membranes), above. Transfected cells were selected, tested for histamine binding, and selected. HEK293 GPRv53 50 cells were grown to confluency in DMEM/F12 (Gibco) supplemented with 5% FBS and 500 ug/ml G418 and washed with Delbecco's PBS (Gibco) and harvested by scraping. Whole cells were homogenized with a Polytron tissuemizer in binding buffer, 50 mM Tris pH 7.5. Cell lysates, 50 ug, were incubated in 96 well dishes with 3 nM (3H) Histamine and compounds in binding buffer for 2 hours at room temperature. Lysates were filtered through glass fiber filters (Perkin Elmer) with a Tomtec cell harverster. Filters were counted with melt-on scintillator sheets (Perkin Elmer) in a Wallac Trilux 1450 Microbeta Scintillation counter for 5 minutes.

Pharmacological Results cAMP ELISA

HEK293H3R8 cells prepared as described above were seeded at a density of 50,000 cells/well and grown overnight in DMEM/F12 (Gibco) supplemented with 5% FBS and 500 ug/ml G418. The next day tissue culture medium was removed and replaced with 50 µl cell culture medium containing 4 mM 3-isobutyl-1-methylxanthine (Sigma) and incubated for 20 minutes at room temperature. Antagonist were added in 50 µl cell culture medium and incubated for 20 minutes at room temperature. Agonist R(−)α methylhistamine (RBI) at a dose response from $1 \times 10^{-10}$ to $1 \times 10^{-5}$ M was then added to the wells in 50 µl cell culture medium and incubated for 5 minutes at room temperature. Then 50 µl of cell culture medium containing 20 µM Forskolin (Sigma) was added to each well and incubated for 20 minutes at room temperature. Tissue culture medium was removed and cells were lysed in 0.1M HCl and cAMP was measured by ELISA (Assay Designs, Inc.).

[35S] GTPγ [S] Binding Assay

Antagonist activity of selected compounds was tested for inhibition of [35S] GTP γ [S] binding to H3R membranes in the presence of agonists. Assays were run at room temperature in 20 mM HEPES, 100 mM NaCl, 5 mM $MgCl_2$ and 10 uM GDP at pH 7.4 in a final volume of 200 ul in 96-well Costar plates. Membranes isolated from H3R8-expressing HEK293 cell line (20 ug/well) and GDP were added to each well in a volume of 50 µl assay buffer. Antagonist was then added to the wells in a volume of 50 µl assay buffer and incubated for 15 minutes at room temperature. Agonist R(−)

alpha methylhistamine (RBI) at either a dose response from $1 \times 10^{-10}$ to 1A1-5 M or fixed concentration of 100 nM were then added to the wells in a volume of 50 µl assay buffer and incubated for 5 minutes at room temperature. GTP γ [35S] was added to each well in a volume of 50 µl assay buffer at a final concentration of 200 pM, followed by the addition of 50 µl of 20 mg/ml WGA coated SPA beads (Amersham). Plates were counted in Wallac Trilux 1450 Microbeta scintillation counter for 1 minute. Compounds that inhibited more than 50% of the specific binding of radioactive ligand to the receptor were serially diluted to determine a K[i](nM). The results are given below for the indicated compound.

TABLE 2

| Example | | Ki (nM) |
|---|---|---|
| 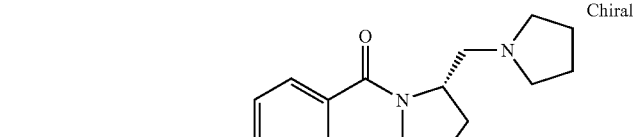 | Chiral | 32 |
|  | | 49 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound structurally represented by Formula I (I)

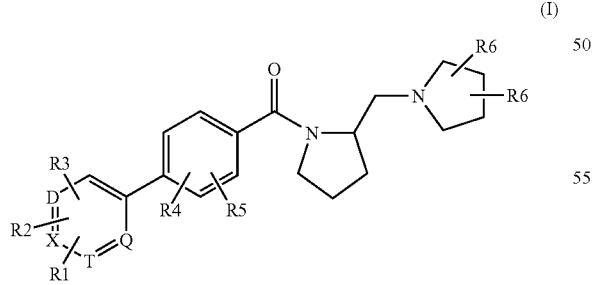

or a pharmaceutically acceptable salt thereof wherein:
Q, T, X, and D independently represent carbon or nitrogen, provided that no more than two of Q, T, X, and D are nitrogen;
R1, R2, and R3 are independently at each occurrence
—H,
-halogen,
—($C_1$-$C_7$) alkyl,
—CN,
—C(O)R7,
—C(O)($C_3$-$C_5$)cycloalkyl,
—C(O)NR7R8,
—OCF$_3$,
—OR7,
—NO$_2$,
—NR7R8,
—NR9SO$_2$ R7,
—NR9C(O)R7,
—NR9CO$_2$R7,
—NR9C(O)NR7R8,
—SR7,
—SO$_2$R7,
—SO$_2$CF$_3$,
—SO$_2$ NR7R8,
—S(O)R7,
—O(CH$_2$)mNR7R8,
-heteroaryl-R9,
-phenyl-R9,
provided however that wherein D is nitrogen, then R1 or R2 or R3 are not attached to D, and provided that wherein X is nitrogen, then R1 or R2 or R3 are not attached to X, and provided that wherein T is nitrogen, then R1 or R2 or R3 are not attached to T, and provided that wherein Q is nitrogen, then R1 or R2 or R3 are not attached to Q;
and further provided that when D and X are carbon, then R1 and R2 can combine to form a 5 or 6 membered ring with D and X,

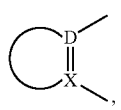

wherein the ring so formed may optionally include one double bond in the case of a five membered ring or two double bonds in the case of a six membered ring, and wherein one to three ring atoms may optionally be heteroatoms independently selected from N, O, or S;
wherein m is 1, 2, 3 or 4;
R4 and R5 are independently at each occurrence
—H,
—OH,
-halogen,
—CF$_2$H,
—CF$_3$,
—(C$_1$-C3)alkyl,
—O—(C$_1$-C$_3$) alkyl,
R6 is independently at each occurrence
—H,
-halogen,
—CF3,
—(C$_1$-C$_3$) alkyl,
—NH$_2$,
—NR7R8,
—OH,
—OR7;
R7 and R8 are independently at each occurrence
—H,
—(C$_1$-C$_6$) alkyl,
Wherein R7 and R8 can combine with the atom to which they are attached to form a 3 to 7 membered ring;
R9 is independently at each occurrence
—H,
—(C$_1$-C$_3$) alkyl,
provided the compound is not (3-Fluoro-4'-methanesulfonyl-biphenyl-4yl)-[-methyl-pyrrolidin-1-ylmethyl)-pyrrolidin-1-yl]-methanone, or [4-(6-amino-5-hydroxy-pyridin-3-yl)-phenyl]-(2-pyrrolidin-1-ylmethyl-pyrrolidin-1-yl)-methanone.

2. A compound structurally represented by Formula II

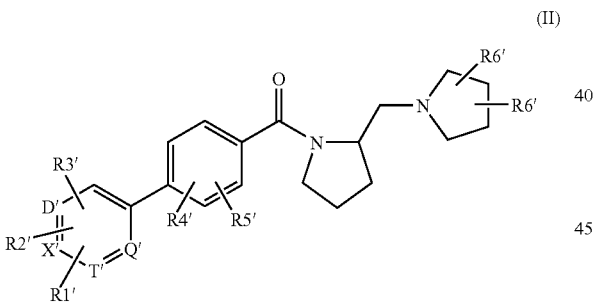

or a pharmaceutically acceptable salt thereof wherein:
Q', T', X', and D' independently represent carbon or nitrogen, provided that no more than two of Q', T', X', and D' are nitrogen;
R1' is
-halogen,
—(C$_1$—C$_7$) alkyl,
—CN,
—C(O)R7',
—C(O)(C$_3$-C$_5$)cycloalkyl,
—C(O)NR7'R8',
—OCF$_3$,
—OR7',
—NO$_2$,
—NR7'R8',
—NR9'SO$_2$R7',
—NR9'C(O)R7',
—NR9'CO$_2$R7',
—NR9'C(O)NR7'R8',
—SR7',
—SO$_2$R7',
—SO$_2$CF$_3$,
—SO$_2$NR7'R8',
—S(O)R7',
—O(CH$_2$)mNR7'R8',
-heteroaryl-R9',
R2' and R3' are independently at each occurrence
—H,
-halogen,
—(C$_1$-C$_7$) alkyl,
—CN,
—C(O)R7',
—C(O)(C$_3$-C$_5$)cycloalkyl,
—C(O)NR7'R8',
—OCF$_3$,
—OR7',
—NO$_2$,
—NR7'R8',
—NR9'SO$_2$R7',
—NR9'C(O)R7',
—NR9'CO$_2$R7',
—NR9'C(O)NR7'R8',
—SR7',
—SO$_2$R7',
—SO$_2$CF$_3$,
—SO$_2$NR7'R8',
—S(O)R7',
—O(CH$_2$)mNR7'R8',
-heteroaryl-R9',
provided however that wherein D' is nitrogen, then R1' or R2' or R3' are not attached to D', and provided that wherein X' is nitrogen, then R1' or R2' or R3' are not attached to X', and provided that wherein T' is nitrogen, then R1' or R2' or R3' are not attached to T', and provided that wherein Q' is nitrogen, then R1' or R2' or R3' are not attached to Q';
wherein m is 1, 2, 3 or 4;
R4' and R5' are independently at each occurrence
—H,
—OH,
-halogen,
—CF$_2$H
—CF$_3$
—(C$_1$-C$_3$)alkyl,
—OR9',
provided that when R4' is —H, then R5' is not —H,
R6' is independently at each occurrence
—H,
-halogen,
—CF$_3$,
—CH$_3$,
—(C$_1$-C$_3$) alkyl,
—NH$_2$,
—NR7'R8',
—OH,
—OR7';
R7' and R8' are independently at each occurrence;
—H,
—(C$_1$-C$_6$) alkyl optionally substituted with up to three halogens,
Wherein R7' and R8' can combine with the atom to which they are attached to form a 3 to 7 membered ring;

R9' is independently at each occurrence
- —H,
- —(C$_1$-C$_3$) alkyl, provided the compound is not (3-Fluoro-4'-methanesulfonyl-biphenyl-4yl)-[methyl-pyrrolidin1-ylmethyl)-pyrrolidin-1-yl]-methanone, or [4-(6-amino-5-hydroxy-pyridin-3-yl)   -phenyl]-(2-pyrrolidin-1-ylmethyl-pyrrolidin1yl)-methanone.

3. The compound or salt of claim 1, wherein D, X, Q and T are carbon.

4. The compound or salt of claim 1, wherein one of D, X, Q or T is nitrogen.

5. The compound or salt of claim 1 wherein two of D, X, Q or T are nitrogen.

6. The compound or salt of claim 1 wherein X is carbon and R1 is attached to X.

7. The compound or salt of claim 6 wherein R4 is halogen.

8. The compound or salt of claim 7 wherein one independent occurrence of R6 is —CH$_3$ and the second independent occurrence of R6 is H.

9. The compound or salt of claim 2 wherein X' is carbon and R1' is attached to X'.

10. The compound or salt of claim 9 wherein X' is carbon and R1' is attached to X', and R4' is halogen.

11. The compound or salt of claim 10 wherein one independent occurrence of R6' is —CH$_3$ and the second independent occurrence of R6' is H.

12. The compound of claim 1 selected from the group consisting of formulae X1 to X89, and 91 to X115:

| Structure |
| --- |

X1

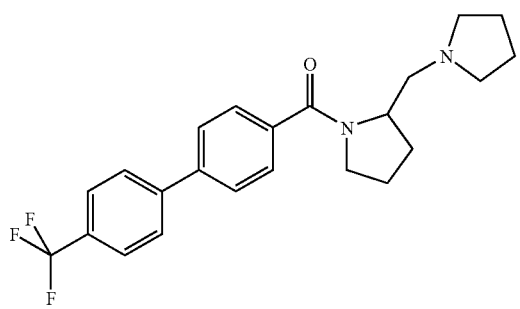

X2

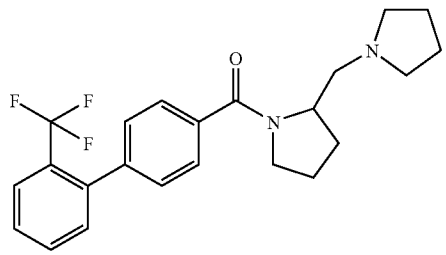

X3

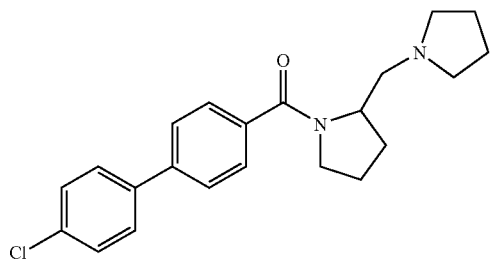

X4

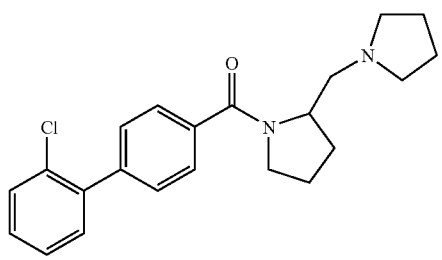

-continued
| Structure |
|---|
| X5 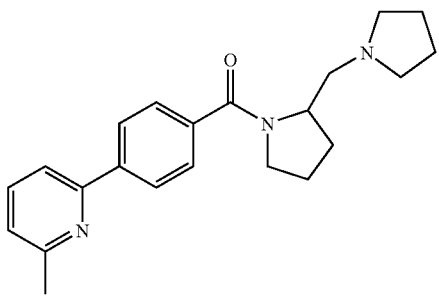 |
| X6 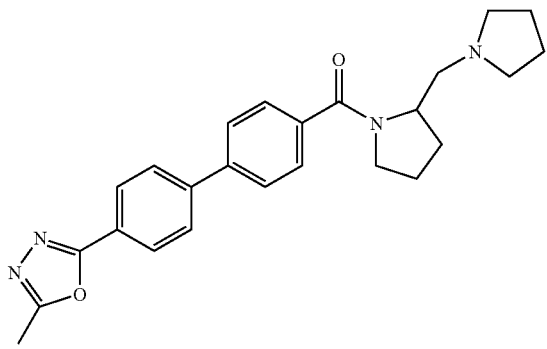 |
| X7 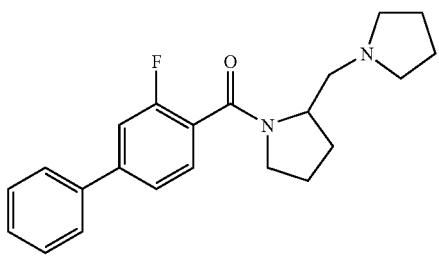 |
| X8 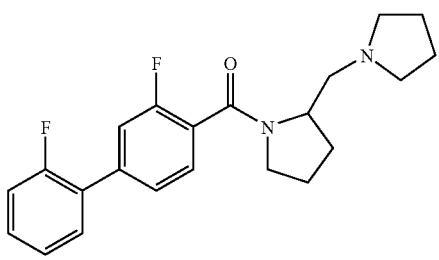 |
| X9 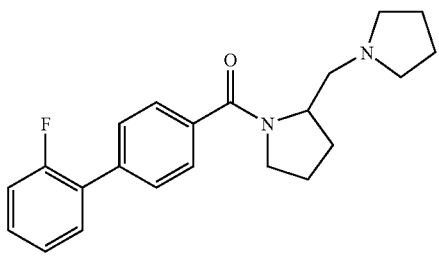 |

-continued
| Structure |
|---|
| X10 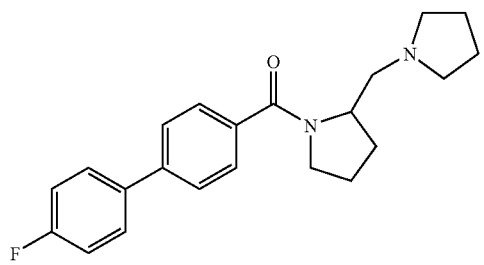 |
| X11 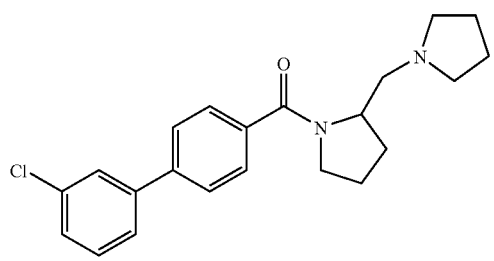 |
| X12 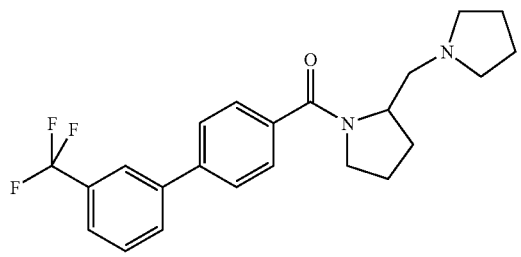 |
| X13 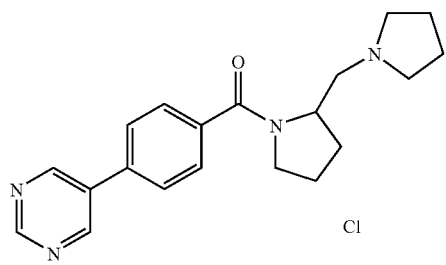 Cl |
| X14 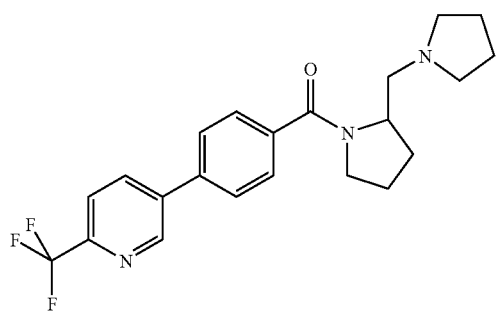 |

| Structure |
|---|
| X15 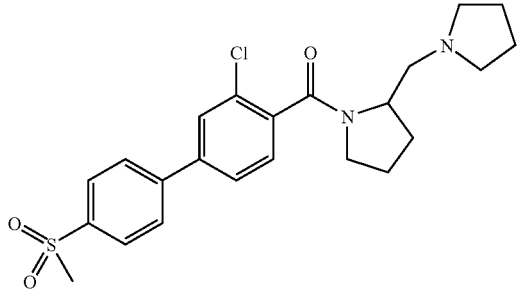 |
| X16 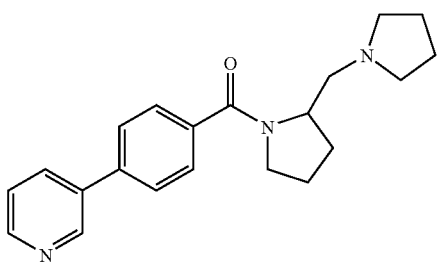 |
| X17 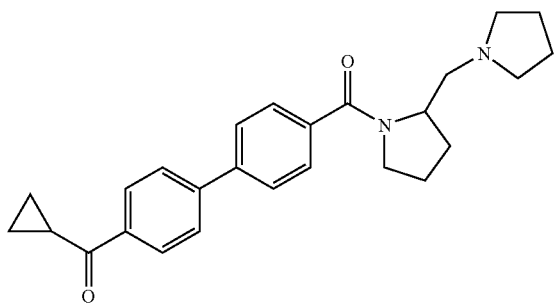 |
| X18 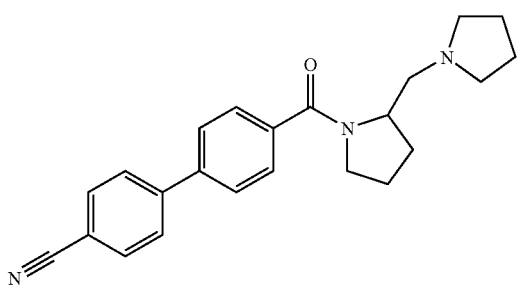 |
| X19 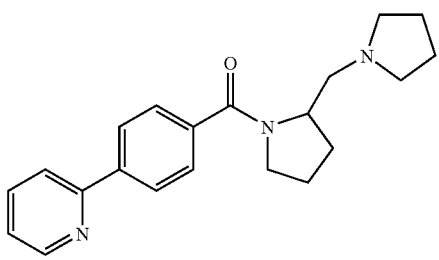 |

| Structure |
|---|
| X20 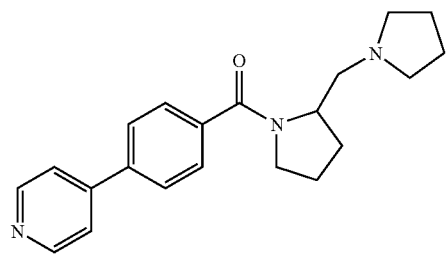 |
| X21 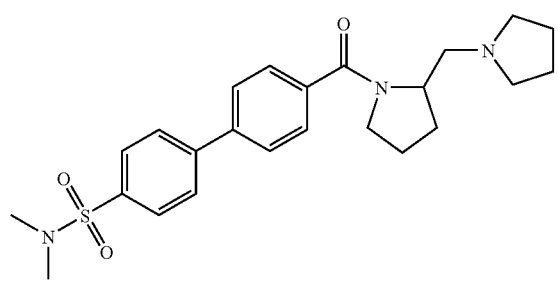 |
| X22 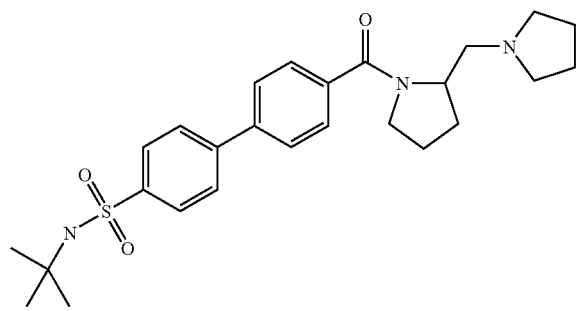 |
| X23 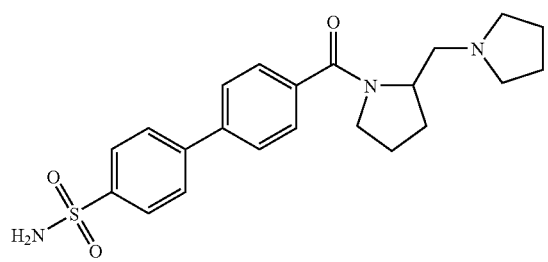 |
| X24 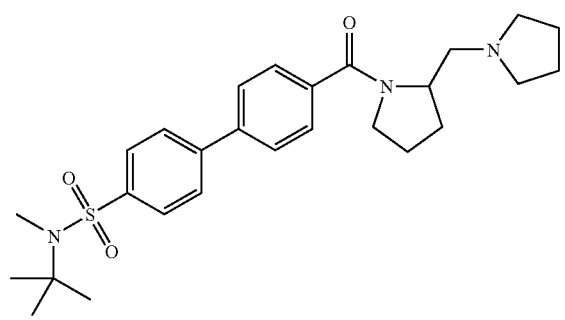 |

-continued
| Structure |
|---|
| X25 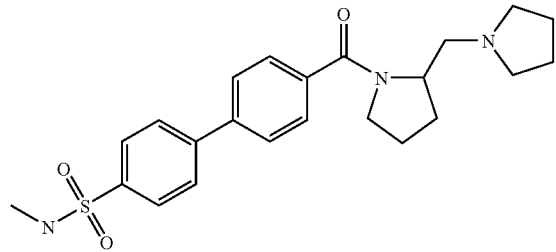 |
| X26 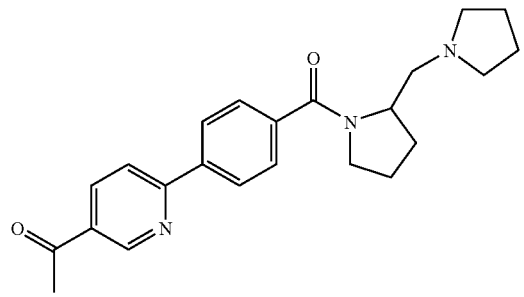 |
| X27 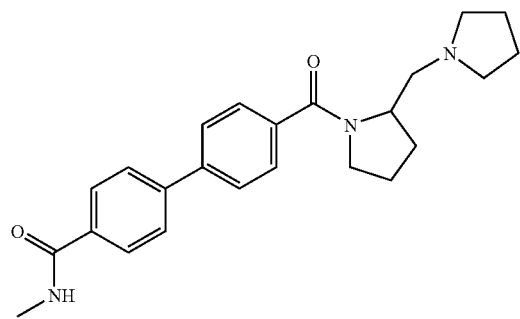 |
| X28 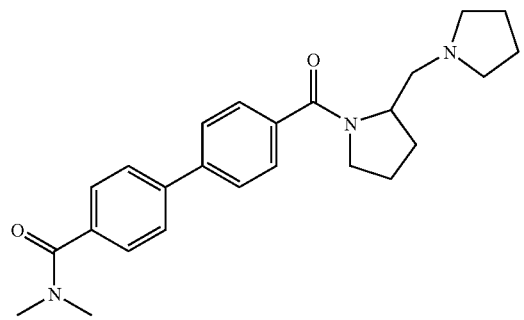 |
| X29 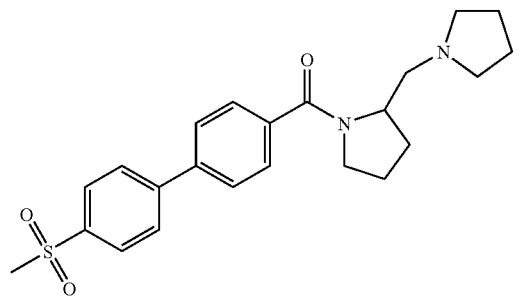 |

-continued
| Structure |
|---|
| X30 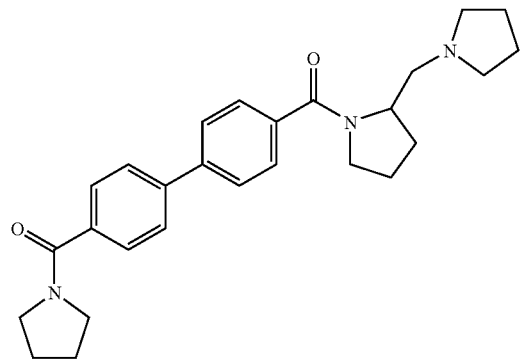 |
| X31 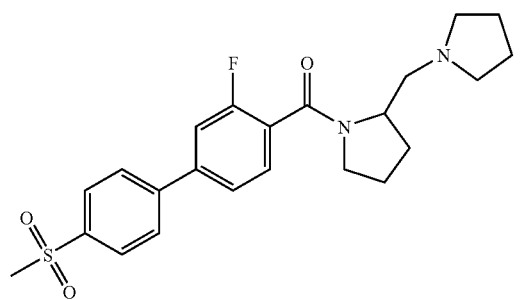 |
| X32 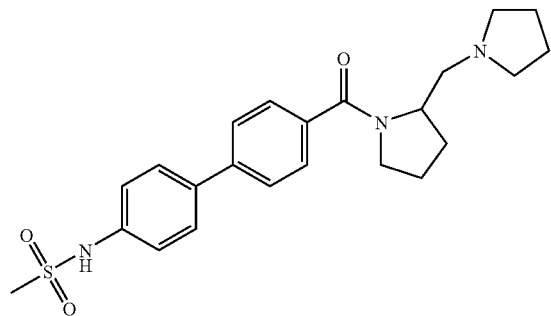 |
| X33 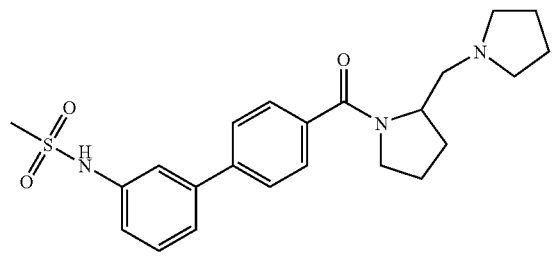 |
| X34 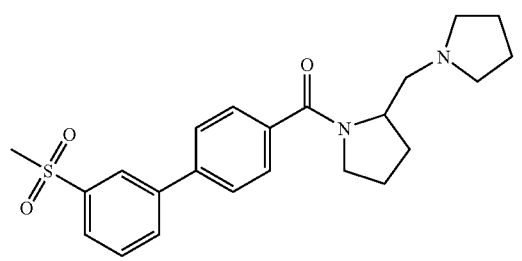 |

-continued
| Structure |
|---|
| X35 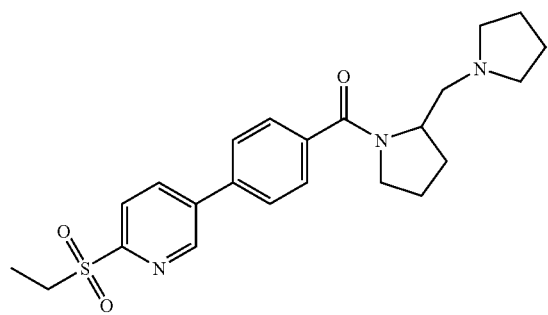 |
| X36 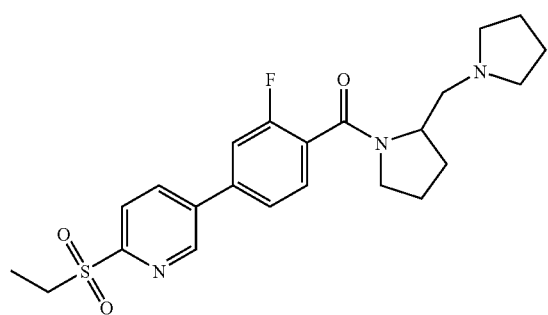 |
| X37 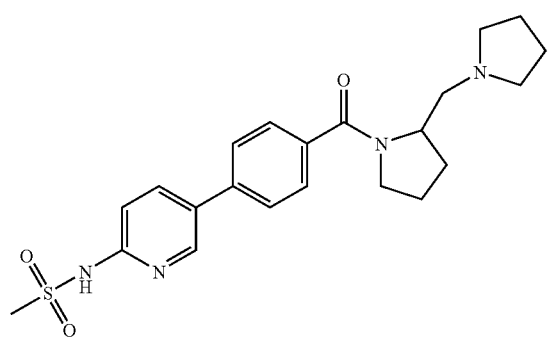 |
| X38 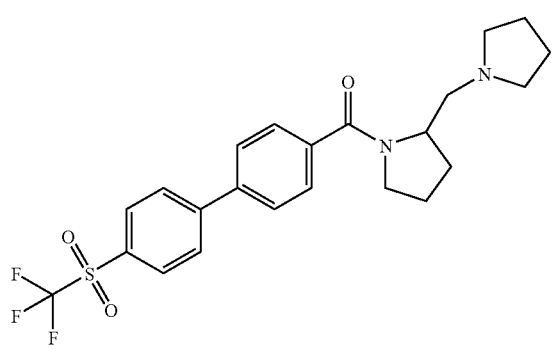 |

| Structure |
|---|
| X39 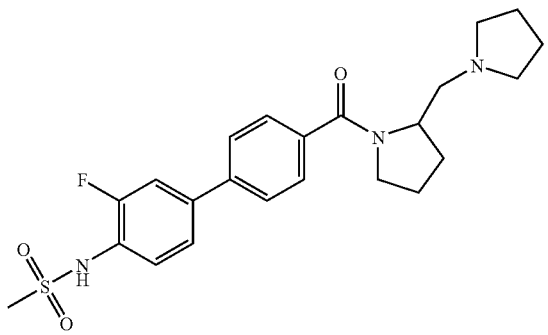 |
| X40 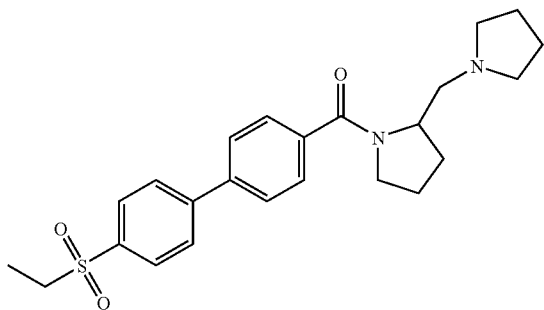 |
| X41 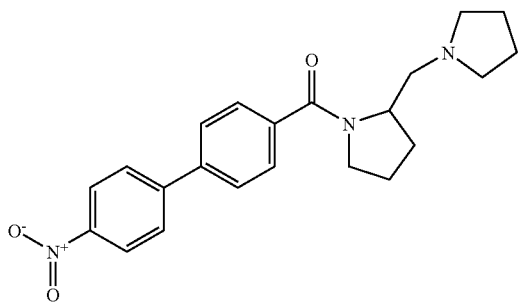 |
| X42 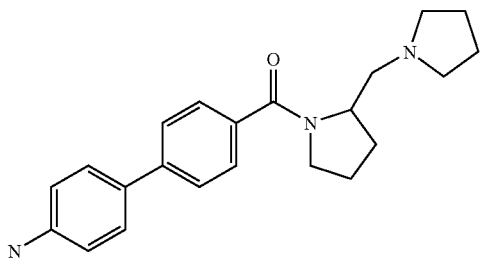 |
| X43 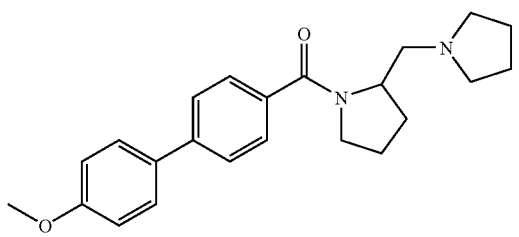 |

-continued
| Structure |
|---|
| X44 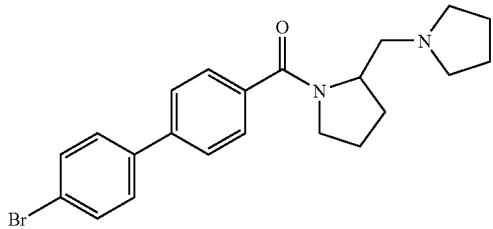 |
| X45 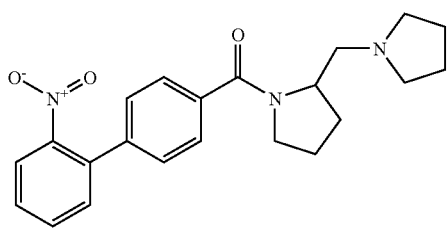 |
| X46 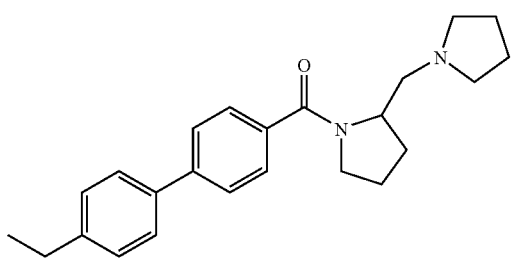 |
| X47 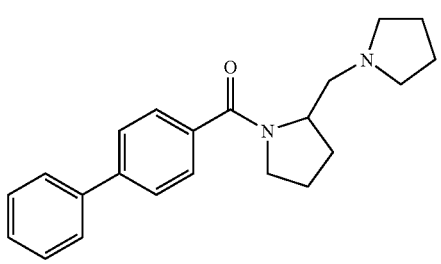 |
| X48 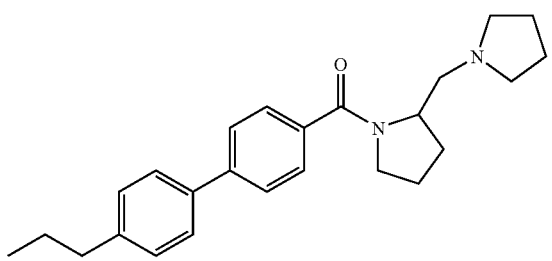 |
| X49 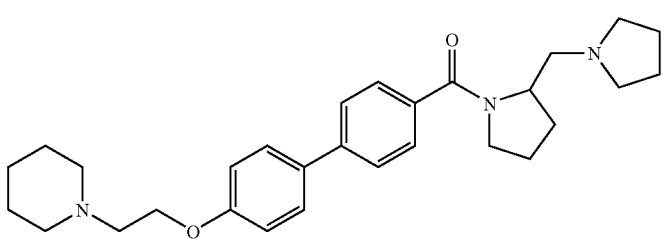 |

-continued
| Structure |
|---|
| X50 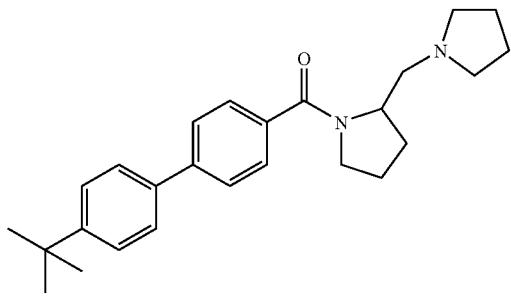 |
| X51 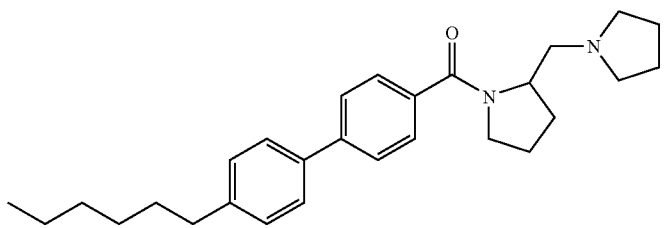 |
| X52 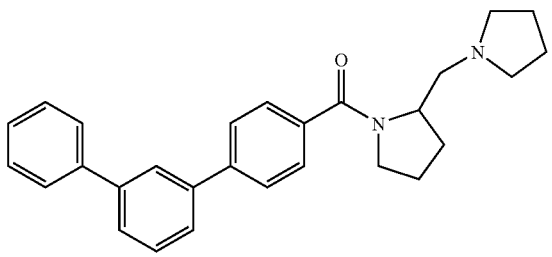 |
| X53 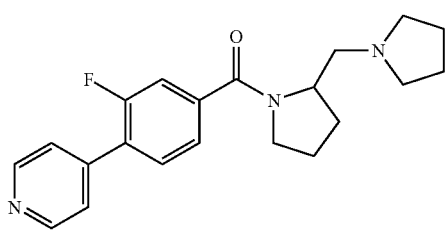 |
| X54 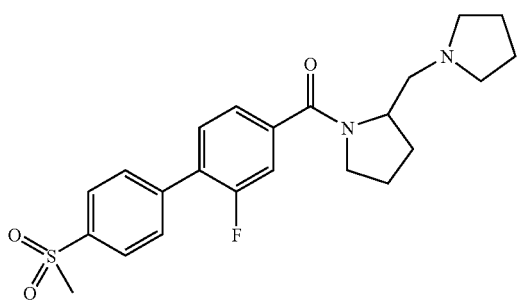 |
| X55 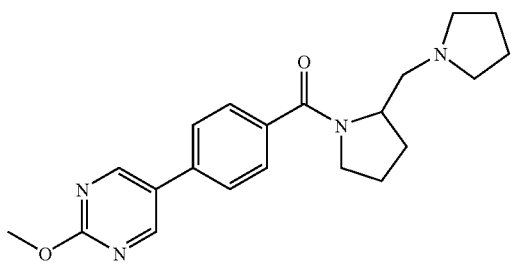 |

| Structure |
|---|
| X56 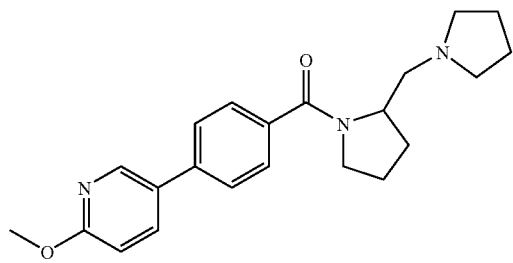 |
| X57 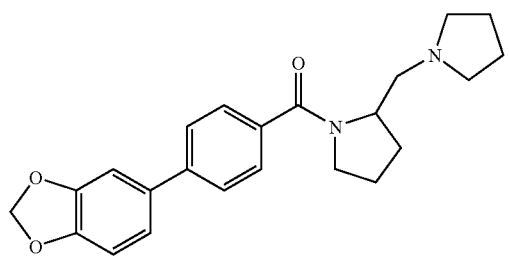 |
| X58 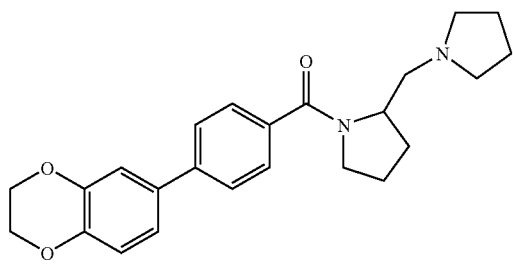 |
| X59 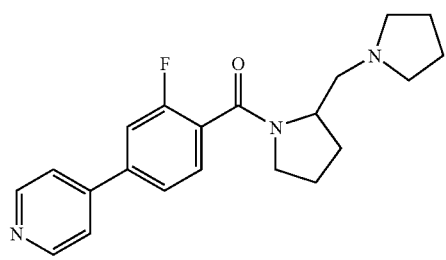 |
| X60 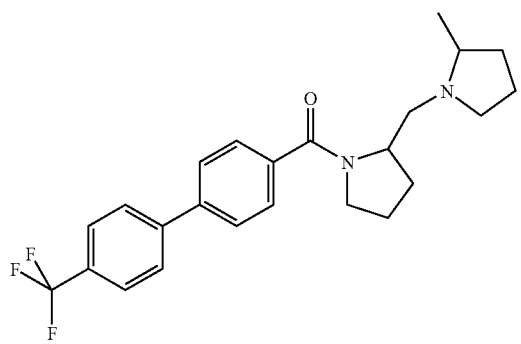 |

| Structure |
|---|
| X61 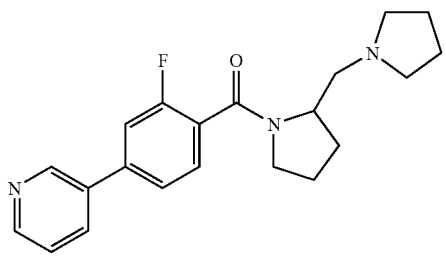 |
| X62 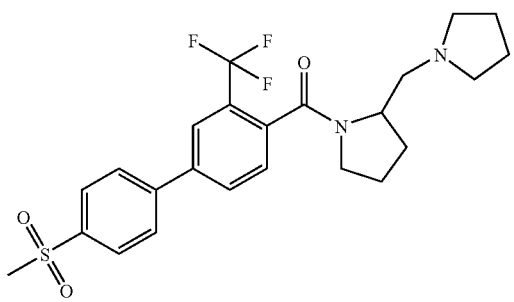 |
| X63 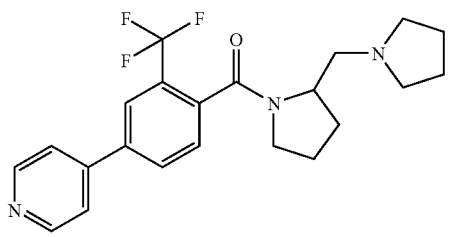 |
| X64 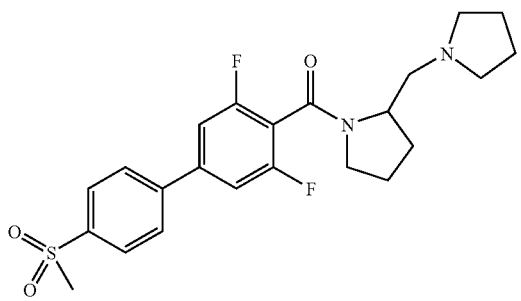 |
| X65 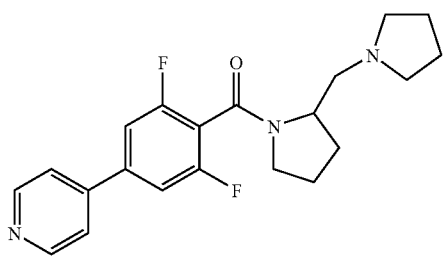 |

-continued
| Structure |
|---|
| X66 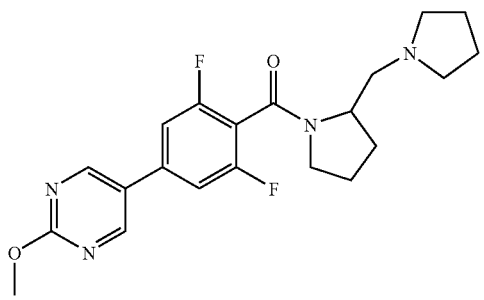 |
| X67 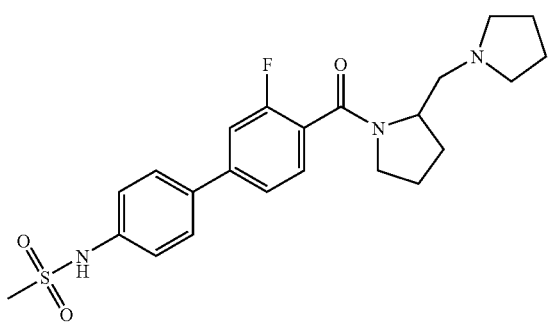 |
| X68 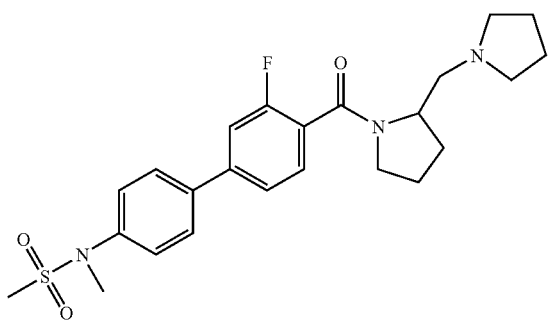 |
| X69 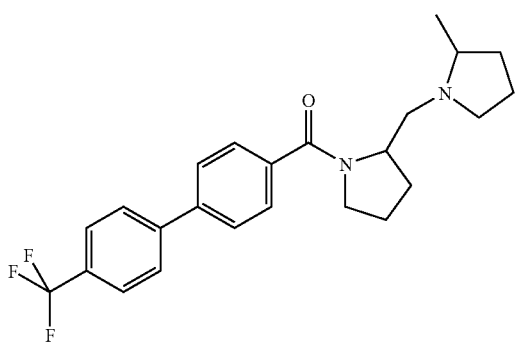 |

-continued
| | Structure |
|---|---|
| X70 | 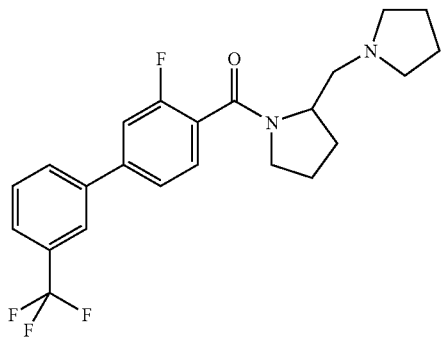 |
| X71 | 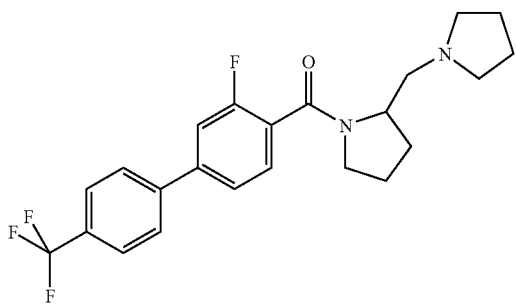 |
| X72 | 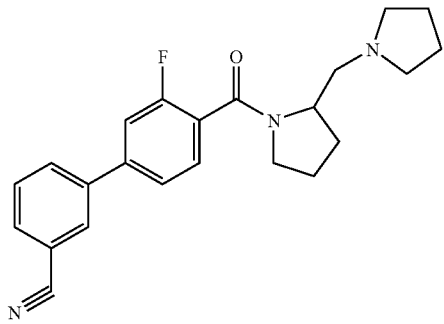 |
| X73 | 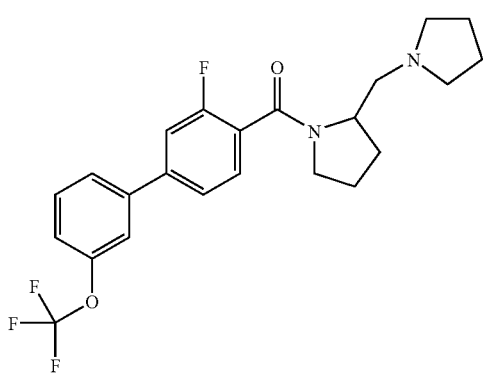 |

| Structure |
|---|
| X74 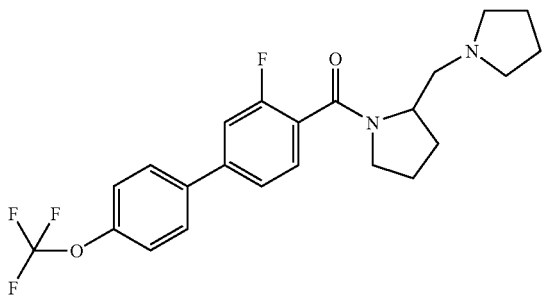 |
| X75 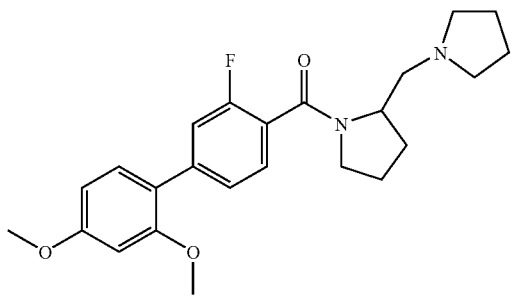 |
| X76 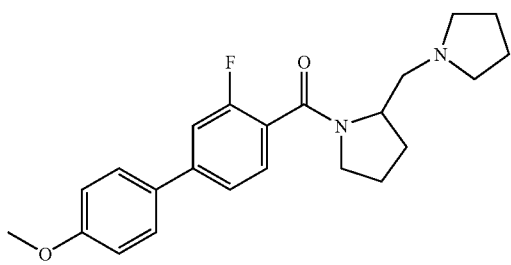 |
| X77 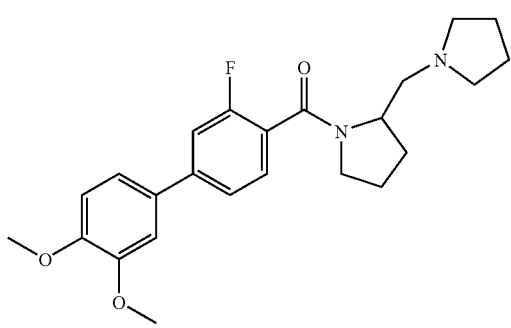 |
| X78 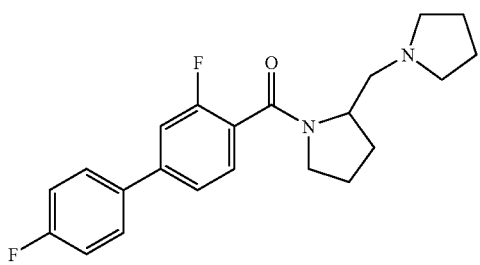 |

-continued
| Structure |
|---|
| X79 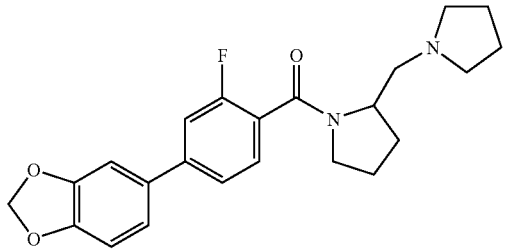 |
| X80 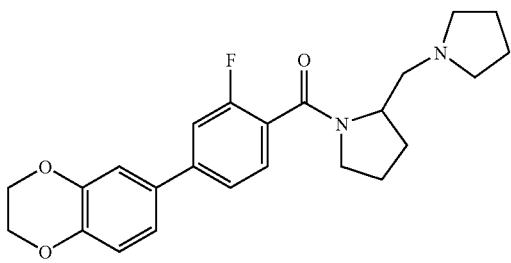 |
| X81 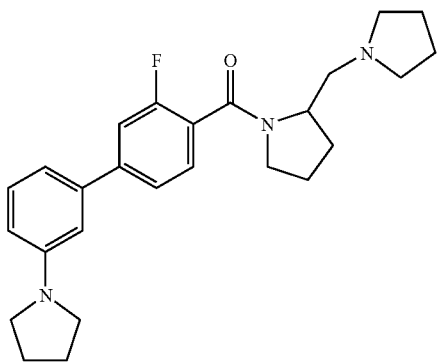 |
| X82 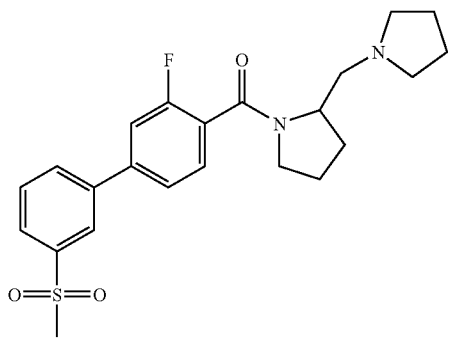 |
| X83 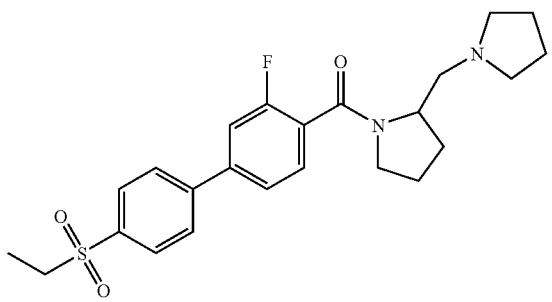 |

| Structure |
|---|
| X84 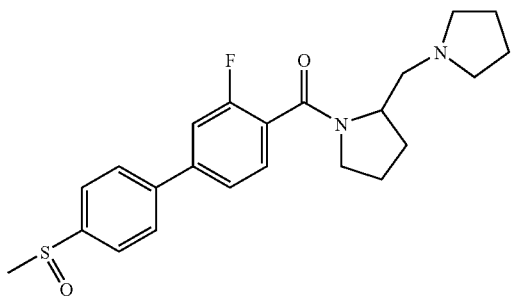 |
| X85 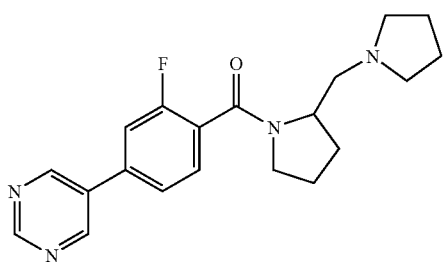 |
| X86 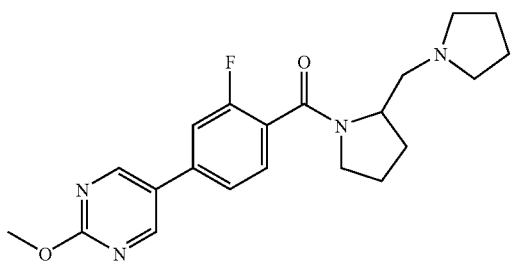 |
| X87 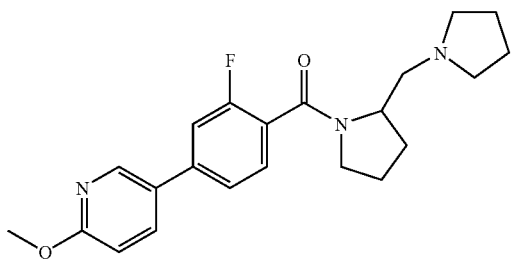 |
| X88 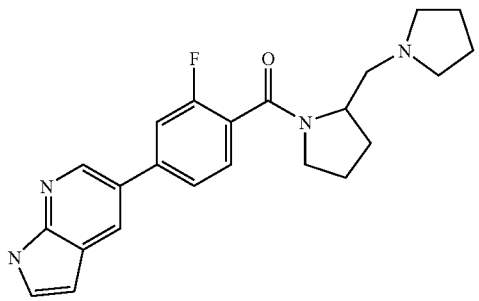 |

-continued
| Structure |
|---|
| X89 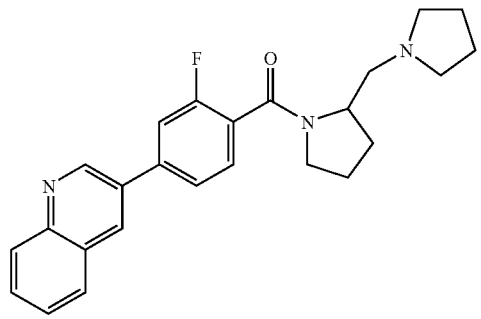 |
| X91 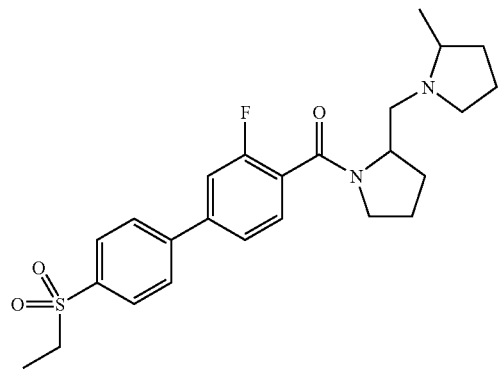 |
| X92 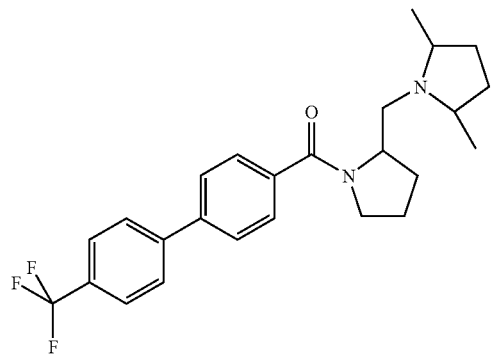 |
| X93 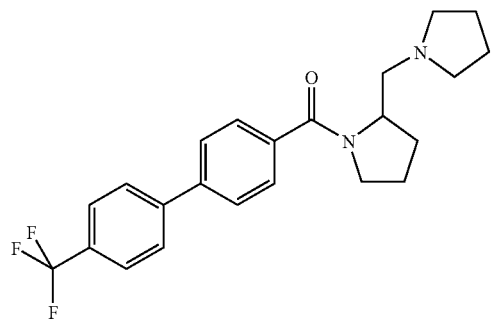 |

-continued
| Structure |
|---|
| X94 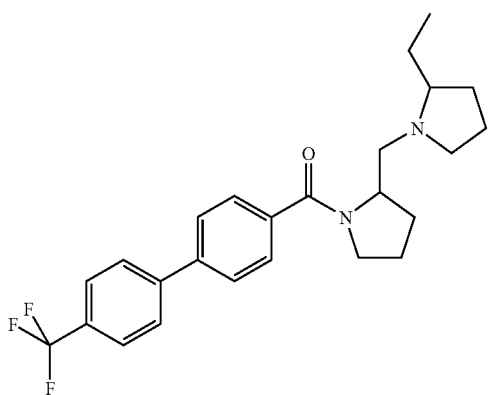 |
| X95 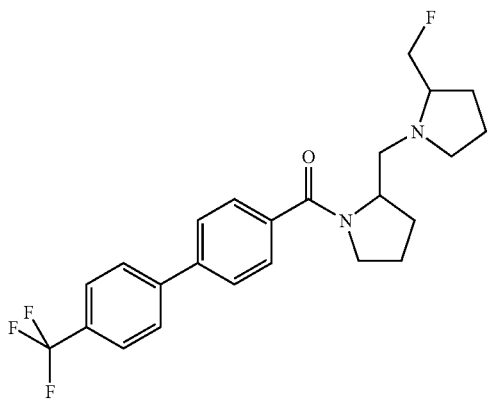 |
| X96 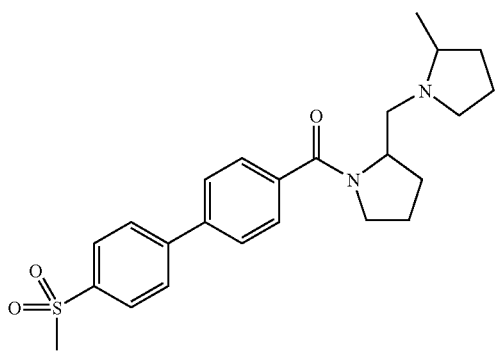 |
| X97 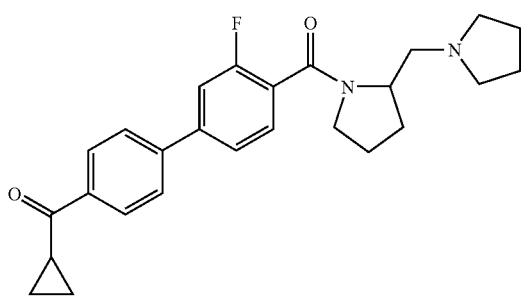 |

| Structure |
|---|
| X98 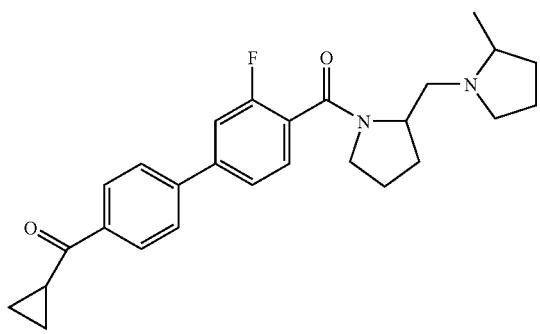 |
| X99 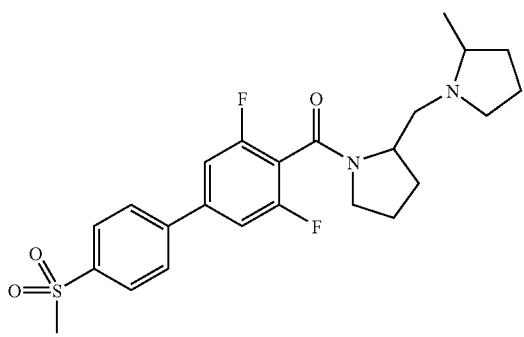 |
| X100 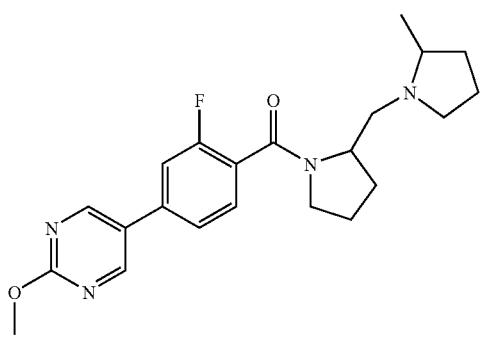 |
| X101 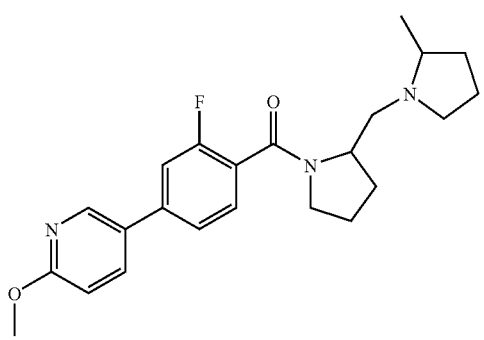 |

| Structure |
|---|
| X102 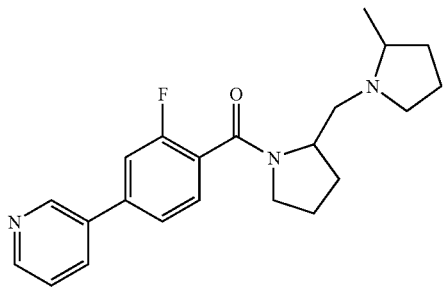 |
| X103 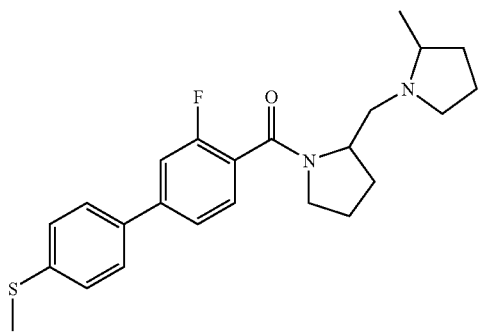 |
| X104 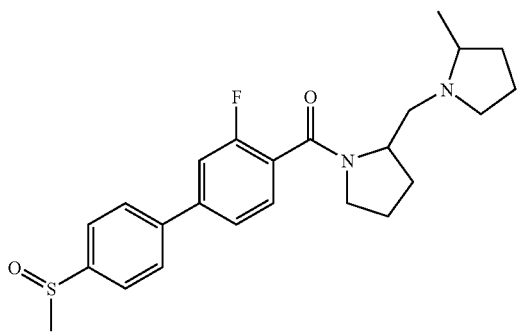 |
| X105 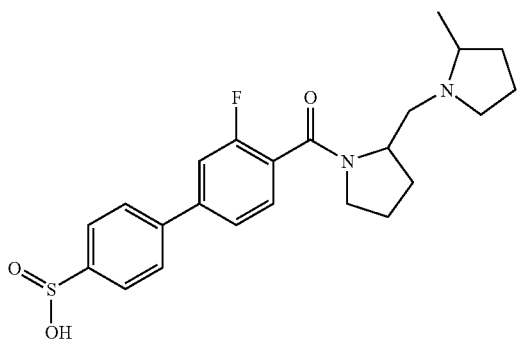 |

-continued
| Structure |
|---|
| X106 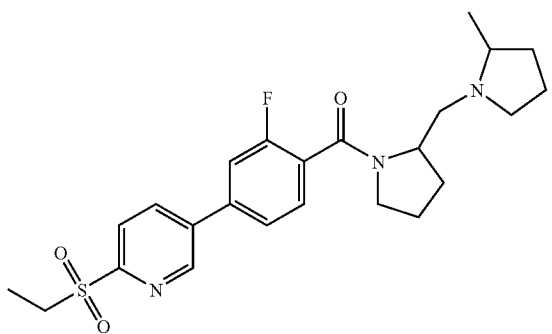 |
| X107 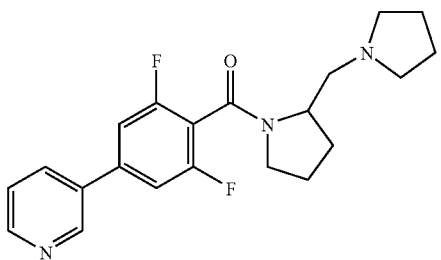 |
| X108 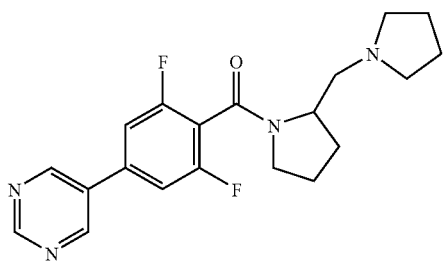 |
| X109 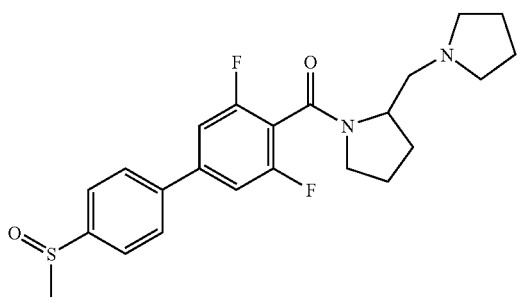 |
| X110 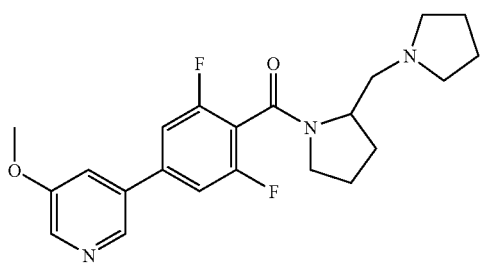 |

| Structure |
|---|
| X111 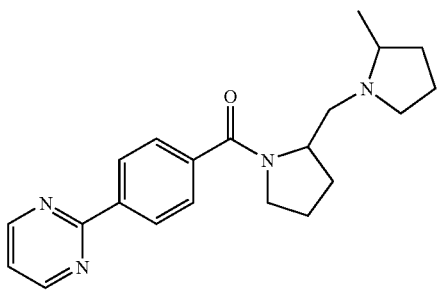 |
| X112 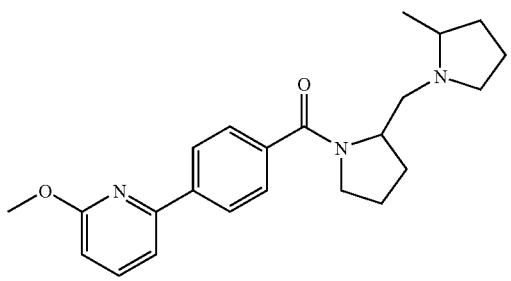 |
| X113 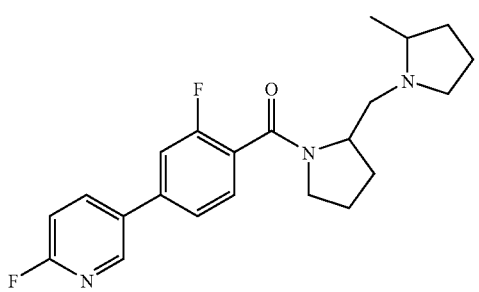 |
| X114 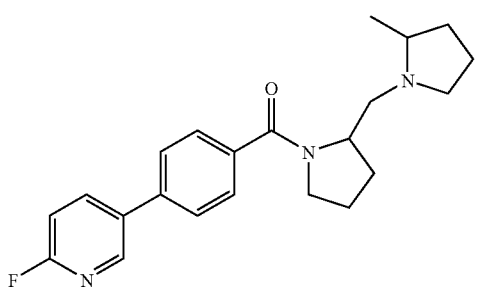 |
| X115 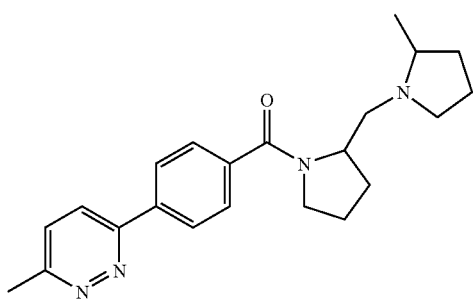 |
or a pharmaceutically acceptable salt thereof.
13. The compound of claim 1 selected from the group consisting of:
(2-(S)-Pyrrolidin-1-ylmethyl-pyrrolidin-1-yl)-(4'-trifluoromethyl-biphenyl-4-yl) -methanone;
(2-(S)-Pyrrolidin-1-ylmethyl-pyrrolidin-1-yl)-(2'-trifluoromethyl-biphenyl-4-yl) -methanone;
(4'-Chloro-biphenyl-4-yl)-(2-(S)-pyrrolidin-1-ylmethyl-pyrrolidin-1-yl)-methanone;

(2'-Chloro-biphenyl-4-yl)-(2-(S)-pyrrolidin-1-ylmethyl-pyrrolidin-1-yl)-methanone;
[4-(6-Methyl-pyridin-2-yl)-phenyl]-(2-(S)-pyrrolidin-1-ylmethyl-pyrrolidin-1-yl)-methanone;
[4'-(5-Methyl-[1,3,4]oxadiazol-2-yl)-biphenyl-4-yl]-(2-pyrrolidin-1-ylmethyl-pyrrolidin-1-yl)-methanone;
(3-Fluoro-biphenyl-4-yl)-(2-(S)-pyrrolidin-1-ylmethyl-pyrrolidin-1-yl)-methanone;
(3, 2'-Difluoro-biphenyl-4-yl)-(2-(S)-pyrrolidin-1-ylmethyl-pyrrolidin-1-yl)-methanone;
(2'-Fluoro-biphenyl-4-yl)-(2-(S)-pyrrolidin-1-ylmethyl-pyrrolidin-1-yl)-methanone;
(4'-Fluoro-biphenyl-4-yl)-(2-(S)-pyrrolidin-1-ylmethyl-pyrrolidin-1-yl)-methanone;
(2S-Pyrrolidin-1-ylmethyl-pyrrolidin-1-yl)-(3'-chloro-biphenyl-4-yl)-methanone;
(2S-Pyrrolidin-1-ylmethyl-pyrrolidin-1-yl)-(3'-trifluoromethyl-biphenyl-4-yl)-methanone;
(4-Pyrimidin-5-yl-phenyl)-(2 S-pyrrolidin-1-ylmethyl-pyrrolidin-1-yl)-methanone;
(2 S-Pyrrolidin-1-ylmethyl-pyrrolidin-1-yl)-[4-(6-trifluoromethyl-pyridin-3-yl)]-methanone;
(3-Chloro-4'-methanesulfonyl-biphenyl-4-yl)-(2S-pyrrolidin-1-ylmethyl-pyrrolidin-1-yl)-methanone;
(4-Pyridin-3-yl-phenyl)-(2S-pyrrolidin-1-ylmethyl-pyrrolidin-1-yl)-methanone;
(4-Pyridin-2-yl-phenyl)-(2S-pyrrolidin-1-ylmethyl-pyrrolidin-1-yl)-methanone;
4'-(2S-Pyrrolidin-1-ylmethyl-pyrrolidine-1-carbonyl)-biphenyl-4-carbonitrile;
(4-Pyridin-2-yl-phenyl)-(2S-pyrrolidin-1-ylmethyl-pyrrolidin-1-yl)-methanone;
(4-Pyridin-4-yl-phenyl)-(2S-pyrrolidin-1-ylmethyl-pyrrolidin-1-yl)-methanone;
4'-(2S-Pyrrolidin-1-ylmethyl-pyrrolidine-1-carbonyl)-biphenyl-4-sulfonic acid dimethylamide;
4'-(2S-Pyrrolidin-1-ylmethyl-pyrrolidine-1-carbonyl)-biphenyl-4-sulfonic acid tert-butylamide;
4'-(2S-Pyrrolidin-1-ylmethyl-pyrrolidine-1-carbonyl)-biphenyl-4-sulfonic acid amide;
4'-(2S-Pyrrolidin-1-ylmethyl-pyrrolidine-1-carbonyl)-biphenyl-4-sulfonic acid tert-butyl-methyl-amide;
4'-(2S-Pyrrolidin-1-ylmethyl-pyrrolidine-1-carbonyl)-biphenyl-4-sulfonic acid methylamide;
1-{6-[4-(2-(S)-Pyrrolidin-1-ylmethyl-pyrrolidine-1-carbonyl)-phenyl]-pyridin-3-yl}-ethanone;
4'-(2-(S)-Pyrrolidin-ylmethyl-pyrrolidine-1-carbonyl)-biphenyl-4-carboxylic acid methylamide;
4'(2-(S)-Pyrrolidin-ylmethyl-pyrrolidine-1-carbonyl)-biphenyl-4-carboxylic acid dimethylamide;
4'-(Methanesulfonyl-biphenyl-4-yl)-(2-(S)-pyrrolidin-1-ylmethyl-pyrrolidin-1-yl)-methanone;
[4'-(Pyrrolidine-1-carbonyl)-biphenyl-4-yl]-(2-(S)-pyrrolidin-1-ylmethyl-pyrrolidin-1-yl)-methanone;
(3-Fluoro-4'-methanesulfonyl-biphenyl-4-yl)-(2-(S)-pyrrolidin-1-ylmethyl-pyrrolidin-1-yl)-methanone;
N-[4'-(2-(S)-Pyrrolidin-1-ylmethyl-pyrrolidine-1-carbonyl)-biphenyl-4-yl]-methanesulfonamide;
N-[4'-(2-(S)-Pyrrolidin-1-ylmethyl-pyrrolidine-1-carbonyl)-biphenyl-3-yl]-methanesulfonamide;
(3Methanesulfonyl-biphenyl-4-yl)-(2-(S)-pyrrolidin-1-ylmethyl-pyrrolidin-1-yl)-methanone;
[4-(6-Ethanesulfonyl-pyridin-3-yl)-phenyl]-(2-(S)-pyrrolidin-1-ylmethyl-pyrrolidin-1-yl)-methanone;
[4-(6-Ethanesulfonyl-pyridin-3-yl)-2-fluoro-phenyl]-(2-(S)-pyrrolidin-1-ylmethyl-pyrrolidin-1-yl)-methanone;
N-{5-[4-(2-(S)-Pyrrolidin-1-ylmethyl-pyrrolidine-1-carbonyl)-phenyl]-pyridin-2-yl}-methanesulfonamide;
(2-(S)-Pyrrolidin-1-ylmethyl-pyrrolidin-1-yl)-(4'-trifluoromethanesulfonyl-biphenyl-4-y1)-methanone;
N-[3-Fluoro-4'-(2-(S)-pyrrolidin-1-ylmethyl-pyrrolidine-1-carbonyl)-biphenyl-4-yl]-methanesulfonamide;
(4'-Ethanesulfonyl-biphenyl-4-yl)-(2-(S)-pyrrolidin-1-ylmethyl-pyrrolidin-1-yl)-methanone;
(S)-(4'-Nitro-biphenyl-4-yl)-(2-pyrrolidin-1-ylmethyl-pyrrolidin-1-yl)-methanone;
(S)-(4'-Amino-biphenyl-4-yl)-(2-pyrrolidin-1-ylmethyl-pyrrolidin-1-yl)-methanone;
(S)-(4'-Methoxy-biphenyl-4-yl)-(2-pyrrolidin-1-ylmethyl-pyrrolidin-1-yl)-methanone;
(S)-(4'-Bromo-biphenyl-4-yl)-(2-pyrrolidin-1-ylmethyl-pyrrolidin-1-yl)-methanone;
(S)-(2'-Nitro-biphenyl-4-yl)-(2-pyrrolidin-1-ylmethyl-pyrrolidin-1-yl)-methanone;
(S)-(4'-Ethyl-biphenyl-4-yl)-(2-pyrrolidin-1-ylmethyl-pyrrolidin-1-yl)-methanone;
(S)-Biphenyl-4-yl-(2-pyrrolidin-1-ylmethyl-pyrrolidin-1-yl)-methanone;
(S)-(4'-Propyl-biphenyl-4-yl)-(2-pyrrolidin-1-ylmethyl-pyrrolidin-1-yl)-methanone;
(S)-[4'-(2-Piperidin-1-yl-ethoxy)-biphenyl-4-yl]-(2-pyrrolidin-1-ylmethyl-pyrrolidin-1-yl)-methanone;
(S)-(4'-tert-Butyl-biphenyl-4-yl)-(2-pyrrolidin-1-ylmethyl-pyrrolidin-1-yl)-methanone;
(S)-(4'-Hexyl-biphenyl-4-yl)-(2-pyrrolidin-1-ylmethyl-pyrrolidin-1-yl)-methanone;
(S)-(2-Pyrrolidin-1-ylmethyl-pyrrolidin-1-yl)-[1,1'; 3',1'''] terphenyl-4-yl-methanone;
3-Fluoro-4-pyridin-4-yl-phenyl)-(2S-Pyrrolidin-1-ylmethyl-pyrrolidin-1-yl)-methanone;
(2-Fluoro-4'-methanesulfonyl-biphenyl-4-yl)-(2S-pyrrolidin-1-ylmethyl-pyrrolidin-1-yl)-methanone;
[4-(2-Methoxy-pyrimidin-5-yl)-phenyl]-(2-(S)-pyrrolidin-1-ylmethyl-pyrrolidin-1-yl)-methanone;
[4-(6-Methoxy-pyridin-3-yl)-phenyl]-(2-(S)-pyrrolidin-1-ylmethyl-pyrrolidin-1-yl)-methanone;
(4-Benzo[1,3]dioxol-5-yl-phenyl)-(2-(S)-pyrrolidin-1-ylmethyl-pyrrolidin-1-yl)-methanone;
[4-(2,3-Dihydro-benzo[1,4]dioxin-6-yl)-phenyl]-(2-(S)-pyrrolidin-1-ylmethyl-pyrrolidin-1-yl)-methanone;
(2-Fluoro-4-pyridin-4-yl-phenyl)-(2(S)-pyrrolidin-1-ylmethyl-pyrrolidin-1-yl)-methanone;
[2-(S)-(2-Methyl-pyrrolidin-1-ylmethyl)-pyrrolidin-1-yl]-(4'-trifluoromethyl-biphenyl-4-yl)-methanone isomer 1;
[2-(S)-(2-Methyl-pyrrolidin-1-ylmethyl)-pyrrolidin-1-yl]-(4'-trifluoromethyl-biphenyl-4-yl)-methanone isomer 2;
(2-Fluoro-3-pyridin-4-yl-phenyl)-(2(S)-pyrrolidin-1-ylmethyl-pyrrolidin-1-yl)-methanone;
(4'-Methanesulfonyl-4-trifluoromethyl-biphenyl-3-yl)-(2-(S)-pyrrolidin-1-ylmethyl-pyrrolidin-1-yl)-methanone;
(5-Pyridin-4-yl-2-trifluoromethyl-phenyl)-(2-(S)-pyrrolidin-1-ylmethyl-pyrrolidin-1-yl)-methanone;
(3,5-Difluoro-4'-methanesulfonyl-biphenyl-4-yl)-(2-(S)-pyrrolidin-1-ylmethyl-pyrrolidin-1-yl)-methanone;
(2,6-Difluoro-4-pyridin-4-yl-phenyl)-(2-(S)-pyrrolidin-1-ylmethyl-pyrrolidin-1-yl)-methanone;
[2,6-Difluoro-4-(2-methoxy-pyrimidin-5-yl)-phenyl]-(2-(S)-pyrrolidin-1-ylmethyl-pyrrolidin-1-yl)-methanone;
N-[3'-Fluoro-4'-(2-(S)-pyrrolidin-1-ylmethyl-pyrrolidine-1-carbonyl)-biphenyl-4-yl]-methanesulfonamide;

N-[3'-Fluoro-4'-(2-(S)-pyrrolidin-1-ylmethyl-pyrrolidine-1-carbonyl)-biphenyl-4-yl]-N-methyl-methanesulfonamide;

[2-(S)-(2-(R)-Methyl-pyrrolidin-1-ylmethyl)-pyrrolidin-1-yl]-(4'-trifluoromethyl-biphenyl-4-yl)-methanone;

(3-Fluoro-3'-trifluoromethyl-biphenyl-4-yl)-(2-(S)-pyrrolidin-1-ylmethyl-pyrrolidin-1 -yl)-methanone;

(3-Fluoro-4'-trifluoromethyl-biphenyl-4-yl)-(2-(S)-pyrrolidin-1-ylmethyl-pyrrolidin-1 -yl)-methanone;

3'-Fluoro-4'-(2-(S)-pyrrolidin-1-ylmethyl-pyrrolidine-1-carbonyl)-biphenyl-3-carbonitrile;

(3-Fluoro-3 '-trifluoromethoxy-biphenyl-4-yl)-(2-(S)-pyrrolidin-1-ylmethyl-pyrrolidin-1-yl)-methanone;

(3 -Fluoro-4'-trifluoromethoxy-biphenyl-4-yl)-(2-(S)-pyrrolidin-1-ylmethyl-pyrrolidin-1-yl)-methanone;

(3 -Fluoro-2', 4'-dimethoxy-biphenyl-4-yl)-(2-(S)-pyrrolidin-1-ylmethyl-pyrrolidin-1 -yl)-methanone;

(3-Fluoro-4'-methoxy-biphenyl-4-yl)-(2-(S)-pyrrolidin-1-ylmethyl-pyrrolidin-1-yl) -methanone;

(3-Fluoro-3', 4'-dimethoxy-biphenyl-4-yl)-(2-(S)-pyrrolidin-1-ylmethyl-pyrrolidin-1-yl)-methanone;

(3,4'-Difluoro-biphenyl-4-yl)-(2-(S)-pyrrolidin-1-ylmethyl-pyrrolidin-1-yl)-methanone;

(4-Benzo[1,3 ]dioxol-5-yl-2-fluoro-phenyl)-(2-(S)-pyrrolidin-1-ylmethyl-pyrrolidin-1-yl)-methanone;

[4-(2,3 -Dihydro-benzo [1,4]dioxin-6-yl)-2-fluoro-phenyl]-(2-(S)-pyrrolidin-1-ylmethyl-pyrrolidin-1 -yl)-methanone;

(3 -Fluoro-3 '-pyrrolidin-1-yl-biphenyl-4-yl)-(2-(S)-pyrrolidin-1-ylmethyl-pyrrolidin-1-yl)-methanone;

(3-Fluoro-3 '-methanesulfonyl-biphenyl-4-yl)-(2-(S)-pyrrolidin-1-ylmethyl-pyrrolidin-1-yl)-methanone;

(4'-Ethanesulfonyl-3-fluoro-biphenyl-4-yl)-(2-(S)-pyrrolidin-1-ylmethyl-pyrrolidin-1-yl)-methanone;

(3-Fluoro-4'-methanesulfinyl-biphenyl-4-yl)-(2-(S)-pyrrolidin-1-ylmethyl-pyrrolidin-1-yl)-methanone;

(2-Fluoro-4-pyrimidin-5-yl-phenyl)-(2-(S)-pyrrolidin-1-ylmethyl-pyrrolidin-1-yl) -methanone;

[2-Fluoro-4-(2-methoxy-pyrimidin-5-yl)-phenyl]-(2-(S)-pyrrolidin-1-ylmethyl-pyrrolidin-1-yl)-methanone;

[2-Fluoro-4-(6-methoxy-pyridin-3-yl)-phenyl]-(2-(S)-pyrrolidin-1-ylmethyl-pyrrolidin-1-yl)-methanone;

[2-Fluoro-4-(1H-indol-5-yl)-phenyl]-(2-(S)-pyrrolidin-1-ylmethyl-pyrrolidin-1 -yl) -methanone;

(2-Fluoro-4-quinolin-3-yl-phenyl)-(2-(S)-pyrrolidin-1-ylmethyl-pyrrolidin-1-yl) -methanone;

(4'-Ethanesulfonyl-3-fluoro-biphenyl-4-yl)-[2-(S)-(2-(R)-methyl-pyrrolidin-1-ylmethyl)-pyrrolidin-1-yl]-methanone;

[2-(2,5-trans-Dimethyl-pyrrolidin-1-ylmethyl)-pyrrolidin-1-yl]-(4'-trifluoromethyl-biphenyl-4-yl)-methanone;

[2-(2,5-cis-Dimethyl-pyrrolidin-1-ylmethyl)-pyrrolidin-1-yl]-(4'-trifluoromethyl-biphenyl-4-yl)-methanone;

(2-(R)-Pyrrolidin-1-ylmethyl-pyrrolidin-1-yl)-(4'-trifluoromethyl-biphenyl-4-yl) -methanone;

[2-(S)-(2-(R)-Ethyl-pyrrolidin-1-ylmethyl)-pyrrolidin-1-yl]-(4'-trifluoromethyl-biphenyl-4-yl)-methanone;

[2-(S)-(2-(S)-Fluoromethyl-pyrrolidin-1-ylmethyl)-pyrrolidin-1-yl]-(4'-trifluoromethyl-biphenyl-4-yl)-methanone;

(4'-methanesulfonyl-biphenyl-4-yl)-[2-(S)-(2-(R)-methyl-pyrrolidin-1-ylmethyl) -pyrrolidin-1 -yl]-methanone;

(4'-Cyclopropanecarbonyl-3-fluoro-biphenyl-4-yl)-(2-(S)-pyrrolidin-1-ylmethyl-pyrrolidin-1-yl)-methanone;

Cyclopropyl-{3'-fluoro-4'-[2-(S)-(2-(R)-methyl-pyrrolidin-1-ylmethyl)-pyrrolidine-1-carbonyl]-biphenyl-4-yl}-methanone;

(3,5-Difluoro-4'-methanesulfonyl-biphenyl-4-yl)-(2-(R)-methyl-1-(2-(S) -pyrrolidinylmethyl)pyrrolidin-1-yl)-methanone;

(2-Fluoro-4-[2-methoxy-pyrimidin-5-yl]-phenyl)-(2-(R)-methyl-1-(2-(S) -pyrrolidinylmethyl)pyrrolidin-1-yl)-methanone L-tartrate;

(2-Fluoro-4-[6-methoxy-pyridin-3-yl]-phenyl)-(2-(R)-methyl-1-(2-(S) -pyrrolidinylmethyl)pyrrolidin-1-yl)-methanone;

(2-Fluoro-4-pyridin-3-yl-phenyl)-(2-(R)-methyl-1-(2-(S)-pyrrolidinylmethyl)pyrrolidin-1-yl)-methanone;

(3-Fluoro-4'-methylthio-biphenyl-4-yl)-(2-(R)-methyl-1-(2-(S) -pyrrolidinylmethyl)pyrrolidin-1-yl)-methanone;

(3 -Fluoro-4'-methanesulfinyl-biphenyl-4-yl)-(2-(R)-methyl-1-(2-(S) -pyrrolidinylmethyl)pyrrolidin-1-yl)-methanone;

3 '-Fluoro-4-[(2-(R)-methyl-1-(2-(S)-pyrrolidinylmethyl) pyrrolidine-1-carbonyl]-biphenyl-4-sulfinic acid;

[4-(6-Ethanesulfonyl-pyridin-3-yl)-2-fluoro-phenyl]-[2-(S)-(2-(R)-methyl-pyrrolidin-1-ylmethyl)-pyrrolidin-1-yl]-methanone;

(2,6-Difluoro-4-pyridin-3-yl-phenyl)-((S)-2-pyrrolidin-1-ylmethyl-pyrrolidin-1-yl) -methanone;

(2,6-Difluoro-4-pyrimidin-5-yl-phenyl)-((S)-2-pyrrolidin-1-ylmethyl-pyrrolidin-1-yl) -methanone;

(3,5-Difluoro-4'-methanesulfinyl-biphenyl-4-yl)-((S)-2-pyrrolidin-1-yl methyl-pyrrolidin-1-yl)-methanone;

([2,6-Difluoro-4-(5-methoxy-pyridin-3-yl)-phenyl]-((S)-2-pyrrolidin-1-ylmethyl-pyrrolidin-1 -yl)-methanone;

[2-(S)-(2-(R)-Methyl-pyrrolidin-1-ylmethyl]-(4-pyrimidin-2-yl-phenyl)-methanone;

[4-(6-Methoxy-pyridin-2-yl)-phenyl]-[2-(S)-(2-(R)-Methyl-pyrrolidin-1-ylmethyl) -pyrrolidin-1-yl]-methanone;

[2-Fluoro-4-(6-fluoro-pyridin-3-yl)-phenyl]-[2-(S)-(2-(R)-Methyl-pyrrolidin-1-ylmethyl)-pyrrolidin-1-yl]-methanone;

[4-(6-Fluoro-pyridin-3-yl)-phenyl]-[2-(S)-(2-(R)-Methyl-pyrrolidin-1-ylmethyl) -pyrrolidin-1-yl]-methanone; and

[4-(6-Methyl-pyridazin-3-yl)-phenyl]-[2-(S)-(2-(R)-Methyl-pyrrolidin-1-ylmethyl) -pyrrolidin-1-yl]-methanone;

or a pharmaceutically acceptable salt thereof.

14. A pharmaceutical composition which comprises a compound or salt of claim 1 and a pharmaceutically acceptable carrier.

* * * * *